United States Patent
Berlinger et al.

(10) Patent No.: US 12,112,845 B2
(45) Date of Patent: *Oct. 8, 2024

(54) COMPARTMENTALIZED DYNAMIC ATLAS

(71) Applicant: Brainlab AG, Munich (DE)

(72) Inventors: Kajetan Berlinger, Munich (DE);
Andreas Blumhofer, Neubiberg (DE)

(73) Assignee: Brainlab AG, Munich (DE)

( * ) Notice: Subject to any disclaimer, the term of this patent is extended or adjusted under 35 U.S.C. 154(b) by 453 days.

This patent is subject to a terminal disclaimer.

(21) Appl. No.: 17/281,644

(22) PCT Filed: Nov. 7, 2018

(86) PCT No.: PCT/EP2018/080491
§ 371 (c)(1),
(2) Date: Mar. 31, 2021

(87) PCT Pub. No.: WO2020/094226
PCT Pub. Date: May 14, 2020

(65) Prior Publication Data
US 2021/0391061 A1    Dec. 16, 2021

(51) Int. Cl.
*G06K 9/00*     (2022.01)
*G06T 7/00*     (2017.01)
*G16H 30/40*    (2018.01)

(52) U.S. Cl.
CPC ........... *G16H 30/40* (2018.01); *G06T 7/0016* (2013.01); *G06T 2207/10076* (2013.01); *G06T 2207/10081* (2013.01)

(58) Field of Classification Search
CPC . G06T 2207/20128; G06T 2207/10076; G06T 7/0016; G06T 2207/30241;
(Continued)

(56) References Cited

U.S. PATENT DOCUMENTS

| 8,597,211 B2 | 12/2013 | Berlinger |
| 9,014,424 B2 | 4/2015 | Berlinger et al. |

(Continued)

FOREIGN PATENT DOCUMENTS

| EP | 2912632 | 9/2015 |
| WO | 2017140352 | 8/2017 |

OTHER PUBLICATIONS

G. Gerig et al., "Computational Anatomy to Assess Longitudinal Trajectory of Brain Growth," Third International Symposium on 3D Data Processing, Visualization, and Transmission (3DPVT'06), Chapel Hill, NC, USA, 2006, pp. 1041-1047, doi: 10.1109/3DPVT. 2006.41. (Year: 2006).*

(Continued)

*Primary Examiner* — Atiba O Fitzpatrick
(74) *Attorney, Agent, or Firm* — Gray Ice Higdon

(57) ABSTRACT

A compartmentalized dynamic anatomic atlas is disclosed, comprising static atlas data comprising spatial element data and element representation data, wherein the spatial element data describes spatial properties of a spatial atlas element and wherein the element representation data describes representational properties assignable to the spatial atlas element, the atlas further comprising dynamic atlas data comprising information on a dynamic property which information is respectively linked to the spatial atlas element.

15 Claims, 18 Drawing Sheets

S3.1: 4DCT of at least one patient

S3.2: Compute trajectories via elastic fusion for e.g. every voxel

S3.3: Compute movement correlation values for e.g. every voxel (e.g. diaphragm to pancreas) based on trajectories S3.4: Store normalized trajectories and movement correlation values as dynamic atlas data

(58) Field of Classification Search
CPC ........... G06T 7/20; G06T 7/215; G06T 7/223; G06T 7/246; G06T 7/248; G06T 7/251; G06T 7/30; G06T 7/70; G06T 2207/20076; G06T 7/0012; G06T 7/0014; G06T 2207/10081; G06T 2207/10072–10128; A61B 2034/107
See application file for complete search history.

(56) References Cited

U.S. PATENT DOCUMENTS

| | | | |
|---|---|---|---|
| 2009/0131782 A1 | 5/2009 | Moonen et al. | |
| 2010/0286995 A1* | 11/2010 | Pekar | G16H 50/50 705/2 |
| 2012/0288173 A1 | 11/2012 | Rai et al. | |
| 2013/0044927 A1* | 2/2013 | Poole | G06T 7/0014 382/128 |
| 2014/0161329 A1* | 6/2014 | Tizhoosh | G06T 7/149 382/128 |
| 2014/0226889 A1* | 8/2014 | Liu | G06T 7/174 382/131 |
| 2015/0278471 A1 | 10/2015 | Blumhofer et al. | |
| 2015/0287195 A1* | 10/2015 | Vilsmeier | G16H 50/50 382/130 |
| 2015/0302608 A1* | 10/2015 | Vilsmeier | G06T 7/251 382/131 |
| 2016/0343127 A1* | 11/2016 | Miller | G06T 7/11 |
| 2017/0109871 A1* | 4/2017 | Nakano | G06T 7/11 |
| 2017/0330324 A1 | 11/2017 | Blumhofer | |
| 2017/0348056 A1* | 12/2017 | Steinle | A61B 34/30 |
| 2018/0005378 A1 | 1/2018 | Varkuti et al. | |
| 2018/0005381 A1* | 1/2018 | Patel | G06T 7/0014 |
| 2018/0096478 A1* | 4/2018 | Zhang | G06N 3/08 |
| 2018/0101954 A1* | 4/2018 | Magda | G06T 7/11 |

OTHER PUBLICATIONS

International Search Report and Written Opinion issued for Application No. PCT/EP2018/080491 dated Jul. 11, 2019.
Liu et al., "Prediction-driven Respiratory Motion Atlas Formation for 4 D Image-guided Radiation Therapy in Lung" 12 pages.

* cited by examiner

| Correlation of movement trajectory 4a ↔ 4b = 5 (medium) | Correlation of movement trajectory 4a ↔ 4c = 1 (low) | Correlation of movement trajectory 4a ↔ 4d = 9 (high) |
|---|---|---|
| Correlation of volumetric change 4a ↔ 4b = 52 (medium) | Correlation of volumetric change 4a ↔ 4c = 8 (low) | Correlation of volumetric change 4a ↔ 4d = 97 (high) |
| ... | ... | ... |

Table 401

| atlas element | representation class |
|---|---|
| 401 | 400A |
| 402 | 400B |
| 403 | 400A |
| 404 | 400C |
| 405 | 400D |
| 406 | 400A |
| 407 | 400B |

Table 402

| parameter set / representation class | α | β | γ |
|---|---|---|---|
| 400A | 400a | 400d | 400a |
| 400B | 400b | 400e | 400g |
| 400C | 400c | 400f | 400h |
| 400D | 400c | 400d | 400i |

| Table 403 | |
|---|---|
| representation data set | representation information (visual appearance) |
| 400a |  |
| 400b |  |
| 400c |  |
|  |  |
| 400g |  |
| 400h |  |
| 400i |  |

S123 acquiring a description of representation data sets

S124 acquiring the determination rule by performing the steps of:

- selecting a representation class on the basis of an atlas element identifier, using Table 401;

- determining a representation data set on the basis of the selected representation class and the parameter set associated with the patient image, using Table 402;

- determining the representation of the atlas element on the basis of the determined representation data set, using Table 403.

Fig. 15B

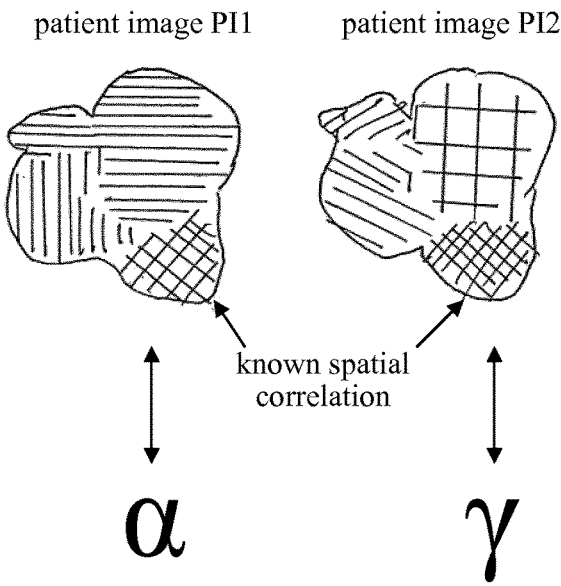

patient image PI1   patient image PI2 known spatial correlation

α   γ

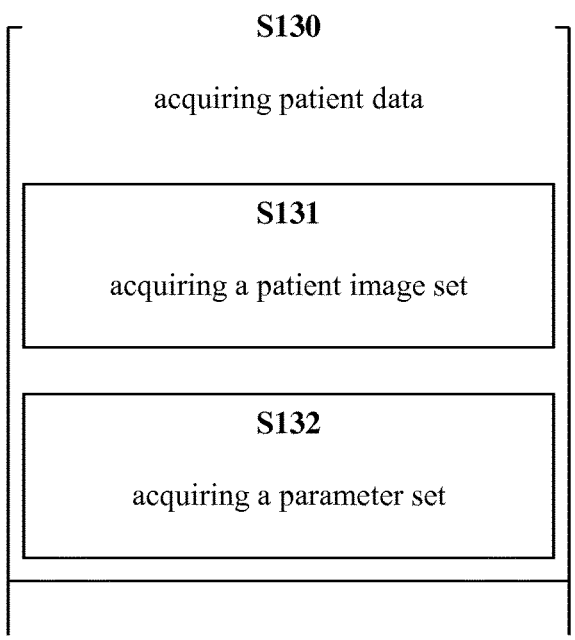

S130 acquiring patient data

S131 acquiring a patient image set

S132 acquiring a parameter set

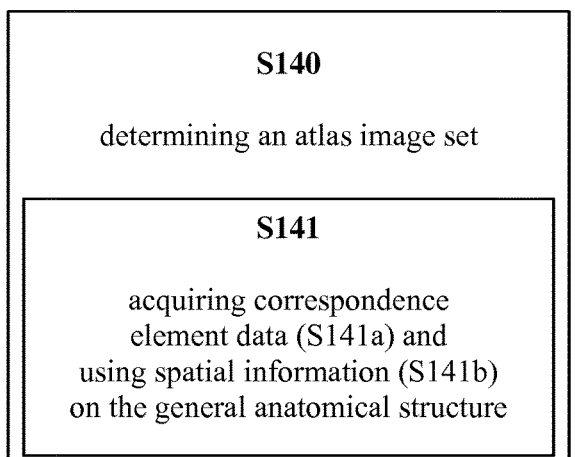

S140 determining an atlas image set

S141 acquiring correspondence element data (S141a) and using spatial information (S141b) on the general anatomical structure S142 applying the determination rule in order to determine representation data sets for the corresponding elements (404, 405, 406, 407)

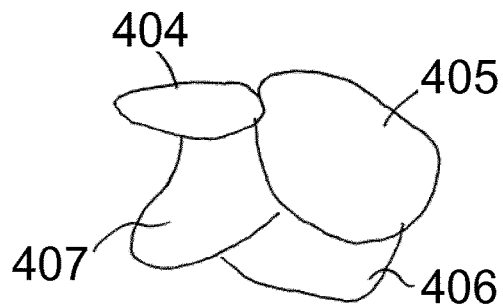

Table 404

| α | | γ | |
|---|---|---|---|
| 404 | 400c | 404 | 400h |
| 405 | 400c | 405 | 400i |
| 406 | 400a | 406 | 400a |
| 407 | 400b | 407 | 400g |

Fig. 15C

COMPARTMENTALIZED DYNAMIC ATLAS

The present invention relates to a compartmentalized dynamic anatomic atlas comprising static atlas data and dynamic atlas data. The invention also relates to a computer implemented data processing method comprising the step of acquiring the dynamic anatomic atlas, a method for generating the compartmentalized dynamic anatomic atlas and a use of the compartmentalized dynamic anatomic atlas. It also relates to a computer program, a non-transitory computer-readable storage medium and a computer.

TECHNICAL BACKGROUND

Physiologic movements like vital movements, conscious and unconscious movements and others as well as other time-dependent (dynamic) spatial properties have not been considered within a known anatomical atlas. The term "vital movement" means that the body parts are moved by vital functions of the body such as respiration and/or heartbeat. These functions of the body sustain life. Conscious movements can be consciously controlled, i.e. muscle movements, for example to move a limb. Unconscious movements are movements which cannot be controlled by will, i.e. the heartbeat. Other physiologic movements for example include movements of body fluids such as the blood. Examples of other time-dependent properties include for example the change of temperature, the change of pressure and the change of concentration of a given substance.

One idea underlying the current invention is the integration of dynamic information described by dynamic atlas data (for example the information gained using physiologic volume rendering as disclosed in PCT/EP2016/053291 (as described in Annex A) into an anatomic atlas. According to PCT/EP2016/053291 (as described in Annex A), via elastic fusion—of a reference bin of a 4D CT to the remaining bins—for every voxel a trajectory is computed which describes a time-dependent change of position of the individual pixel. Each trajectory can then be correlated to other trajectories, for example to find out what structures move in a similar way as a target structure such as a tumor. The result can subsequently be displayed as a "heatmap" indicating the degree of similarity of movement of each voxel to a target structure, for example based on the determined correlations.

The dynamic atlas data (e.g. general trajectory, and movement correlation) of certain areas or structures obtained in this way shall be stored in an anatomical atlas, for example as meta data. This enables the analysis of newly acquired individual timely resolved patient image data (e.g. 4D CT data) using this dynamic information described by the dynamic atlas data.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

A compartmentalized dynamic anatomic atlas is disclosed. Compared to a commonly known anatomic atlas which for example includes atlas images, this atlas comprises static atlas data which is compartmentalized into spatial element data (describing atlas spatial information mentioned in Annex B) and element representation data (describing element representation information mentioned in Annex B), giving the atlas its name prefix "compartmentalized".

In more detail, the spatial element data for example describe spatial information data sets (also referred to as "sets of spatial information" in Annex B) which respectively describe at least one a spatial property of a spatial atlas element. The element representation data describes representation data sets describing a representational property of the spatial atlas element, which can for example be clustered into representation classes.

For example, the static atlas data is compartmentalized into at least two separate compartments, one of which includes (only) atlas spatial information and the other of which includes (only) element representation information as described in Annex B in detail. This enables the use (for instance processing) of solely spatial properties of a so-called spatial atlas element for the purposes described herein. For example, the use of the spatial properties of spatial atlas elements separately from representational properties to be selected for the spatial atlas elements. The spatial properties available for selection are described by so-called representation data sets. That is, the compartmentalization enables the selection of a suitable representation data set comprising representational properties for the spatial atlas element, depending on the intended use of the atlas. The selection is also described as assignment in Annex B. For example, depending on the image modality of the patient image, a representation data set is selected for a spatial atlas element which enables the generation of an atlas image element using the spatial atlas element and the representational property of selected the representation data set. Afterwards, a matching can be performed between the at least one generated atlas image element and the patient image, resulting in an improved matching accuracy and reliability. Also, patient images can be used in this way to enrich an existing compartmentalized atlas by adding the representation information of a matched patient element to a given representation data set of the corresponding spatial atlas element. The inventors have found that the compartmentalization enables also a linking of dynamic properties of spatial atlas elements to spatial properties of spatial atlas elements independently from the representational properties of the atlas elements. This independent linking is described in more detail below.

As indicated above, the atlas further comprises dynamic atlas data, giving the atlas its name prefix "dynamic". This dynamic atlas data describes the dynamic properties, for example dynamic physical properties, for example dynamic spatial properties, for example time-dependent spatial physical properties of the spatial atlas elements (for example movement of the spatial atlas elements, a deformation thereof and/or a correlation of movement or deformation between different spatial atlas elements).

The compartmentalized dynamic anatomic atlas can be generated based on 3D image data enriched with dynamic data, referred to as dynamic DRR, dynamic CT or similarity image (see Annex A). The dynamic CT is for example generated based on a 4D CT. The dynamic CTs of a plurality of patients are each matched with an atlas image generated from the spatial element data and the element representation data. The dynamic data of a matched patient element (contained in the dynamic CT of the patient) is transferred to the corresponding atlas element (enrichment (for example linking) of static atlas data with the dynamic atlas data). Since a plurality of patients should be used to generate the compartmentalized dynamic atlas, a normalization of the dynamic data should be performed.

The compartmentalized dynamic anatomic atlas can be used to classify a patient into a patient category (age, sex, type of disease etc.) depending on the movement of patient elements. Also, elements in a patient which cannot be identified as critical in static patient images, but which move abnormally compared to the dynamic property of the corresponding spatial atlas element can be determined, e.g. non-enhancing lung tumors which are attached to a rib. Furthermore, the dynamic atlas data can be used to divide static atlas elements into sub-elements which move differently from each other (e.g. division of lung into a plurality of elements), thereby increasing the accuracy of results obtainable using the anatomic atlas.

GENERAL DESCRIPTION OF THE PRESENT INVENTION

In this section, a description of the general features of the present invention is given for example by referring to possible embodiments of the invention.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can for example be added to said other embodiment.

The invention relates to a compartmentalized dynamic anatomic atlas. The compartmentalized dynamic anatomical atlas may be stored as data in a storage device such as a non-transitory storage medium. The compartmentalized dynamic anatomic atlas for example is an atlas which can be used in a way similar to that of an anatomical atlas. This type of atlas (the anatomical atlas) is for example described in the chapter "Definitions". The anatomical atlas can for example be an anatomical atlas referred to as "universal anatomical atlas", generated for example described in the chapter "Definitions" below and used for example as described in the chapter "Definitions" below. The anatomical atlas is for example an atlas as described in Annex B. In difference to all these atlas, the compartmentalized dynamic anatomical atlas additionally includes information on a dynamic property as will be described below. Also, the static atlas data comprised in the atlas is compartmentalized as will be described below. Therefore, the atlas is also referred to as "compartmentalized dynamic anatomical atlas".

The compartmentalized dynamic anatomical atlas comprises static atlas data. The static atlas data may be data comprised in an anatomical atlas as described in the chapter "Definitions". The static atlas data described herein corresponds to the "atlas data" described in Annex B. That is, the static atlas data is compartmentalized (i.e. divided, separated or partitioned) into spatial element data (referred to in Annex B as "atlas spatial information") and element representation data (referred to in Annex B as "element representation information").

Note that although the description and the claims may refer to "a spatial atlas element", "a patient element", "a corresponding patient element", "a corresponding spatial atlas element", "an atlas image element" and other terms in singular form, the plural form is always also included in these terms as far as possible. For example, the spatial element data describes a spatial atlas element, but it can also comprise more than one spatial atlas element; a patient image comprises a patient element, but it can also comprise more than one patient element, and so on.

The spatial element data for example describes a spatial atlas element. For example, the spatial element data consists of spatial information data sets. A spatial information data set for example describes a spatial property of a spatial atlas element. For example, each of the spatial information data sets describes a spatial property of a different spatial atlas element. The spatial atlas element for example represents an anatomical body part in an abstract form, i.e. it only represents the spatial properties of the anatomical body part. That is, the spatial atlas element is not assigned a particular representation data set and therefore not assigned a representational property. In Annex B, the spatial atlas element is also referred to as "white atlas element" for that reason. The "spatial information data set" described in Annex B is the same as the spatial information data set described herein. For details on the structure, contents and creation of these data sets, it is therefore also referred to Annex B. The spatial properties described by a spatial data set include for example at least one of the geometry (shape and/or size, volume, length, height, diameter etc.) and position of the respective spatial atlas element. For example, the spatial element data includes two spatial information data sets, wherein one describes the geometry and position of the lung and the other one describes the geometry and position of a rib. As noted above and as described in detail in Annex B, the spatial element data does not include any information about the representational properties of the atlas elements. To enrich the spatial element data with such information, the use of the element representation data is necessary. That is, a spatial atlas element which spatial properties are described by a spatial information data set comprised in the spatial element data can be assigned a certain representational property described by a representation data set, wherein the representation data set is comprised in the element representation data. How the suitable representation data set is selected is described in detail in Annex B. In order to generate an atlas image element, i.e. a visual representation of a spatial atlas element, both the spatial properties and the representational properties associated with the spatial atlas element have to be used. Whilst the spatial element data does not contain any information about the representational properties of spatial atlas elements, the element representation data does. On the other hand, the element representation data does not contain any information about the spatial properties of the spatial atlas element. That is, the spatial element data and the element representation data are separate entities which are strictly separated from one another. For that reason, the static atlas data which comprises both the spatial element data and the element representation data is referred to as "compartmentalized", i.e. it is divided/partitioned into the aforementioned two separate entities.

The intermediate "spatial information data sets" are not necessarily provided. In either case, with or without the spatial information data sets, the spatial element data describes spatial properties of a spatial atlas element. The spatial atlas data described herein is equal to the "atlas spatial information" described in Annex B. Therefore, it is referred to Annex B for details on the contents and structure of the spatial element data. Also, the representation data sets do not need to be clustered into representation classes. Also, only a single representation data set may be provided. In any case, the element representation data describes representational properties assignable to the spatial atlas elements. These representational properties are for example grey values. The element representation data described herein is equal to the "element representation information" described in Annex B. Therefore, it is also referred to Annex B for details on the contents and structure of the element representation data and for details on how a representational property is assigned to a spatial atlas element or, in the words of Annex B, how an atlas image can be determined using the representation data set and a white atlas element.

For the generation of the spatial element data, the geometry of an element can for example be measured in medical images, using hardware measurement tools such as rulers or using common imaging methods such as digital images of a patient. The position can for example be determined in the same way. Details about the generation of the spatial element data and the element representation data are given in Annex B. The "atlas spatial information" in Annex B equals the spatial element data described herein whilst the "element representation information" in Annex B equals the element representation data described herein. Also, the "atlas data" in Annex B equals the static atlas data described herein.

The compartmentalized dynamic anatomical atlas further comprises dynamic atlas data. The dynamic atlas data is for example stored as meta data.

The dynamic atlas data for example comprises information on a dynamic property. The dynamic property for example describes a (time-dependent) change of a spatial property, i.e. a dynamic spatial property, of an atlas element. The dynamic property is for example at least one of the change of geometry (shape and/or size, volume, length, height, diameter etc.) and/or position of the spatial atlas element. The dynamic atlas data for example comprises information on at least one dynamic property, for example information on a plurality of dynamic properties, for example different types of dynamic properties. For example, the dynamic property is at least one of a change of position of an object and a change of geometry of an object, wherein the object is at least one of the spatial atlas element and spatial atlas sub-element. The spatial atlas sub-element is for example part of the spatial atlas element. In particular, it can represent on of a plurality of spatial atlas sub-elements which form, represent or make up the spatial atlas element. The spatial atlas sub-elements can be determined as described further below. The same applies to the "patient element" and the "patient sub-element", mutatis mutandis. It is noted that also patient elements may exhibit dynamic properties. In this case, the dynamic property is at least one of a change of position of an object and a change of geometry of an object, wherein the object is at least one of the patient element and a sub-element thereof. However, as the name already implies, the compartmentalized dynamic anatomic atlas contains dynamic atlas data which comprises information on a dynamic property related to spatial atlas elements and not to patient elements.

The dynamic properties may be determined in a way similar to the measurement of the spatial property described above for the static atlas data. Dynamic properties may be determined by measuring a time-dependent response of a patients' body to a change, like a stimulus, e.g. local and/or external temperature change, application of medication, physical exhaustion etc. In a preferred embodiment, the dynamic property is for example defined by a trajectory, for example a trajectory describing the time-dependent movement of a spatial atlas element. In particular, the information on the dynamic property contains at least one trajectory defining a time-dependent position of a spatial atlas element (and/or a sub-element thereof). The trajectory may alternatively or at the same time define a time-dependent position of a point with a known spatial relationship to the spatial atlas element (and/or to the sub-element thereof), such as a center or a point on the outline of spatial atlas element (and/or to the sub-element thereof). It is noted that also patient elements may exhibit dynamic properties which can in turn also be defined by such a trajectory. However, as the name implies, the compartmentalized dynamic anatomic atlas contains dynamic atlas data comprising information on a dynamic property of a spatial atlas element and not of a patient element.

The dynamic property may describe a plurality of trajectories (for example several or a multitude thereof) for a spatial atlas element, for example one trajectory for each voxel of a spatial atlas element or a trajectory for several voxels on the outer periphery of a spatial atlas element, e.g. a trajectory for each voxel forming the outline (the outermost layer of voxels) of the spatial atlas element. Of course, other voxels within the spatial atlas element can be described with such trajectories in addition or alternatively thereto, e.g. one or more voxels in the middle of the spatial atlas element. For example, the trajectory or the plurality of trajectories are described by means of a spatial transformation which acts on a spatial atlas element for changing the position and/or geometry of the spatial atlas element. For example, the dynamic property describes the time-dependent movement of a spatial atlas element by use of a single trajectory defining a position of the spatial atlas element depending on time (e.g. the position of the center of the spatial atlas element). For example, the dynamic property describes the time-dependent volumetric change of a spatial atlas element in terms of a total volume depending on time. For example, the dynamic property describes the time-dependent deformation of a spatial atlas element by defining a time-dependent transformation of the spatial properties of the spatial atlas element. For this purpose, a plurality of trajectories can be used as described above. In particular, the time-dependent deformation of an element can be defined by time-dependent positional changes of several points within the element. For example, point on the boundary of the element can be used. In case of an equal expansion of the element, all points on the boundary are moved in an outward direction. The more time-dependent positional changes of points are used, i.e. the more trajectories are used, the higher the resolution of the deformational change. In case all voxels of a spatial atlas element are assigned a separate trajectory, the resolution representing the volumetric change is optimized. In case only a few voxels of a spatial atlas element are assigned a separate trajectory, interpolation may be used to determine a deformed state of the spatial atlas element. Alternatively or additionally, the dynamic property may describe a correlation between a trajectory of the spatial atlas element in relation to another trajectory of a different spatial atlas element. Details on the trajectories and the correlation therebetween are given below including several mathematical formulae.

The information on the dynamic property for example is respectively linked to the spatial atlas elements. For example, this information is included in dynamic atlas data which is stored as meta data associated (linked) with the spatial atlas elements. Alternatively or additionally, this information is stored separately from the static atlas data and linked to the respective spatial atlas elements using links such as hyperlinks or a table including linking information, i.e. associating each of the information on the dynamic property to individual spatial atlas elements. "Respectively" in this context means that the information on the dynamic property is linked to individual spatial atlas elements, meaning that an individual spatial atlas element is associated with individual information on the dynamic property. For example, the information on the dynamic property is not linked to representational properties.

For example, for an individual atlas element, there is a bijective relationship between the spatial property related to this spatial atlas element and the dynamic data related to this spatial atlas element. For example, this bijectively linked relationship is given for some or for each single one of the individual spatial atlas elements. For example, the link and the storage of the spatial element data and the dynamic atlas data is such that, for an individual spatial atlas element (for example for each one thereof), both the dynamic properties and the spatial properties or only one thereof is extractable and further processable. This allows for instance the calculation of correlation of movements by merely loading the relevant dynamic properties using the dynamic atlas data only. The extraction is for example directly possible without performing an image analysis or an analysis of a sequence of images due to the storage of the dynamic atlas data separately from but linked with the spatial element data. "Separately" means for example at different storage locations (e.g. storage sections, for instance a header of a file) and that both information types (dynamic and spatial) are separated in different files and/or storage locations. For instance, the header of the file describes dynamic atlas data and the file describes spatial element data.

For example, this association is performed upon creating or improving the compartmentalized dynamic anatomic atlas as will be described below. The meaning that "information on a dynamic property is linked to a spatial atlas element" or "information on a dynamic property is linked to at least one of a plurality of spatial atlas elements" is meant to cover for example the following: First information on a first dynamic property and optionally second information on a second dynamic property is respectively linked to a respective one of the spatial atlas elements. This is meant to also cover the case where this link is performed not just for the respective one of the spatial atlas elements but also for a plurality or all of the spatial atlas elements. For example, a plurality of information on a plurality of (different) dynamic properties is respectively linked to the respective spatial atlas elements. That is, although singular form may be used in the claims and the description, this formulation also includes the meaning of "at least one", for example a plural, i.e. in case the claims or the description refer to a singular entity, they may well include a plurality of the entity.

The information on the dynamic property for example describes correlations between the dynamic properties of different ones of the spatial atlas elements. For example, the information on the first dynamic property of a first spatial atlas element describes a correlation between the first dynamic property of the first spatial atlas element and the first dynamic property of a second spatial atlas element. Each correlation for example describes a correlation between the (same, in the example "first") dynamic properties of two individual and different spatial atlas elements. In this case, for example, the information on the first dynamic property of a first spatial atlas element describes a plurality of correlations between the first dynamic property of the first spatial atlas element and the first dynamic properties of a plurality of other spatial atlas elements, for example all other spatial atlas elements. Furthermore "plurality of correlations" means that each one of the plurality of correlations describes a correlation between the first dynamic property of the first spatial atlas element and the first dynamic property of one of the plurality of other spatial atlas elements. If there is more than one dynamic property, the term "first" can be replaced by "second", "third" and so on depending on the number of dynamic properties. The information on the dynamic property for example describes correlations between the dynamic properties of different ones of the spatial atlas elements by describing correlations between trajectories of these spatial atlas elements contained in the information on the dynamic property. For example, the information on the dynamic property of a first spatial atlas element describes not only a trajectory of the first spatial atlas element, but also a correlation of this trajectory to a trajectory of a second spatial atlas element. Of course, more than one such correlation may be described by the information on the dynamic property, depending on the number of available trajectories. The correlations may be stored in form of a matrix, an array or else and may for example be stored as meta data associated with the spatial element data describing the first spatial atlas element or stored as described above. For instance, each entry in a first one of a plurality of lines of the 2D matrix describes one correlation to one other spatial atlas element with respect to a first dynamic property and the entries in a second line of the matrix do the same for a second dynamic property and so on.

The correlations, for example in the form of a matrix, can for example be averaged and/or normalized between different individuals (for example patients) and/or between different spatial atlas elements. For example, the information on the dynamic property describes correlations between the dynamic properties of a plurality of different ones of the spatial atlas elements, for example all different ones of the spatial atlas elements described by the spatial element data. The information on the dynamic property described above for a first anatomic spatial atlas element for example is determined (and for example stored in the compartmentalized dynamic anatomic atlas) for a plurality of spatial atlas elements or for each of the spatial atlas elements. The correlation may be determined upon creating or improving the compartmentalized dynamic anatomical atlas as will be described below. For example, the information on the dynamic property linked to a spatial atlas element contains at least one normalized trajectory. That is, the information on the dynamic property linked to a spatial atlas element may be defined by a trajectory which has been normalized.

As a correlation, for example the cross correlation between two trajectories of different spatial atlas elements P and Q is used. In this example, each trajectory may describe the position of a spatial atlas element depending on time, i.e. the dynamic property is defined by the respective trajectory. The trajectory is for example continuous, i.e. not interrupted, i.e. has the form of an analytical function. For example, the trajectory assigns certain values for each point in time. The trajectory may be generated by connecting (and for example by interpolating, e.g. using piecewise constant interpolation, linear interpolation, polynomial interpolation, spline interpolation or else) several positions of the spatial atlas element which differ from one another depending on time. For example, the positions are connected in a sequence corresponding to the point in time in ascending timely order. Interpolation might be used to smooth the connecting line of the positions and/or fill in voids (missing data points).

Of course, also other time-dependent spatial properties are possible which can be described as vectors $\vec{p}(t)$, $\vec{q}(t)$ (e.g. deformation). A plurality of such vectors may define the aforementioned trajectory. For example, values of two separate parameters x, y at a point in time t can be described by a vector $\vec{p_{x,y}}(t)$ which defines values x(t) and y(t). Several of these vectors $\vec{p}(t)$ may define a trajectory representing time-dependent changes of the values of the parameters x and y—in this case, the trajectory may lie in a plane defined by the first parameter x (e.g. position in a first direction such as anterior-posterior) and the second parameter y (e.g. position in a second direction such as cranial-caudal), wherein each point of the trajectory indicates an amount of the first parameter x and an amount of the second parameter y at a given point in time.

The first parameter x may describe the position in a first spatial direction, whereas the second parameter y may describe the position in a second spatial direction. A third parameter z may describe the position in a third spatial direction. In this case, a vector $\vec{p_{x,y,z}}(t)$ for example describes time-dependent values x(t) of the first, time-dependent values y(t) of the second and time-dependent values z(t) of the third parameter. Several of these vectors $\vec{p_{x,y,z}}(t)$ for different points in time $t_0, t_1, \ldots, t_n$ can be combined, forming a trajectory in four dimensions (thee spatial and one time dimension). As noted above, the trajectory can be interpolated for smoothing and for filling in voids (missing data points). That is, a trajectory can be a continuous analytical function. For example, the described trajectories are (e.g. continuous) functions assigning a certain spatial position (e.g. in two or three spatial dimensions) to a certain point in time or vice versa. The spatial position may be the position of a voxel or pixel of a spatial atlas element or may be the position of a certain point within, on or relative to the spatial atlas element. For instance, the spatial position may be the position of the center point of the spatial atlas element or of a point describing the origin of a coordinate system within which the spatial properties of the spatial atlas element are defined.

A trajectory can for example be described by global vectors including all values of the vector $\vec{p}(t)$ (e.g. $\vec{p_{x,y}}(t)$ or $\vec{p_{x,y,z}}(t)$) at several points in time (e.g. all point in time for which data is available). For example, the global vector $\vec{p_{glob}}$ comprises all vectors $\vec{p_{x,y,z}}(t)$ for (n+1) points in time: $\vec{p_{x,y,z}}(t_0)$, $\vec{p_{x,y,z}}(t_1), \ldots, \vec{p_{x,y}}(t_n)$ For example, all vector values are stored in the global vector as follows:

$$\vec{p_{glob}} = \{p_x(t_0), p_y(t_0), p_z(t_0), p_x(t_1), p_y(t_1), p_z(t_1), \ldots, p_x(t_n), p_y(t_n), p_z(t_n)\}.$$

For the generation of the compartmentalized dynamic anatomic atlas (see below), only closed trajectories might be used which alternatively or additionally exhibit a periodic temporal behavior. For example, the dynamic property is dynamic spatial information in the form of at least one trajectory, for example in case the dynamic spatial information comprises information on a change of position of a spatial atlas element and/or information on a change of geometry of a spatial atlas element.

To determine the correlation between two trajectories, for example a global vector $\vec{p_{glob}}$ describing the respective trajectory can be used. For example, a global vector $\vec{p_{glob,1}}$ describing a first trajectory and a global vector $\vec{p_{glob,2}}$ describing a second trajectory can be used to determine the correlation between the first and the second trajectory. The correlation between the first trajectory described by all values of $\vec{p}(t)$ and the second trajectory described by all values of $\vec{q}(t)$ can for example be determined as follows:

$$Corr = \frac{\int_{t=t_0}^{t=t_n}(\vec{p}(t) - \vec{p}(t_0))(\vec{q}(t) - \vec{q}(t_0))dt}{\sqrt{\int_{t=t_0}^{t=t_n}(\vec{p}(t) - \vec{p}(t_0))(\vec{p}(t) - \vec{p}(t_0)dt}\sqrt{\int_{t=t_0}^{t=t_n}(\vec{q}(t) - \vec{q}(t_0))(\vec{q}(t) - \vec{q}(t_0)dt}}.$$

Alternatively or additionally, a component-wise or weighted correlation may be used. For example, all correlations between all trajectories ($\vec{p}(t)$, $\vec{q}(t)$, $\vec{r}(t)$, $\vec{s}(t), \ldots$) of different spatial atlas elements (P, Q, R, S, ...) are calculated as a matrix (CM).

The direction Dir of each trajectory, for example of the trajectory described by all values of $\vec{p}(t)$ of spatial atlas element P, can also be calculated, for example as follows:

$$Dir = \frac{\vec{p}(t) - \vec{p}(t_0)}{\sqrt{\int_{t=t_0}^{t=t_n}(\vec{p}(t) - \vec{p}(t_0))(\vec{p}(t) - \vec{p}(t_0)dt}}$$

or $$Dir = \frac{\vec{p}(t_0)}{|\vec{p}(t_0)|}.$$

The direction Dir can for example be averaged and/or normalized and associated to and/or stored for the corresponding spatial atlas element. The direction Dir may not be a scalar and may therefore for example be back-transformed into the dynamic anatomical atlas before averaging and/or normalizing.

As noted above, the information on the dynamic property for example describes correlations between the dynamic properties of different ones of the spatial atlas elements. The dynamic properties of different ones of the spatial atlas elements may include a plurality of different types of dynamic properties. For example, the information on the dynamic property of a given spatial atlas element describes not only its trajectory, but also correlations to the trajectories of other spatial atlas elements. The dynamic properties may also comprise such correlations for other parameters such as relative positions or correlations between volumetric changes.

The information on the dynamic property for example describes at least one normalized dynamic property of at least one spatial atlas element. For example, the dynamic property of some or all spatial atlas elements is normalized between some or all of the spatial atlas elements, for example so that the dynamic property of some or all of the spatial atlas elements can be compared with the dynamic property of some or all spatial atlas elements. For example, the dynamic property of all spatial atlas elements is normalized between all spatial atlas elements. For example, the dynamic property of some of the spatial atlas elements is normalized between all spatial atlas elements. For example, the dynamic property of some of the spatial atlas elements is normalized between the some of the spatial atlas elements.

Alternatively or additionally, the dynamic property of some or all spatial atlas elements is normalized between different individuals, wherein information of the different individuals was used for creating and/or improving the compartmentalized dynamic anatomic atlas as will be described below. For example, the dynamic property of a patient element of a first group (class) of patients is normalized with respect to a common reference. As the common reference, a predetermined value and/or trajectory and/or vector and/or else defining a reference dynamic property can be used.

Alternatively or additionally, as the common reference, a certain patient element of each of the patients is used (e.g. a rib). In this example, the common reference is different among patients or patient groups (classes). For example, trajectories of a first patient element of all patients of a certain patient type (class) are normalized with respect to a common reference trajectory or parts thereof. For example, a maximum value of the common reference trajectory and/or a minimum value of the common reference trajectory are used as normalization values. For example, the trajectories of the first patient element of all patients of the certain type (class) are adjusted so as to have the same minimum and/or maximum values as defined by the normalization values. For example, at least one of the maximum and minimum values of the trajectories in a certain spatial direction may be used as the maximum and minimum values. Of course, other methods are possible for normalization. The normalization is e.g. performed to make the individual dynamic properties of different patients comparable with each other.

Normalization of other dynamic properties can for example be performed using a common reference as well. The common reference may be a predetermined vector and/or matrix and/or value(s) or may be the change of the spatial property of a certain patient element or part thereof, i.e. a dimensional change by expansion or contraction of an element. For example, the dynamic properties associated with several voxels are averaged to serve as a common reference.

The term normalization in this disclosure does not relate to the reduction of data to a kind of canonical form but relates to the normalization of values, vectors, matrices and/or trajectories. For the correlation and normalization of trajectories describing time-dependent movement, reference is also made to Annex A.

The information of the at least one dynamic property linked to a spatial atlas element is for example classified according to patient types. The patient types for example include one or more of patients with a certain disease, patients with a certain age, patients with a certain anatomical property (obese, missing organs, deformed organs etc.), patients with a certain gender or else. For example, the information on the at least one dynamic property linked to a spatial atlas element is classified according to patient types depending on information of individuals from different patient types, for example information on the at least one dynamic property of an anatomic body part of individuals from different patient types, for example the individuals from different patient types used upon creating and/or improving the compartmentalized dynamic anatomic atlas. In one example, the information on the dynamic property linked to a spatial atlas element is classified by classifying a trajectory according to patient types, wherein the trajectory is, as described above, contained in the information on the dynamic property linked to the spatial atlas element and for example defines the dynamic property.

For example, information on the dynamic property of first anatomical body parts of individuals of a certain age are determined upon creating and/or improving the compartmentalized dynamic anatomic atlas. The certain age is then for example associated with the information on the dynamic property of the first anatomical body parts. In case this information is used upon creating and/or improving the compartmentalized dynamic anatomic atlas, the information on the (at least one) dynamic property linked to a spatial atlas element is classified according to the patient type of the certain age.

The compartmentalized dynamic anatomic atlas for example comprises information on a distribution of at least one dynamic property. The distribution of the at least one dynamic property may describe a probability of a value or values of the at least one dynamic property and be contained in the information on this dynamic property. For example, the distribution describes a probability of a value of the at least one dynamic property for a certain patient type. That is, the compartmentalized dynamic anatomic atlas may comprise information on a distribution of a trajectory contained in the information on the dynamic property. In the case of trajectories, the distribution may provide a plurality of trajectories or a probability of a given trajectory. For example, in the case of trajectories describing movement in three-dimensional space, the distribution may provide a probability for a given spatial position for several or all points in time. For example, the distribution describes a value or values of the at least one dynamic property for healthy patients, for example a value of probability of a correlation between two trajectories of two anatomic body parts of a healthy patient. In this example, if the value of correlation between two trajectories of two anatomic body parts of a patient with a disease deviates from the value of correlation between the two trajectories of the two corresponding anatomic body parts of the healthy patient, the information on a distribution of the dynamic property can be used as an indicator whether the patient with a disease has a disease. In this example, it can be determined that the patient with a disease has a disease if the value of correlation between two trajectories of the two anatomic body parts of the patient with a disease has a probability for healthy patients below a certain threshold, which probability is described by the distribution of the dynamic property. The distribution may be determined upon creating and/or improving the compartmentalized dynamic anatomic atlas.

The distribution of at least one dynamic property may describe different probabilities of a value of the at least one dynamic property for different patient types (patient classes). The classification according to patient types mentioned earlier can be used for that purpose. For example, a first information on a dynamical property linked to a first spatial atlas element is classified into a first patient type and a second information on a dynamical property linked to the first spatial atlas element is classified into a second patient type. This means that a first and a second information on a dynamic property are linked to the one spatial atlas element, wherein these information on a dynamic property are classified into different patient types. Therefore, there may be one information on a dynamic property respectively linked to a first spatial atlas element for each one of the patient classes. This may also be the case for a plurality or for all of the spatial atlas elements.

For example, a first patient class representing healthy patients and a second patient class representing patients with lung cancer can be provided. As noted earlier, a dynamic property can be assigned to each of these classes. For example, the movement of lung parts or the diaphragm can be classified according to patient types. The information on a distribution of the at least one dynamic property, for example the movement of the lung parts or the diaphragm, can be used to further increase an error rate of classifying a patient into one of the patient classes based on the compartmentalized dynamic anatomic atlas. As noted above, a dynamic property of a patient can be compared with the distribution. Depending on the result of the comparison (i.e. exceed a certain probability threshold), the patient can be assigned to the correct patient class which works as an indicator for a disease of the patient. The distribution gives more reliable results than fixes values because not all patients in one patient class may exhibit the same amount of dynamic property, for example the same amount of movement of the lung parts. The distribution can therefore be used as a measure of probability of a patient to fall into one of the patient categories.

The compartmentalized dynamic anatomic atlas for example comprises a spatial atlas element divided, for example subdivided into (adjacent) spatial atlas sub-elements respectively linked with different information on a dynamic property while being assigned the same representational property. Patient elements and/or atlas elements described herein are for example spatially integral elements. For details on the assignment of a representational property to a spatial atlas element it is referred to Annex B which describes the generation of an "atlas image" which contains a "grey atlas element" (corresponding to the static atlas image which contains an atlas image element as described herein) using "atlas spatial information" (corresponding to the spatial element data described herein) and "element representation information" (corresponding to the element representation data described herein). In particular, Annex B describes the provision of a "determination rule" in order to determine an applicable "representation data set" (corresponding to the representation data sets described herein, which describe representational properties) which is to be assigned to a "white atlas element" (corresponding to the spatial atlas element described herein) to generate the "atlas image". For example, the different dynamic properties are of the same type of dynamic property but represent different values of the same type of dynamic property. For example, the spatial atlas element is subdivided into at least two spatial atlas sub-elements of the same tissue type (e.g. which have the same visual appearance in medical image data) and/or which are assigned the same representational property (which association is in one example stored together with the static atlas data but preferably determined as described in Annex B), wherein a first of the at least two spatial atlas sub-elements is respectively linked with a first information on a dynamic property of a particular type (e.g. a first trajectory) and a second of the at least two spatial atlas sub-elements is respectively linked with a second information on the same type of dynamic property (e.g. a second trajectory). For example, the second information (e.g. second trajectory) can be different from, for example are different from, the first information (e.g. first trajectory). That is, for example, the first and the second trajectory can be different, for example are different. Different types of the dynamic property for example include movement, deformation, or combinations thereof as noted above.

The invention also relates to a computer implemented data processing method comprising the step of acquiring the compartmentalized dynamic anatomic atlas.

The invention also relates to a computer implemented data processing method for generating (e.g. improving or generating from the scratch) the compartmentalized dynamic anatomic atlas.

The method for example comprises a step of acquiring static patient data describing a static patient image of a patient element. The static patient data may be medical image data, for example 3D CT image data, 3D MR image data, 2D X-ray image data or else. The static patient image may be an image of one or more patient elements. The patient element for example is an anatomical body part of the patient and/or a part of the patient with a similar tissue structure which is for example represented by the same intensity and/or gray value in an X-ray image. As noted below, the acquisition may comprise loading of the static patient data, for example from a storage medium. The static patient data may be obtained beforehand, i.e. the obtaining of the static patient data, for example using a medical imaging device, is for example not part of the method.

The method for example further comprises a step of acquiring, based on the static atlas data, a static atlas image of the spatial atlas elements. In the following, the static atlas image is also referred to as atlas image as is the case in Annex B. In the following, the static patient image is also referred to as patient image as is the case in Annex B. The atlas image comprising atlas image elements may be generated based on the separated entities of the "spatial element data" and the "element representation data" as described in Annex B in detail. Note that the "atlas spatial information" of Annex B is equal to the spatial element data described herein and the "element representation information" of Annex B is equal to the element representation data described herein. Annex B refers to the generation of an atlas image also as a generation of "grey atlas elements" based on the "white atlas elements" and a certain representation data set. A parameter set associated with a patient image (e.g. image modality) and described by patient image data may be used for the generation of the static atlas image to be matched with the static patient image as described in Annex B. For example, a 3D static atlas image such as a 3D CT or 3D MR image is generated based on the static atlas data and the parameter set. For example, a 2D static atlas image such as a 2D DRR image is generated based on the static atlas data and the parameter set. The static atlas image may also be generated solely on the basis of the static atlas data, i.e. without the use of the parameter set. For example, instead of the parameter set, a given (e.g. predetermined) association between at least one spatial atlas element and a representation data set can be used to generate at least one atlas image element which forms the static atlas image (e.g. together with other atlas image elements). For instance, instead of the predetermined association and instead of the parameter set of the patient image, a predetermined parameter set is used in the generation of the static atlas image. That is, the static atlas image can be generated in different ways, all of which are (for example at least partly or only) based on the static atlas data. The generated static atlas image represents one or more of the spatial atlas elements. Other medical image data may be generated as the static atlas image. For example, the static atlas image is generated considering a viewing angle of an imaging device used to obtain a static patient image, for example for the generation of the 2D DRR.

The method for example further comprises a step of acquiring information on a dynamic property of a patient element. The dynamic property is for example at least one of the change of a spatial property, like geometry and/or position of the patient element, i.e. a dynamic spatial property. The information on the dynamic property for example is respectively linked to the patient element, for example by means of patient data (mentioned in Annex B) which describe for example both the patient elements and the information on the dynamic property. The patient element for example is an anatomical body part of the patient, for example a segmented part in the static patient image, for example an anatomical body part having a certain tissue structure. The term "respectively" means that individual information on the dynamic property is linked to an individual patient element, for example different information on the dynamic property is linked to each of a plurality or all of the patient elements. For example, the information on the dynamic property is obtained from dynamic 3D data and/or a similarity image and/or a dynamic DRR as described which are described in detail in Annex A and respectively linked to different patient elements.

The method for example further includes a step of matching the static patient image with the static atlas image. The matching for example matches one or more of the patient elements included in the static patient image with one or more atlas image elements included in the static atlas image. The matching may comprise a step of adjusting the position of the static patient image with respect to the static atlas image, which step may be performed automatically or manually (e.g. adjustment performed by a user). For example, an automatic optimization of the position of the static patient image with respect to the static atlas image is performed. The matching may include image fusion, for example rigid and/or elastic image fusion and may be performed by a matching algorithm such as a rigid or an elastic image fusion algorithm. The matching is for example described by a transformation, for example by a transformation matrix, the transformation for example describing a transformation of a coordinate system of the static patient image to a coordinate system of the static atlas image. The coordinate system of the static patient image may be defined by the static patient data and the coordinate system of the static atlas image may be described by the static atlas data, for example as meta information included in the data. Details of the matching between a (e.g. generated) static atlas image and a patient image are also given in Annex B.

The method may further comprise a step of determining, based on the matching, a corresponding spatial atlas element corresponding to the patient element. To this end, for example, the correspondence part data can be used as described in Annex B. The correspondence part data may be determined as described in Annex B. Alternatively or additionally, the matched static patient image is segmented using a segmentation algorithm, for example into different patient elements which for example have different tissue structures (i.e. which have different tissue types and/or for example exhibit different representational properties which correspond to representational properties of different representation data sets). The positions of the different patient elements of the matched static patient image are for example compared with positions of atlas image elements of the matched static atlas image. Based on the matching, for example using the matching result, for example the transformation, and the determined position of each of the elements in the coordinate system of the static patient image and the known position of each of the atlas image elements in the coordinate system of the static atlas image, and/or the segmentation results (for example the degree of similarity between the size and/or shape of the patient elements with atlas image elements), a corresponding atlas image element is determined which corresponds to the patient element. This determination may be performed for a plurality of patient elements included in the static patient image. Thus, a matched patient element can be associated with a given spatial atlas element which was used to generate the atlas image element corresponding to (successfully matched to) the patient element. That is, a patient element matched to an atlas image element corresponds not only to the atlas image element, but also to the spatial atlas element used to generate this atlas image element.

The method may further comprise a step for generating (improving or creating from the scratch) the compartmentalized dynamic anatomic atlas. This step for example comprises determining, based on the information on the dynamic property linked to the patient element, the information on the dynamic property linked to the corresponding spatial atlas element. For example, the information on the dynamic property is newly linked to the corresponding spatial atlas element and/or the already linked information on the dynamic property is updated (e.g. averaged and/or overwritten). As a consequence of this step, information on the dynamic property is respectively linked to the corresponding spatial atlas element. This step can be performed for at least one spatial atlas element, for example a plurality of spatial atlas elements, using a plurality of corresponding patient elements and the information on the dynamic property respectively linked to the plurality of patient elements. In other words, dynamic information of a patient is used to enrich the compartmentalized anatomic atlas comprising static atlas data so that it comprises static and dynamic atlas data as described above.

For example, data of multiple (for example classified, see above) patients may be used in this process to generate the compartmentalized dynamic anatomic atlas. For example, the information on the dynamic property of a spatial atlas element (which is for example classified according to patient types) may be determined as an average (value) of information on the dynamic property of the corresponding patient element of a plurality of patients (for example a plurality of patients of a particular patient type).

For this purpose, one or more of an average, a weighted average, a median, a mean or a distribution of the information on the dynamic property may be determined based on the information on the dynamic property respectively linked to the corresponding patient element of each one of the plurality of patients. For example, one or more of an average, a weighted average, a median, a mean or a distribution of the (value(s) of) trajectories contained in the information on the dynamic property are determined. For example, a mean (average) trajectory is determined, for example using (e.g. weighted) averaging between a plurality of trajectories. Alternatively or additionally, the information on the dynamic property respectively linked to the corresponding patient element may be normalized before being stored or before being used as information on the dynamic property respectively linked to the spatial atlas element or before being determined as information on the dynamic property respectively linked to the spatial atlas element. The normalization may be performed as described above, for example using reference information, for example information on the dynamic property respectively linked to a reference structure of the patient.

Instead of acquiring the patient images, an anatomic atlas comprising several static atlas images describing spatial properties (positions, geometries etc.) of the spatial atlas elements at different points in time may be used. For example, the several static atlas images can be used to determine the trajectories and thereafter the correlations. In this case, no additional patient images are necessary. In other words, the patient image data can be replaced with atlas image data in case the atlas image data describes spatial properties of the spatial atlas elements at different points in time. With respect to such an atlas comprising static atlas images, which can for example be a universal atlas, it is referred to the chapter "Definitions" and to Annex B. That is, atlas images comprised in such a (static) anatomic atlas can be used to determine the information on the dynamic property instead of having to rely on a plurality of patient images. In the case of Annex B, a plurality of atlas images may be generated representing atlas elements at different points in time. Subsequently, these images can be used to determine the information on the dynamic property of these atlas elements. This is done in the same manner as matching a static atlas image to a static patient image, only that in this case, a first static atlas image is matched with a second static atlas image and the dynamic property is determined from (for example defined by) the determined matching transformation. The determined dynamic property can be used as the "information on dynamic property" in order to generate the compartmentalized dynamic anatomic atlas. For example, the determined matching transformation is used to define the trajectories mentioned above.

The method for example comprises a step of calculating correlations between the dynamic properties of different patient elements based on the information on the dynamic properties linked to different patient elements for determining the correlations between the dynamic properties of different ones of the spatial atlas elements described by the information on the dynamic property respectively linked to the spatial atlas elements. These correlations as well as the calculation thereof have been described above. For example, correlations between the dynamic property of a first patient element to dynamic properties (of the same type, e.g. positional change) of different patient elements are calculated. These correlations are thereafter determined as the correlations between the dynamic properties of the corresponding spatial atlas element (corresponding to the first patient element) and the different corresponding spatial atlas elements (corresponding to the different patient elements). The correlations are for example set and/or stored so as to be described by the information on the dynamic property respectively linked to the corresponding spatial atlas element. Consequently, a plurality of correlations may be stored for the corresponding spatial atlas element. This determination may be performed for a plurality or all off the patient elements to generate the dynamic atlas data comprised in the compartmentalized dynamic anatomic atlas.

Alternatively or additionally, based on at least the information on the dynamic property linked to a patient element at least one normalized dynamic property for the patient element is calculated for determining the at least one normalized dynamic property described above. For example, the dynamic property of some or all of the patient elements is normalized between some or all of the patient elements. The some of the patient elements are for example elements in a predetermined anatomical region (e.g. lung, abdomen, region defined by a predetermined distance from a reference element, . . . ) and/or elements which are influenced by the same physical mechanism (e.g. heartbeat, breathing motion, conscious movement, . . . ) which elements can be chosen based on first predetermined selection criteria and/or elements which are known to have comparable dynamic spatial properties (e.g. movement in a certain direction to a certain degree (movement amount below threshold), same cyclic phase of movement (same time constant of cyclic movement), same cyclic phase of change of other spatial properties such as volumetric change and others, . . . ) which elements can be chosen based on second predetermined criteria. Alternatively or additionally, the dynamic property of some or all of the patient elements is normalized between different patients. Alternatively or additionally, the dynamic property of some or all of the patient elements is normalized with respect to a reference structure.

For example, a reference structure is identified in each of a plurality of patients which is used as a normalization reference, wherein static patient data and dynamic patient data of each one of the plurality of patients is used to generate the compartmentalized dynamic anatomic atlas. As described above, the information on dynamic properties of patient elements of different patients can be averaged, weighted averaged or else to determine the information on dynamic properties of corresponding spatial atlas elements. The reference structure is for example identified in each of the patients which (static and dynamic) information are used to generate the compartmentalized dynamic anatomic atlas. The reference structure may differ amongst patient classes (for example amongst patient types).

For example, in case the dynamic property is dynamic spatial information in the form of at least one trajectory, a reference object with a reference trajectory is identified in each of the different individuals, for example a reference anatomical body part, for example a rib. The trajectories of other anatomical body parts are for example normalized for each of the different individuals using the individual reference trajectory (which may be different for each of the plurality of patients). Several normalization methods may be used for normalization. For example, a maximum and/or a minimum and/or average (e.g. mode, mean, median, weighted average) value of the reference trajectory are used as a reference for normalization, for example a maximum and/or minimum and/or average value of the reference trajectory in a particular direction (e.g. along the main axis or along a sub axis). For example, only closed loop trajectories, for example only cyclic (timely cyclic) trajectories are normalized. For example, the main axis (the amount of positional shift in the main axis) of a reference trajectory may be used to normalize one or more of the patient trajectories.

The normalization may be performed for patients of different patient types (classes) independently and/or differently. For example, the trajectories of patients of a first type (class) are normalized with respect to a first reference whilst the trajectories of patients of a second type (class) are normalized with respect to a second reference. For example, the first patient type defines patients with lung cancer whereas the second patient type defines healthy patients. For example, the first patient class defines patients who are older than a predetermined age, whereas the second patient class defines patients who are younger than the predetermined age.

The normalization may be performed for each patient individually. For example, the trajectories of each of the patients are normalized with respect to an individual reference. For example, the individual reference is a trajectory of a certain patient element of the individual patient (e.g. the rib). For example, the individual reference is a reference which serves as an indicator of a certain movement such as a breathing movement, a heartbeat or else. Since these movements (e.g. breathing movement) may affect other anatomic body parts of a patient (e.g. lung is displaced by breathing movement), the individual reference serving as an indicator of the movement (e.g. a rib) can be used for normalization of the trajectories of the other body parts (e.g. the lung) with respect to the movement (e.g. the breathing movement). This results in trajectories which are normalized with respect to a certain type of movement. That can for example make several trajectories of different patients which have all been normalized with respect to the same kind of movement (e.g. breathing movement) comparable, independent on the exact amount of movement which might differ greatly between patients (e.g. older patients breath less air per breathing cycle than mid-aged patients). With respect to the trajectories and the calculations based on these trajectories (normalization, correlation etc.), it is also referred to Annex A.

Alternatively or additionally, the information on the dynamic property of the plurality of patients may be normalized using a common reference such as a predetermined reference which is for example independent of each of the patients. For example, a predetermined multiplication (and/or division and/or addition and/or subtraction) factor (and/or vector or matrix) is used to normalize the information on the dynamic property of each of the plurality of patients.

Also, at least one threshold value may be used to determine which of the information on the dynamic property of the patient elements of the plurality of patients shall be used to generate the compartmentalized dynamic anatomic atlas. For example, information on the dynamic property exceeding a certain threshold may not be used for generating the compartmentalized dynamic anatomic atlas. For example, only closed loop movements (e.g. (timely cyclic) closed loop trajectories) are used for generating the dynamic atlas data.

The method for example comprises a step of determining spatial atlas sub-elements corresponding to dynamic subregions (subvolumes) exhibiting different dynamic properties, i.e. corresponding to patient sub-elements. A refinement of the atlas can be performed by dividing the spatial atlas elements into several spatial atlas sub-elements. This is of advantage if the corresponding patient sub-elements exhibit different dynamic properties and thus the spatial atlas sub-elements can be linked with different information on the dynamic property, i.e. with different trajectories. That is, the spatial atlas elements may be divided, for example subdivided, for example partitioned, for example tessellated into several spatial atlas sub-elements which exhibit different dynamic properties, i.e. which are linked with different information (e.g. different trajectories) on the same dynamic property (e.g. movement). For this purpose, patient images may be used. In a first step, corresponding spatial atlas elements which correspond to corresponding patient elements, for example, are determined by using the correspondence data, for example by matching a static atlas image with a patient image as described above or as described in Annex B. In a next step, the information on the dynamic property of the patient elements is determined using several patient images of the patient at different points in time. The different dynamic properties are for example a dynamic property of the same type, i.e. the different dynamic properties are different dynamic characteristics, e.g. values, directions or vectors of a certain dynamic property (e.g. different direction of the main axis of a cyclic trajectory or different volumetric changes described by a plurality of trajectories). For example, certain patient elements may comprise dynamic subregions (subvolumes) exhibiting different characteristics of a dynamic property. In this case, the certain patient elements are for example divided, for example subdivided into a plurality of patient sub-elements, wherein each sub-element exhibits a different dynamic property. The "different dynamic property" may correspond to a certain range of values of the dynamic property. The trajectories describing the movement and/or deformation of the sub-elements may differ from one another. In case the difference between the trajectories of two spatial objects within a patient element (e.g. areas within a patient element) exceeds a predetermined value (e.g. the correlation between the trajectories is lower than a predetermined value), these spatial objects (e.g. these areas within the patient element) can be determined as being sub-elements. Of course, this also applies to more than one such spatial object. The determination can be made for each voxel of a patient element as individual spatial object in order to determine whether there are any sub-elements within the patient element. The same division of patient elements into patient sub-elements can be applied to the corresponding spatial atlas elements resulting in corresponding spatial atlas sub-elements and thus, for example, resulting in corresponding spatial atlas sub-elements.

Similarly to the method described above with respect to the spatial atlas elements, the information on the dynamic property of each patient sub-element may be used to determine the information on the dynamic property of each corresponding spatial atlas sub-element. For example, the method comprises a step for generating (improving or creating from the scratch) the compartmentalized dynamic anatomic atlas by determining, based on the information on the dynamic property linked to the patient sub-elements, the information on the dynamic property linked to the corresponding spatial atlas sub-elements. For example, the same information on the dynamic property is linked to several patient sub-elements, i.e. depending on the resolution of the measurement method used to determine the information on the dynamic property. For example, several patient sub-elements may correspond to the same spatial atlas sub-element or vice versa. In this case, the information on the dynamic property of the several patient sub-elements may be combined (e.g. averaged (weighted, mode, mean, . . . )) to determine the information on the dynamic property of the corresponding spatial atlas sub-element or the information on the dynamic property of the patient sub-element may be determined as the information on the dynamic property of the corresponding several spatial atlas sub-elements.

The invention also relates to a computer implemented data processing method for enabling an analysis of an anatomic dynamic of a patient.

For example, the method comprises several steps as described above with reference to the method for generating the compartmentalized dynamic anatomic atlas: a step of acquiring the static atlas data and the dynamic atlas data of the dynamic atlas; a step of acquiring static patient data describing a static patient image of a patient element; a step of acquiring, based on the static atlas data, a static atlas image (the atlas image may be generated using the static atlas data—see above for details); a step of matching the static patient image with the static atlas image; a step of acquiring dynamic patient data comprising information on a dynamic property which information is respectively linked to the patient element; and a step of determining a corresponding spatial atlas element corresponding to the patient element for example based on the matching.

For enabling the analysis, the method comprises an additional step. This step for example includes comparing the information on the dynamic property linked to the corresponding spatial atlas element and the information on the dynamic property linked to the patient element. For example, the comparing includes calculating a correlation between the information on the dynamic property linked to the corresponding spatial atlas element and the information on the dynamic property linked to the patient element. For example, the comparing includes calculating correlations between predetermined trajectories classified according to patient types—which predetermined trajectories are linked to the corresponding spatial atlas element—and a trajectory comprised in the information on the dynamic property of the patient element. Of course, a plurality of trajectories of the patient element may be used in the comparing. For example, the comparing includes calculating a difference between values described by the two information, a correlation between trajectories or else. The comparing may include additional mathematical steps to compare the two information.

The method may further comprise a step of determining, based on the comparing (comparison) and based on the information on the distribution of the at least one dynamic property described above, whether the determined dynamic property of the corresponding patient element is within a predefined range or not. The predefined range may be a range of the distribution of the at least one dynamic property, for example determined by a threshold describing a minimal probability of a certain value of the dynamic property, wherein the probability of the certain value of the dynamic property is described by the distribution. For details on the distribution, see also above.

For example, the distribution of the at least one dynamic property may describe the distribution of values of the at least one dynamic property among the plurality of patients used to generate the dynamic atlas data. In case it is determined that the determined dynamic property of the corresponding patient element is within the predefined range it may be determined that the corresponding patient element exhibits a normal (healthy) behavior. In case it is determined that the determined dynamic property of the corresponding patient element is not within the predefined range, this may be used as an indicator for determining that the corresponding patient element exhibits an abnormal (unhealthy) behavior which can indicate the presence of a disease. Of course, this indication does not replace the judgement of a doctor or surgeon, i.e. this indication does not equal a diagnostic result.

The determination may be based on the classification of the at least one dynamic property. As described above, a separate distribution may be available for each of the patient types. In this example, it may be determined that the determined dynamic property of the corresponding patient element is not within the predefined range of a first patient type (which may be healthy) but is within the predefined range of a second patient type (which may have a particular disease). This determination may be used to determine the type of the patient and at the same time whether the corresponding patient element exhibits an abnormal (unhealthy) behavior or a normal (healthy) behavior.

The method may comprise a step of acquiring the static atlas data and the dynamic atlas data of the dynamic atlas. As a next step, the method for example includes comparing at least one dynamic property associated with a certain patient class (e.g. patient type) of the corresponding spatial atlas element with the dynamic property of the patient element. This comparison may be performed as described above and for example allows to determine for which patient class there is the highest similarity for one or more patient elements.

The method may further include a step of determining the type of the patient. For example, the dynamic property associated with the certain patient class (e.g. patient type) of the spatial atlas elements is used in this context. For example, a first degree of similarity between the dynamic property of the patient element and the dynamic property of the corresponding spatial atlas element which is associated with a first patient class is determined. For example, a second degree of similarity between the dynamic property of the patient element and the dynamic property of the corresponding spatial atlas element which is associated with a second patient class is determined. Depending on which degree of similarity is higher, the type of the patient can be determined. For example, in case the first degree of similarity is higher than the second degree of similarity, it is determined that the patient is classified into the first class, i.e. the patient type is a patient type corresponding to the first class.

The degree of similarity may be determined as described above with respect to the comparing, i.e. a difference in dynamic characteristics such as values and/or a correlation between values and/or trajectories or else is used as a measure of a degree of similarity. Alternatively or additionally, the aforementioned distribution may be used in this context for the assessment of similarity. For example, the dynamic property of the patient element is compared with the distribution of the dynamic property of the corresponding spatial atlas element which is associated with a first patient class. This may result in a first probability of the patient element to fall into the first patient class. For example, the dynamic property of the patient element is then compared with the distribution of the dynamic property of the corresponding spatial atlas element which is associated with a second patient class. This may result in a second probability of the patient element to fall into the second patient class. The first and the second probability may be used as a measure of similarity.

The types of a patient may for example include a type of breathing of the patient, for example indicating an amount of diaphragmatic, thoracic, clavicular and/or paradoxical breathing. The types of a patient may for example include a type of a certain pathological appearance or a type of a certain disease.

The invention also relates to a use of the compartmentalized dynamic anatomic atlas for matching a patient image and an atlas image. This use for example includes a step of using the information on the dynamic property of at least one spatial atlas element as a constraint for the matching. For example, the matching includes an image fusion.

For example, a patient image (e.g. a static patient image comprising only static image information) may be matched with an atlas image. In this case, a constraint for the matching may be defined by the dynamic property of a spatial atlas element. For example, it may be defined that the corresponding patient element must have a dynamic spatial property which lies within a certain range defined by the dynamic property of the corresponding spatial atlas element and a predetermined range threshold. For example, the location of a possibly corresponding patient element may be constrained to a certain area. For example, the positional change of a possibly corresponding patient element may be constrained to a certain amplitude, phase, direction, deviation from a given trajectory or else. For example, the volumetric change and/or deformation of a possibly corresponding patient element may be constrained to a certain maximum value, phase, deviation from a given rate or absolute value of (volumetric or deformational) change or else. In other words, static atlas data may be used for a matching, but in this example the dynamic atlas data is used in addition to the static atlas data for the matching in the form of a constraint, e.g. a constraint limiting the possible positions of a corresponding patient element (corresponding to a corresponding spatial atlas element).

For example, a patient image comprising static and dynamic information may be matched with an atlas image. In this case, a constraint for the matching may be that a certain spatial atlas element—used to generate a certain atlas image element which is to be matched with the patient element—exhibits a certain dynamic property which the corresponding patient element must also exhibit to a predetermined degree or to which the corresponding patient element must not be in contradiction.

For instance the dynamic property may describe a maximal change of geometry and/or position of an element in absolute terms or relative to other elements (e.g. maximum distance to another element during positional change caused by vital movements), which should not be violated by the matching (e.g. by image fusion). For example, in case the information on the dynamic property respectively linked to a spatial atlas element representing a rib describes a movement of max. 5 cm in z-direction, a constraint for the matching may be that the corresponding patient element is allowed to move max. 4-6 cm in z-direction, wherein this movement may be described by the information on the dynamic property respectively linked to the corresponding patient element.

Alternatively or additionally only spatial atlas elements exhibiting a certain degree of dynamic property such as a certain amount of movement are used as constraint for matching the patient image with an atlas image. For example, the atlas element which exhibits the least amount of movement (indicated by the information on the dynamic property respectively linked to the spatial atlas element) is used for the matching.

For example, the compartmentalized dynamic anatomic atlas is used for matching two patient images (with one another). To this end, the matching is for example coupled (coupled transformation) by means of the atlas as described in the chapter "Definitions", in particular in the aspects 1) to 10). For example, the information on the dynamic property of at least one spatial atlas element is used as a constraint for the matching of the two patient images. For example, the first patient image is an image representing a certain patient at a first point in time, whereas the second patient image is an image representing the certain patient at a second point in time which is different from the first point in time. For example, the second point in time is later than the first point in time. For example, each of the first and the second patient images includes at least one patient element such as an anatomical body part (e.g. bladder). For example, at least one particular patient element is included in both the first and the second patient image.

For example, a first patient image to be matched with a second patient image is in a first step matched with a static atlas image generated from the static atlas data of the compartmentalized dynamic anatomic atlas (see Annex B for details on the generation of a static atlas image using the static atlas data, which is referred to as determination of "atlas images" using "atlas data" in Annex B). For this matching, for example a spatial atlas element which information on the dynamic property indicates a low rate of movement and/or a low change in position, i.e. a dynamic property which lies below a predetermined threshold, is used (for example a vertebra which moves less than 1 mm according to the information on the dynamic property respectively linked to the vertebra as spatial atlas element).

For example, the corresponding patient elements (e.g. lung, bladder, ribs) and the corresponding atlas image elements and thus also the corresponding spatial atlas elements (e.g. lung, bladder, ribs) are identified in a second step following the first step, for example by using the correspondence part data described in Annex B. That is, because it is known which spatial atlas element corresponds to which atlas image element, it is possible to obtain a relation between a corresponding patient element matched to an atlas image element and a corresponding spatial atlas element. In particular, it is known which spatial atlas element corresponds to which atlas image element since the spatial atlas element is enriched with representational information to generate the atlas image element, whereby the static atlas image is generated (see Annex B for details on this generation; in Annex B, the static atlas image is referred to as "atlas image" and the static atlas data is referred to as "atlas data").

For example, the two patient images (the first patient image and the second patient image) are matched in a third step following the second step. For example, the information on the dynamic property (e.g. describing movement) respectively linked to one of the corresponding spatial atlas elements (e.g. bladder) is used as a constraint for matching the first patient image with the second patient image. For example, it can be determined that the positional difference between the corresponding patient element in the first patient image (e.g. bladder of the patient at the first point in time) and a patient element identified in the second image has to lie in a certain interval, for example be lower than a maximal positional deviation described by the information on the dynamic property of the corresponding patient element. In case this condition is not fulfilled, it can for example be determined that the patient element identified in the second patient image and used for matching the corresponding patient element of the first patient image is not the corresponding patient element of the second patient image (e.g. in case the patient element identified in the second patient image is a kidney whereas the corresponding patient element in the first patient image is the bladder). In this case, another patient element may be identified in the second patient image to be matched with the corresponding patient element of the first patient image (e.g. the bladder). Alternatively or additionally, a second corresponding patient element (e.g. a kidney) of the first patient image may be determined which fulfills the constraint for the matching with respect to the patient element of the second patient image (e.g. the kidney). Of course, other kinds of dynamic properties can be used as constraint for the matching instead of the maximal positional deviation, for example direction of movement, rate of movement, phase of movement, correlation between trajectories or else.

The compartmentalized dynamic anatomic atlas can for example be used by acquiring the static atlas data and the dynamic atlas data. In a next step, static patient data describing a static patient image of a patient element may be acquired. In a next step, based on the static atlas data a static atlas image is acquired. Note that the static atlas data may be used to generate the static atlas image including atlas image elements, possibly also using the static patient data (see Annex B which refers to the static atlas data as "atlas data" and to the static atlas image as "atlas image"; the static patient image is referred to as "patient image" in Annex B). In a next step, the static patient image may be matched with the static atlas image. A corresponding spatial atlas element corresponding to the patient element may be determined based on the matching. In particular, a corresponding atlas image element which matches the corresponding patient element may be determined. Since it is known which spatial atlas element underlies the corresponding atlas image element, the corresponding spatial atlas element which corresponds to the corresponding patient element can be determined without much effort.

The use of the compartmentalized dynamic anatomic atlas may further comprise a step of determining patient sub-elements within the patient element based on the spatial atlas sub-elements of the corresponding spatial atlas element. For example, the position and/or shape of the corresponding spatial atlas sub-elements (corresponding to the patient element) are determined in coordinates of the static atlas image. These coordinates may be transformed into the coordinates of the static patient image based on the matching result, i.e. based on the (matching) transformation (matrix). Subsequently, the position and/or shape of sub-elements within the patient element may be determined based on the transformed coordinates.

The dynamic property is a dynamic spatial property like for example dynamic spatial information. The dynamic spatial information for example comprises information on a change of position (movement) of an object (e.g. described by a trajectory) and/or information on a change of geometry (deformation) of an object. All of the aforementioned dynamic information may describe time-dependent, i.e. dynamic, spatial properties of an object. The object is at least one of the patient element or a patient sub-element or one of the spatial atlas element or a spatial atlas sub-element.

The invention also relates to a computer program which, when running on at least one processor of at least one computer or when loaded into the memory of at least one computer, causes the at least one computer to perform the aforementioned method, or a signal wave, for example a digital signal wave, carrying information which represents the program. It also relates to a non-transitory computer-readable program storage medium on which the aforementioned program is stored. It also relates to least one computer, comprising at least one processor and a memory, wherein the aforementioned program is running on the at least one processor or is loaded into the memory, or wherein the at least one computer comprises the aforementioned program storage medium.

Definitions

In this section, definitions for specific terminology used in this disclosure are offered which also form part of the present disclosure.

A universal atlas can for example be generated by a data processing method for determining data which are referred to as atlas data and comprise information on a description of an image of a general anatomical structure, wherein this image is referred to as the atlas image, the method comprising the following steps performed by a computer:
  acquiring patient data which comprise a description of a set of images of an anatomical structure of a set of patients, wherein the images are referred to as patient images and each patient image is associated with a parameter set which comprises one or more parameters given when the patient images are generated, wherein the parameters influence representations of anatomical elements as expressed by image values in the patient images, the patient data comprising the patient image set and the parameter sets associated with the patient image set;
  acquiring model data which comprise information on a description of an image of a model of an anatomical structure of a patient which is referred to as the model image and is associated with the parameter set;
  wherein the model of an anatomical structure is referred to as the model structure and comprises a model of at least one anatomical element which is referred to as model element;
  wherein the model data comprise:
    model spatial information on a description of the spatial information on the model structure; and
    model element representation information on a description of a plurality of representation data sets which contain information on representations of the at least one model element in the model images to be generated and are referred to as model representation data sets, wherein the model element representation information also describes a determination rule for determining out of the plurality of representation data sets respective model representation data sets for one or more respective model elements in accordance with respective parameter sets, the representation data sets do not include spatial information relating to the at least one model element;
  wherein acquiring the model data involves generating, on the basis of the model data and the patient data, the set of model images which respectively represent at least a part of the model structure by using the spatial information on the model structure and particular model representation data sets which are determined by applying the determination rule in accordance with the one or more associated parameter sets and at least one particular model element referred to as corresponding model element, which is to be matched to at least one corresponding anatomical element represented in the patient image and referred to as patient element;
  determining matching transformations which are referred to as PM transformations and which are constituted to respectively match the set of patient images of the set of patients to the set of model images by matching images associated with the same parameter set;
  determining an inverse average transformation by applying an inverting and averaging operation to the determined PM transformations; and determining the atlas data by:
    applying the determined inverse average transformation to the model data; or
    respectively applying the determined PM transformations to the respective patient images in order to determine matched patient images, averaging the matched patient images in order to determine an average matched patient image, and determining the atlas data by applying the determined inverse average transformation to the average matched patient image. One property of the universal atlas is for example that the spatial information (e.g. positions and/or geometry) and the representation information (e.g. grey values) are stored separately. This separation is described in Annex B in detail, which refers to atlas spatial information and element representation information, respectively. For further details on the generation of the universal atlas, it is also referred to PCT/EP2013/072005 published as WO 2014/064063.

Matching by the universal atlas (e.g. using the universal atlas) can for example be performed using the method according to one of the following aspects 1) to 10). In particular, aspects 4) to 7) concern the matching between several patient images of different modalities using the universal atlas.

Aspect 1) A data processing method for determining a matching transformation for matching a set of one or more images of an anatomical body structure of a patient, referred to as a patient image set, and a set of one or more images of a general anatomical structure, referred to as an atlas image set, wherein the general anatomical structure comprises a plurality of anatomical elements referred to as atlas elements, and each patient image is associated with one of a plurality of different parameter sets, wherein the parameter sets comprise one or more parameters which obtain when the patient images are generated, and the parameters influence representations of anatomical elements in the patient images, the method comprising the following steps performed by a computer:

acquiring atlas data, comprising the sub-steps of
acquiring atlas spatial information which contains spatial information on the general anatomical structure, and
acquiring element representation information which describes a plurality of representation data sets, wherein the element representation information further describes a determination rule for determining out of the plurality of representation data sets respective representation data sets for respective atlas elements in accordance with different respective parameter sets, the representation data sets containing information on representations of the plurality of atlas elements in the atlas images to be generated but not containing the spatial information on the general anatomical structure;

acquiring patient data, comprising the sub-steps of
acquiring the patient image set, and
acquiring one or more of the plurality of parameter sets which are respectively associated with the one or more images of the patient image set;

generating, on the basis of the atlas data and the patient data, the set of atlas images which respectively represent at least a part of the general anatomical structure by using the spatial information on the general anatomical structure and particular representation data sets which are determined by applying the determination rule in accordance with the one or more associated parameter sets and particular atlas elements acquired and referred to as corresponding elements, which are to be matched to corresponding anatomical elements represented in the patient image;

determining the matching transformation which matches the atlas image set and the patient image set, by matching images associated with the same parameter set to each other.

Aspect 2) The data processing method according to aspect 1), wherein determining the atlas image set involves:
determining the representation data sets for the corresponding elements, wherein for each atlas image to be determined, one of the representation data sets is determined for each of the corresponding elements in accordance with the determination rule, wherein the determination rule comprises an assignment rule for assigning a respective representation data set to a respective corresponding element in accordance with the parameter set associated with the patient image to which the atlas image which includes the corresponding element is to be matched; and
determining the atlas image set comprising one or more images which are respectively associated with one of the parameter sets, by respectively using the determined representation data sets to determine the representations of the corresponding elements.

Aspect 3) The data processing method according to any one of the preceding aspects, wherein in order to determine the representation of one or more of the corresponding elements in the one or more atlas images, image values of patient elements are used in combination with determining the matching transformation.

Aspect 4) The data processing method according to any one of the preceding aspects, wherein the step of determining the matching transformation, which matches one of the atlas images and one of the patient images associated with one of the parameter sets to each other, is configured such that the matching transformation is determined on the basis of information on the matching transformation between another of the atlas images and another of the patient images associated with another of the associated parameter sets.

Aspect 5) The data processing method according to any one of the preceding aspects, wherein the matching transformation is designed to deform a part of the geometry of the general anatomical structure in order to match the atlas images to the patient images, and wherein determining the matching transformation involves taking into account information on the influence on matching quality of a deformation of at least one of the atlas images associated with at least one of the parameter sets in order to determine the deformation of at least another of the atlas images which is associated with at least another of the parameter sets and includes corresponding elements which are identical to the corresponding elements included in said at least one of the atlas images.

Aspect 6) The data processing method according to the preceding aspect, wherein determining the matching transformation involves taking into account the fact that the spatial information described by the atlas images is identical and also taking into account information on the spatial correlation between the spatial information described by the patient images in order to determine deformations described by the matching transformation which is applied in order to match the atlas images and patient images to each other.

Aspect 7) The data processing method according to any one of the preceding aspects, wherein the matching transformation comprises a set of coupled transformations referred to as matching sub-transformations, wherein the respective matching sub-transformations respectively match the atlas images associated with one of the associated parameter sets and the patient image which is associated with the same respective associated parameter set to each other, and the matching sub-transformations are coupled in that they each influence the determination of the other.

Aspect 8) The data processing method according to any one of the preceding aspects, wherein the determination rule describes an assignment between the plurality of atlas elements and the plurality of representation data sets by describing a surjective assignment between the atlas elements and representation classes, wherein the respective representation classes respectively represent subsets of the plurality of representation data sets, and wherein for each of the respective representation classes, there is a unique set of characteristic bijective assignments between individual representation data sets of the subsets and individual parameter sets.

Aspect 9) The data processing method according to any one of the preceding aspects, wherein the representation data sets describe at least one of the following types of information on representation: image values for the anatomical elements; ranges of image values for the anatomical elements; the relationship between image values of different anatomical elements; the relationship between image values for one or more of the anatomical elements represented in images associated with different parameter sets; maximum image values for the anatomical elements; minimum image values for the anatomical elements; average image values for the anatomical elements; standard deviations of the average image values and structures of modulations of the image values for the anatomical elements; characteristics of transitions between representations of different anatomical elements.

Aspect 10) The data processing method according to any one of the preceding aspects, wherein the atlas data also comprise spatial flexibility information which describes a flexibility of the position of atlas elements within the general anatomical structure, and wherein the matching transformation is determined on the basis of the spatial flexibility information.

For further details on the aspects 1) to 10) relating to the matching using the universal atlas it is also referred to PCT/EP2012/071241 published as WO 2014/063746.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumor represents an example of a change in an anatomical structure. If the tumor grows, it may then be said to represent an expanded anatomical structure. This expanded anatomical structure may not be detectable; for example, only a part of the expanded anatomical structure may be detectable. Primary/high-grade brain tumors are for example usually visible on MRI scans when contrast agents are used to infiltrate the tumor. MRI scans represent an example of an imaging method. In the case of MRI scans of such brain tumors, the signal enhancement in the MRI images (due to the contrast agents infiltrating the tumor) is considered to represent the solid tumor mass. Thus, the tumor is detectable and for example discernible in the image generated by the imaging method. In addition to these tumors, referred to as "enhancing" tumors, it is thought that approximately 10% of brain tumors are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimization algorithms are applied in order to find the transformation which results in an optimum degree of similarity. The degree of similarity is preferably measured by way of a measure of similarity (also referred to in the following as a "similarity measure"). The parameters of the optimization algorithm are for example vectors of a deformation field. These vectors are determined by the optimization algorithm in such a way as to result in an optimum degree of similarity. Thus, the optimum degree of similarity represents a condition, for example a constraint, for the optimization algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimizing problem is for example solved iteratively, for example by means of an optimization algorithm which is for example a first-order optimization algorithm, such as a gradient descent algorithm. Other examples of optimization algorithms include optimization algorithms which do not use derivations, such as the downhill simplex algorithm, or algorithms which use higher-order derivatives such as Newton-like algorithms. The optimization algorithm preferably performs a local optimization. If there is a plurality of local optima, global algorithms such as simulated annealing or generic algorithms can be used. In the case of linear optimization problems, the simplex method can for instance be used.

In the steps of the optimization algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighboring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity. A measure of similarity can for example be determined on the basis of a determined correlation between the first and second datasets.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 15A-15D show the steps of the data processing method according to one embodiment of Annex B.

Any number of element representation data sets RDS, spatial element data describing spatial atlas elements SAA "information on dynamic property" mentioned below are just an example of the term "plurality". FIG. 1 is a diagram showing the basic components of the compartmentalized dynamic anatomic atlas 1. The compartmentalized dynamic anatomic atlas 1 comprises static atlas data 2 and dynamic atlas data 3. The static atlas data 2 comprises spatial element data 2b and element representation data 2a.

The spatial element data 2b comprises spatial information data sets. In FIG. 1, each of the spatial information data is represented by a rectangular box and comprises information on spatial properties of one spatial atlas element SAA. The spatial properties of spatial atlas elements SAA 4a, 4b, 4c, 4d are contained in the four different spatial information data sets depicted by the surrounding boxes. The number four is just an example for "plurality". The spatial properties include for example a position and/or geometry of a spatial anatomical element. The spatial properties do not include any information about representational properties of the spatial atlas element. For that reason, the spatial atlas elements are also referred to as "white atlas elements" in Annex B. That is, the spatial properties described by the spatial data sets for example only include spatial information, i.e. information about spatial properties.

Figures 1, 2:
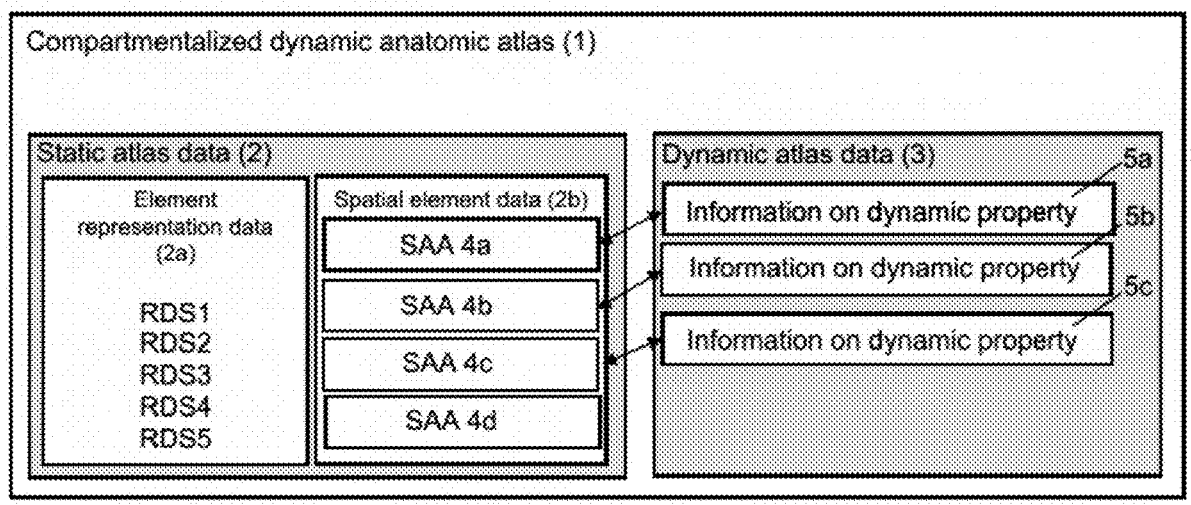
FIG. 1 is a diagram showing the basic components of the disclosed dynamic atlas.
FIG. 2 is a diagram showing an example of the information on the dynamic property.

The element representation data 2a is separated from the spatial element data 2b but is also included in the static atlas data 2. That is, the spatial element data 2b is—as is the case for the spatial element data 2a—not time-dependent, but static. Note that the static atlas data corresponds to the "atlas data" described in Annex B.

The element representation data 2a comprises five representation data sets RDS1 to RDS 5. The number five is just an example for "plurality". Each of the representation data sets RDS1 to RDS5 describes representational properties assignable to spatial atlas elements (e.g. SAA 4a to 4d) in order to generate corresponding atlas image elements. The representation data sets RDS1 to RDS5 may be clustered into different representation classes as described in Annex B in detail. For example, the representation classes may represent different tissue types. For example, the representation data set RDS1 contains a list which assigns grey values to different parameter sets. The parameter sets may comprise image modalities, tissue types, an ID of a set of spatial information or else. Both the spatial element data 2b and the element representation data 2a have to be used to generate a static atlas image comprising atlas image elements. The generation of such a generation of a static atlas image is described in Annex B in detail, wherein the static atlas image is referred to as "atlas image", the static atlas data is referred to as "atlas data", the spatial element data is referred to as "atlas spatial information" and the element representation data is referred to as "element representation information". As described in Annex B in detail, rules are used to determine which representational property is to be assigned to a given spatial atlas element. Afterwards, an atlas image element can be generated based on the spatial properties of the spatial atlas element and the assigned representational property. This results in a static atlas image comprising one or more atlas image elements.

The dynamic atlas data 3 comprises information on a dynamic property 5a, 5b, 5c which information is respectively linked to the spatial atlas elements 4a, 4b, 4c. In the example shown in FIG. 1, spatial properties of four different spatial atlas elements 4a, 4b, 4c, 4d are described by four different spatial information data sets in the static atlas data 2. The spatial atlas elements 4a, 4b, 4c, 4d in this example represent a first rib, a diaphragm, a heart, and a second rib. The information on the dynamic property 5a, 5b, 5c in this example is information on the movement of an anatomical structure described by a (closed loop) trajectory. The three different information on the dynamic property 5a, 5b, 5c shown in FIG. 1 correspond to a trajectory of the spatial atlas element 4a (e.g. the first rib), a trajectory of the spatial atlas element 4b (e.g. the diaphragm) and a trajectory of the spatial atlas element 4c (e.g. the heart), each of which is associated with the corresponding spatial atlas element 4a, 4b, 4c in the compartmentalized dynamic anatomic atlas 1. In this example, the information on the dynamic property 5a, 5b, 5c is stored as meta data associated with the corresponding spatial atlas element 4a, 4b, 4c. In the example, since each of the spatial information data sets only contains information on spatial properties of a single spatial atlas element, the information on the dynamic property 5a, 5b, 5c may alternatively or additionally be associated with the spatial information data sets. As noted in the general description, other and/or additional dynamical (time-dependent) spatial properties may be described by the information on the dynamic property. Also, correlations between the dynamic property of a first spatial atlas element and the dynamic property of at least one other spatial atlas element may be stored as information on the dynamic property respectively linked to the first spatial atlas element.

In the example, there is no information on the dynamic property respectively linked to spatial atlas element 4d. This means that the compartmentalized dynamic anatomic atlas 1 shown in FIG. 1 comprises static atlas data 2 describing spatial atlas elements (namely 4a, 4b and 4c) and dynamic atlas data 3 comprising information on a dynamic property (namely 5a, 5b and 5c) which information is respectively linked to the spatial atlas elements (namely 4a, 4b and 4c).

FIG. 2 is a diagram showing an example of the information on the dynamic property. The example of FIG. 2 shows the information on the dynamic property 5a described by the dynamic atlas data 3, wherein the information on the dynamic property 5a is respectively linked to the spatial atlas element 4a described by the respective spatial information data set comprised in the static atlas data 2. In this example, the information on the dynamic property Sa is represented as a matrix. Correlations between several different types of dynamical properties are described by the information on the dynamic property, namely a correlation of (movement) trajectories (first line in the matrix of FIG. 2) and a correlation of volumetric change (second line in the matrix of FIG. 2).

The correlation in the first line, first column of the matrix is a correlation between the trajectory of the spatial atlas element 4a (e.g. the first rib) and the trajectory of the spatial atlas element 4b (e.g. the diaphragm). The correlation in the first line, second column of the matrix is a correlation between the trajectory of the spatial atlas element 4a (e.g. the first rib) and the trajectory of the spatial atlas element 4c (e.g. the heart). The correlation in the first line, third column of the matrix is a correlation between the trajectory of the spatial atlas element 4a (e.g. the first rib) and the trajectory of the spatial atlas element 4d (e.g. the second rib). In the shown example, a numerical value (in the example: 5, 1 and 9) as well as an indicator (in the example: "medium", "low" and "high") of the respective correlation is stored. Other parameters may be stored for each of the correlations (e.g. a value indicating correlation of the trajectories in a certain spatial direction, a difference of maximum or minimum values of the trajectories (for example in a certain spatial direction) etc.), for example measures of similarity of the trajectories.

The correlation in the second line, first column of the matrix is a correlation between the volumetric change of the spatial atlas element 4a (e.g. the first rib) and the volumetric change of the spatial atlas element 4b (e.g. the diaphragm). The correlation in the second line, second column of the matrix is a correlation between the volumetric change of the spatial atlas element 4a (e.g. the first rib) and the volumetric change of the spatial atlas element 4c (e.g. the heart). The correlation in the second line, third column of the matrix is a correlation between the volumetric change of the spatial atlas element 4a (e.g. the first rib) and the volumetric change of the spatial atlas element 4d (e.g. the second rib). In the shown example, a numerical value (in the example: 52, 8 and 97) as well as an indicator (in the example: "medium", "low" and "high") of the respective correlation is stored. Other parameters may be stored for each of the correlations (e.g. a value indicating correlation of the volumetric changes in a certain time range, a value indicating correlation of the rise in volume, a value indication correlation of the decrease of volume etc.). Note that volumetric changes may be described by a plurality of trajectories, for example a plurality of trajectories which described the time-dependent shift of the outline of a spatial anatomical element. In this case, several trajectories may be compared with corresponding trajectories of another spatial atlas element, for example six trajectories describing the positional changes of the outermost part of the spatial anatomical element in anterior direction, posterior direction, caudal direction, cranial direction, right direction and left direction. Volumetric changes may also be represented by an absolute volumetric value which depends on time.

Figure 3:
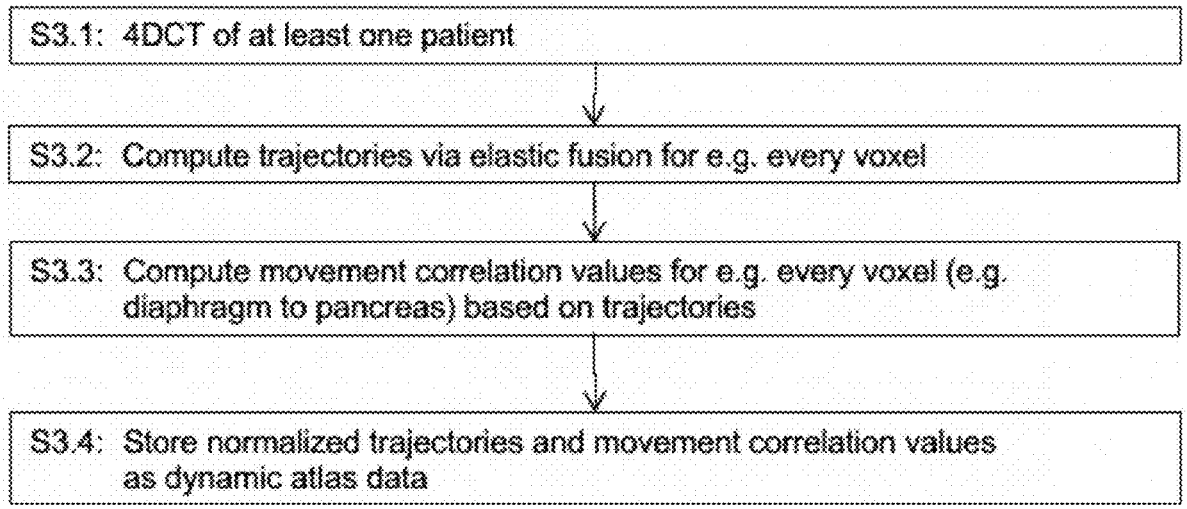
FIG. 3 shows a first sequence of steps of a specific embodiment of the disclosed method.
Figure 4:
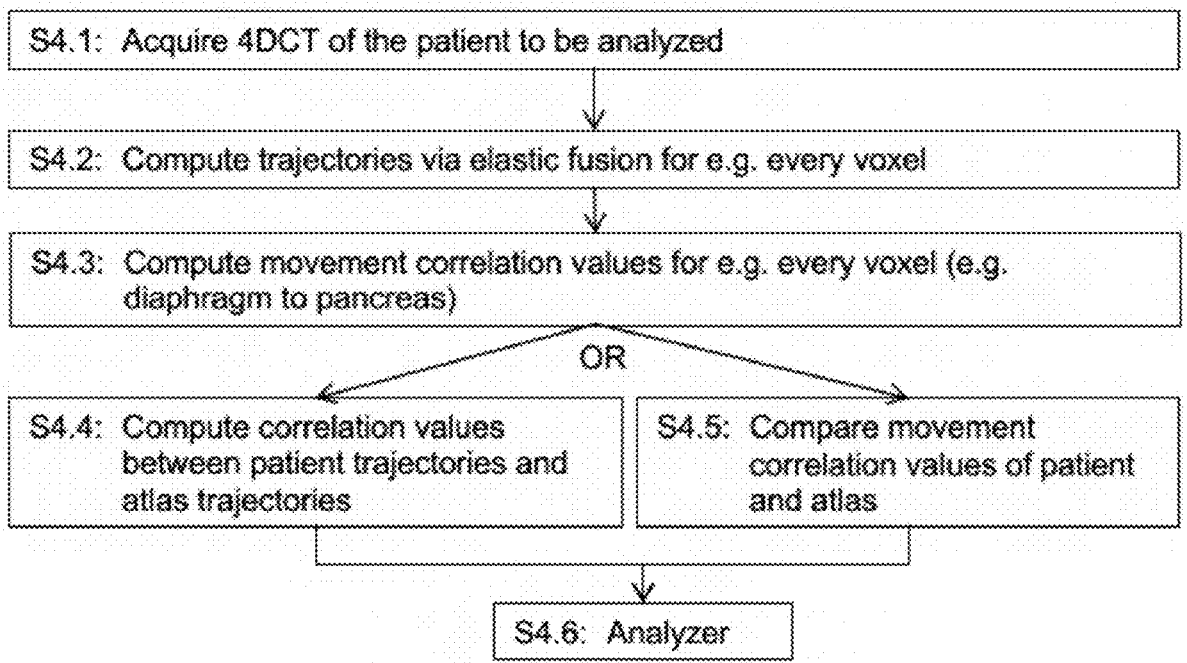
FIG. 4 shows a second sequence of steps of a specific embodiment of the disclosed method.

FIG. 3 shows a first sequence of steps of a specific embodiment of the disclosed method. It should be noted that one or more of the method steps shown in FIGS. 3 and 4 can be performed at the same time or subsequently, some of the steps may be replaced or omitted and additional and/or alternative steps may be used, wherever possible. In other words, the sequence of steps shown in FIGS. 3 and 4 is not the only embodiment covered by this disclosure.

The method concerns the generation, improvement and/or enrichment of the compartmentalized dynamic anatomic atlas, in particular the generation of the information on the dynamic property. The depicted method comprises several steps S3.1 to S3.4. It should be noted that other and/or alternative and/or additional steps can be used to generate the information on the dynamic property. For instance, several (f)MRT images may be used to determine the change concentration of oxygen in certain elements and/or the change of shape and/or geometry of patient elements.

In the first exemplary step S3.1, a 4DCT of at least one patient is acquired (e.g. loaded into a computer). Of course, other imaging modalities are possible as long as image data is acquired in step S3.1 which represents the patient at different points in time. For example, a 4DCT scan can be used which includes several 3DCT scans and information on their timely sequence (timely dependencies). For example, several 3DCTs can be acquired which represent the patient at different points in time. These can be combined into a 4DCT.

In the next exemplary step S3.2, a group of voxels or each individual voxel of a first 3D CT data set (e.g. acquired and/or generated in step S3.1) is matched with a corresponding group of voxels or a corresponding individual voxel of a second 3D CT data set which represents an image of the patient at a different point in time than the first 3D CT data set. Elastic fusion may be used for the matching. This step may be repeated with several image data representing the patient at further different points in time. Consequently, the position of the group of voxels or of the individual voxel depending on the point in time can be determined. Connecting all the determined positions results in a (e.g. closed-loop) trajectory which describes the time-dependent movement of the group of voxels or of each individual voxel.

In the next exemplary step S3.3, movement correlation values are calculated, for example for each individual voxel for which a trajectory has been determined (e.g. in step S3.2). The movement correlation values may be determined by forming a correlation of a first trajectory of a first voxel with a second trajectory of a second voxel. For example, a plurality of movement correlation values of a first trajectory of a first voxel with respect to other trajectories of several (or all) other voxels are determined.

In the next exemplary step S3.4, the trajectories are normalized. For example, the trajectories are normalized with respect to a reference trajectory. For example, a first plurality of trajectories of a first plurality of voxels are normalized in a different way (other reference, other normalization method, . . . ) than a second plurality of trajectories of a second plurality of voxels. For example, all voxels which are part of a first anatomical body part are normalized in the same manner. Different anatomical body parts may be determined by matching one of the plurality of patient images with a static atlas image generated using the static atlas data or by a user. For example, normalization is performed so that each patient element (representing an anatomical body part of the patient) is associated with a certain trajectory and certain movement correlation values (e.g. by averaging the trajectories of all voxels within the patient element).

After normalization, the normalized trajectories and the movement correlation values (e.g. determined in step S3.3) which are associated with a certain patient element are stored as dynamic atlas data 3 in the compartmentalized dynamic anatomic atlas 1. For this purpose, the normalized trajectories and the movement correlation values should be respectively linked to the individual spatial atlas elements. Therefore, at least one of the patient images used to obtain the normalized trajectories is matched with a static atlas image. Image fusion may be used to determine a corresponding patient element which corresponds to a corresponding atlas image element which is part of the static atlas image. Afterwards, the information on the dynamic property (e.g. 5a) of the corresponding patient element (the information for example comprising the normalized trajectory and the (normalized) movement correlation values, e.g. the trajectory of a rib) is stored in the compartmentalized dynamic anatomic atlas 1 respectively linked with the corresponding spatial atlas element (e.g. the spatial atlas element 4a representing the rib). The corresponding spatial atlas element may be determined by using the correspondence part data mentioned in Annex B, for example it is known since it was used in generating the matched atlas image element, for example it was chosen by a user. This results in the compartmentalized dynamic anatomic atlas 1 shown in FIG. 1. Details on the generation of the trajectories using the 4D-CT are given in Annex A, whereas details on the generation and structure of the static atlas data are given in Annex B, which refers to "atlas data" instead of static atlas data.

FIG. 4 shows a second sequence of steps of a specific embodiment of the disclosed method. For example, the method includes one or more of the steps shown in FIG. 3 (S3.1 to S3.4) and continues with one of the steps shown in FIG. 4. For example, the compartmentalized dynamic anatomic atlas 1 has already been created (is available), and the method starts with step S4.1. In exemplary step S4.1, a 4DCT of a patient to be analyzed is acquired (e.g. loaded into a computer). As noted above, alternative imaging modalities may be used as long as they include information on a time-dependent behavior of the patient, e.g. a series of patient images representing the patient at different points in time.

In the next exemplary step S4.2, information of the dynamic properties is determined, i.e. trajectories are calculated for each or some of the voxels of the patient image (e.g. acquired in step S4.3). The (closed-loop and/or cyclic) trajectories may be calculated as described above with respect to step S3.2 and may describe the time-dependent position of a voxel or of a group of voxels.

In exemplary step S4.3, movement correlation values are calculated for every voxel or for some of the voxels or for the groups of voxels. For example, several or all of the trajectories of voxels which are part of a patient element are normalized (e.g. averaged and normalized with respect to a normalization trajectory or a given normalization value). Then, for (each of) the patient element(s), a trajectory is determined. Subsequently, movement correlation values can be determined between different patient elements, e.g. using the determined trajectories of the different patient elements.

That is, correlations between different trajectories may be used as movement correlation values (as described above with respect to step S3.3).

In a next exemplary step S4.4, correlation values between patient trajectories and atlas trajectories are computed (e.g. determined or calculated). For this purpose, only the trajectories are needed which means that step S4.4 can directly follow step S4.3. For example, a correlation between the trajectory of a corresponding patient element and the trajectory of a corresponding spatial atlas element is determined. As noted earlier with respect to FIG. 3, to identify the corresponding patient and spatial atlas elements, a patient image used to generate the trajectories can be matched (e.g. via image fusion) with a static atlas image generated using the static atlas data. Alternatively or additionally to step S4.4, step S4.5 may be performed.

In exemplary step S4.5, the movement correlation values of the patient and of the atlas are compared. For example, the movement correlation values of a corresponding patient element are compared with the movement correlation value of the corresponding spatial atlas element. The comparison may include mathematical functions such as subtraction, division, addition, multiplication, differentiation, integration, a combination thereof or else. As a result of the comparison, a certain numerical value may be determined. For example, the correlation value of movement of a first patient element to the movement of a second patient element is compared with the correlation value of movement of a first spatial atlas element to the movement of a second spatial atlas element, wherein the first patient element corresponds to the first spatial atlas element and the second patient element corresponds to the second spatial atlas element. Instead of the second patient element and the second spatial atlas element, a reference element may be used, i.e. a reference movement is compared with the movements of the first patient element and the first spatial atlas element to determine two correlation values which can then be compared. Also in these cases, the movement may be described by a trajectory as noted above.

Following step S4.4 and/or step S4.5, the correlation values determined in step S4.4 and/or the comparison result determined in step S4.5 are input into an analyzer in exemplary step S4.6. The analyzer uses one or both of the aforementioned data to determine a degree of similarity between the patient and the atlas, for example between the dynamic property of the corresponding patient element and the dynamic property of the corresponding spatial atlas element. This analysis may be used to classify the patient according to a certain patient type. Alternatively and/or additionally, this analysis may be used as an indicator for a certain disease (e.g. in case a certain patient element moves different compared with a corresponding spatial atlas element, i.e. in case of a tumor which is attached to an anatomical element which moves differently). Other ways of using the comparison between the dynamic property of one or more patient elements and the dynamic property of the one or more corresponding spatial atlas elements are also possible, for example as laid out in the general description above.

Figure 5:
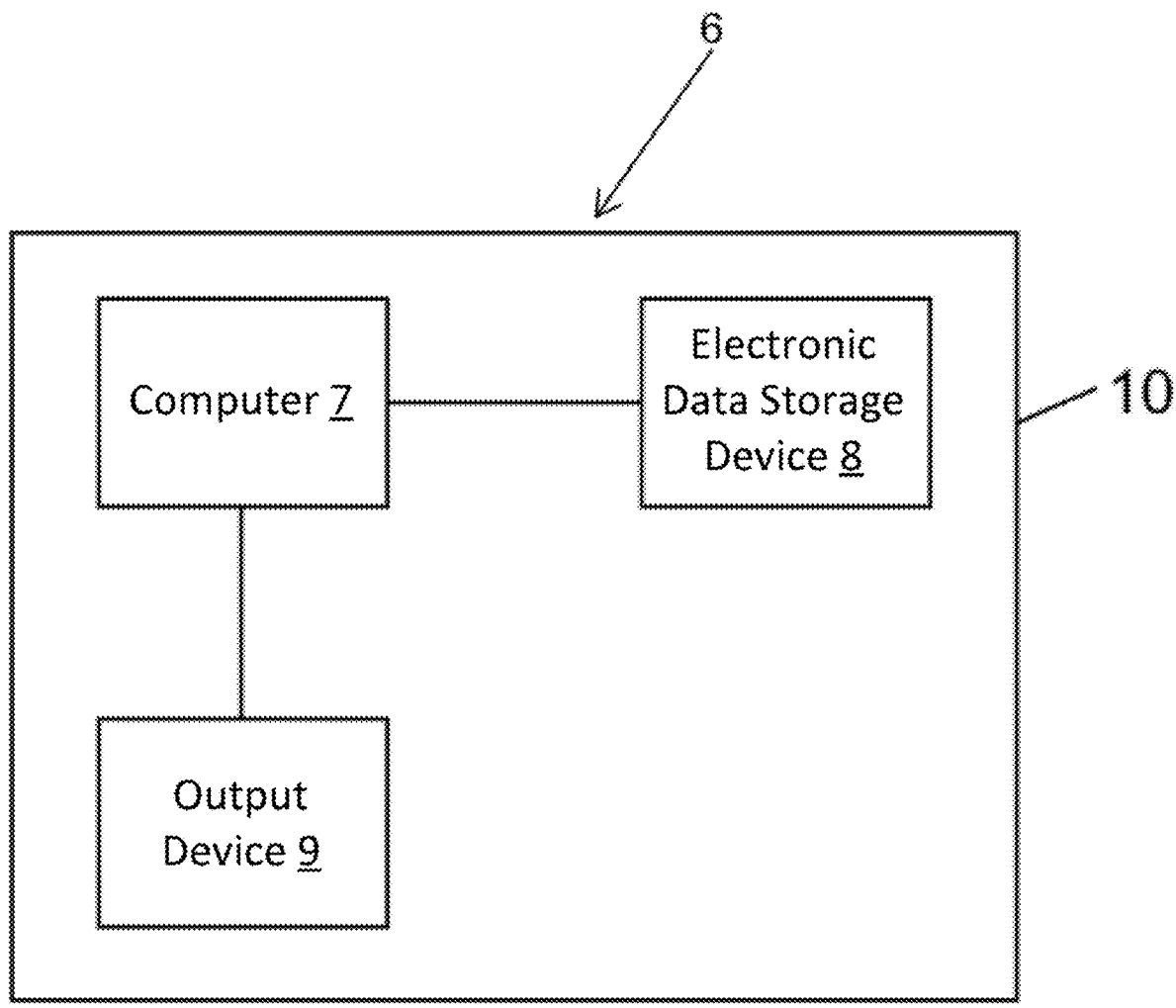
FIG. 5 shows a principle configuration of a system of a specific embodiment of the invention.

FIG. 5 shows a principle configuration of a system of a specific embodiment of the invention: the system 6 comprises a computing environment 10 including at least one computer 7 having at least one digital electronic processor which is operably coupled to at least one electronic data storage device 8 and an output device 9 (e.g. a graphical output device such as a display). The electronic data storage device 8 stores at least medical image data, the compartmentalized dynamic anatomic atlas 1 or a program. The computer 7 is configured to output, to the output device 9, electronic signals representing a (graphical) representation of a result of the data processing conducted by the computer 7. Furthermore, the computing environment 10 can be coupled to other devices such as a patient positioning device, a patient treatment device (for example a radiotherapy and/or radiosurgery device), one or more medical imaging devices (imagers), other computing systems such as a cloud-based computing system or else.

According to an exemplary embodiment, based on elastically fused 4D CTs specific points of a base CT can be transferred into CTs of different breathing phases, i.e. CTs of the patient describing the patient at different points in time. The transferring results in different positions of the specific points in each of the images, which can be represented by a (closed) trajectory in space. The target is now to find out, which trajectories are correlated in a specific patient, i.e. which points behave similar under breathing. And for comparison it might be interesting to know which points in a human body normally correlate. A general correlation map is preferably generated in atlas space, stored as meta information of a universal atlas.

But the averaging of meta information is challenging since the information, which is used for averaging, must be comparable between different patients independent of their breathing behavior. The information should therefore be normalized. The first step for an averaged correlation representation is to choose a set of points between which the correlation should be calculated. It can be done for every voxel or just for every organ or part(s) of an organ. For this purpose, the human body, i.e. of the universal atlas, could be divided into a plurality of cells. A point (e.g. at the center) of each cell might thereafter be identified as a reference for the individual cell. A number of 4D CTs of different individuals, which must be registered to the atlas (and or elastically fused to each other inside a 4D CT series) are required to create the dynamic atlas data. Then, the center points can be transformed (e.g. projected and/or matched) to the different data sets of the 4D CT series. For each 4D CT series and each center point a trajectory can be obtained with points $p_i$ (i=1 to n). An appropriate normalized correlation measure is e.g. the cross correlation between two trajectories p and q (or component-wise or weighted). All correlations between all center point trajectories corr ($cell_k$, $cell_j$) can be calculated as a huge matrix. This matrix can be averaged between different individuals and stored per cell pair as meta information in the atlas. The direction of each trajectory can also be calculated. This direction can also be averaged and stored per cell. The direction is not a scalar. It must be back-transformed into the atlas before averaging.

Annex A

One aspect of Annex A relates to the digital reconstructing (also called "rendering") of three-dimensional x-ray images (CTs) into two-dimensional images. Those two-dimensional images are referred to as in the art as DRRs. The DRR represents a simulated two-dimensional x-ray under the precondition of a particular (assumed) imaging geometry. The definition of imaging geometry is given below. For example, the rendering is performed so that the particular imaging geometry corresponds to the imaging geometry of at least one (for example one or two) monitoring x-ray device (for generating two dimensional x-ray images) which is used for monitoring a position of a patient in order to place a patient for radiotherapy or radiosurgery in accordance with a plan (for example based on a planning CT). For example, an isocenter of the radiotherapy or radiosurgery device and/or an isocenter of the planning CT and/or an isocenter of the particular imaging geometry and/or and isocenter of the at least one monitoring x-ray device are identical.

For example, in the medical field of radiotherapy or radiosurgery (in the following, and in an unlimiting manner the term "radiotherapy" is used only, but has to be understood to cover at least one of radiotherapy or radiosurgery), CTs are used for planning a radiotherapeutic treatment of a patient (for example to treat the targets, for example tumors). The CTs used for planning a radiotherapeutic treatment are referred to in the art as "planning CTs". Planning CTs are used to position the patient during the radiotherapeutic treatment. The radiotherapeutic treatment uses ionizing radiation (particles and/or electromagnetic waves) which are energetic enough to detach electrons from atoms or molecules inside the body and so ionize them. The treatment radiation is for example used in radiotherapy, for example in the field of oncology. For the treatment of cancer in particular, the parts of the body comprising a tumor (which is an example for a "treatment body part") are treated using the ionizing radiation. Since the body and in particular the treatment body part can be moved during positioning of the patient for radiation treatment or during the radiation treatment, it is advantageous to control the position of the treatment beam such that the treatment beam hits the treatment body parts as accurately as possible.

The movements of the treatment body parts are in particular due to movements which are referred to in the following as "vital movements". Reference is made in this respect to the European patent applications EP 0816422 and EP 09161530 as well as EP 10707504 which discuss these vital movements in detail.

In order to determine the position of the treatment body part, analytical devices such as x-ray devices, CT devices, and CBCT devices are used to generate analytical images of the body. The analytical devices are in particular devices for analyzing a body of a patient, for instance by using waves and/or radiation and/or beams of energy in particular electromagnetic waves and/or radiation and/or ultrasound waves and/or particle beams. The analytical devices are in particular devices which generate the above-mentioned two or three-dimensional images of the body of the patient (in particular of anatomical body parts) by analyzing the body.

However, it can be difficult to identify the treatment body part within the analytical image (for instance two-dimensional x-ray image). To this end, the above-mentioned DRRs which are generated from a planning CT in a usual manner are used by an operator to identify the treatment body part in a two-dimensional x-ray image. To this end for instance the (usual) DRR is overlaid over an x-ray image generated when the patient is placed for treatment by means of the ionizing radiation or the DRR is placed aside the two dimensional x-ray image on a display.

According to exemplary embodiments described in Annex A, there is at least one "primary anatomical element". This at least one primary anatomical element corresponds for example to a treatment body part (e.g. tumor) or to one or more other anatomical elements (for example secondary anatomic elements). For example, the one or more other anatomical elements are anatomic elements which undergo a vital movement. For example, the other anatomical element is the heart, diaphragm, or rip cage or part thereof. For example, the at least one primary anatomic element is an anatomic element which is represented by at least one voxel (for example cluster of voxels) in for example the undynamic CT or planning CT. The at least one primary anatomical element undergoes particular vital movements. The primary anatomical element can be identified by an operator (for example physician or physicist) in an undynamic CT or in a planning CT. Other anatomical elements, in particular the reminder of anatomical elements shown in the undynamic CT or the planning CT are referred to herein as secondary anatomic elements. Those secondary anatomical elements can or cannot undergo vital movements or can or cannot undergo the same vital movements as the primary anatomical elements. According to at least one exemplary embodiment, an anatomical atlas is used for segmentation of the undynamic CT or the planning CT to identify at least one of primary and secondary anatomical elements. According to at least one exemplary embodiment, an anatomical atlas is used for segmentation of the undynamic CT or the planning CT to segments unlikely to undergo vital movements and to exclude those segments (elements) from a determination of trajectories (see below) in order to save processing time and/or to make the determination of the dynamic DRR more robust. For example, a vertebral column could be identified to be not subjected to vital movements and corresponding image elements of the 4D-CT could be excluded from the determination of the trajectory similarity values as described below.

According to an exemplary embodiment, the primary anatomical element is represented by at least one voxel, usually a cluster of voxels in the planning CT. The term "a primary anatomical element" does not exclude that there is more than one anatomical element but covers the expression "at least one primary anatomical element". If there is more than one primary anatomical element than those undergo the same vital movements according to an exemplary embodiment. If there is more than one primary anatomical element those are for example distinct, i.e. separated by secondary anatomical elements. According to an exemplary embodiment, there are more than one primary anatomical element and for example the more than one primary anatomical elements are represented by a plurality of imaging elements in the planning CT or 4D-CT. For example, at least some of which are adjacent. For example, at least some of which are distinct.

Acquisition of Basic Data

According to at least one exemplary embodiment, 4D-CT data (short "4D-CT") are acquired. The 4D-CT represents a sequence of three-dimensional medical computer tomographic images (sequence of CTs) of an anatomical body part of a patient. The respective three-dimensional images (CTs) of the sequence for example represent the anatomical body part at different points in time. For example, the anatomical body part adopts different positions during a vital movement (e.g. caused by breathing and/or heartbeat). For instance, each CT (also referred to as "volume" or "bin" in the art) corresponds to a specific respiratory state which can be described as percentages of the fully inhaled or fully exhaled state of the patient.

For example, a plurality of different respiratory states are described by the sequence, for example, at least three, for example at least five different respiratory states are respectively described by at least one CT (bin).

For example, the extremes of the cyclic movement (for instance maximum inhalation and/or maximum exhalation) are respectively described by one CT of the sequence.

As mentioned above, one advantage of the exemplary embodiments described herein is that additional information can be provided (for example to an operator) which allows for a better interpretation and/or analysis of the CT and/or the two dimensional x-rays generated for monitoring the position of the patient. According to at least one exemplary embodiment, one of the CTs (bins) of the sequence or a CT determined by interpolation between two CTs defines the planning CT. For example, the interpolation represents a state of the body part intermediate between two neighboring states (respectively described by a sequence CT) which are subsequently adopted by the body part which undergoes the vital movement (for example cyclic movement).

For example, if the 4D-CT does not define the planning CT (e.g. in that one of the CT of the sequence is the planning CT or in that an interpolation of at least two of the CTs of the sequence defines the planning CT), then the planning CT is acquired separately.

Determination of Trajectory Similarity Values

In the following, the determination of trajectory similarity values is described. This determination based on the 4D-CT represents in itself a separate exemplary embodiment which can be supplemented by other steps of other exemplary embodiments (for example a step of displaying the trajectory similarity values) or the determination of the trajectory similarity values of image elements is embedded in at least one exemplary embodiment as described herein.

According to at least one exemplary embodiment a three-dimensional image is acquired from the 4D-CT. The acquisition of the image can for instance be done by selecting one of the CTs (bins) of the sequence defined by the 4D-CT or by determining a three-dimensional image by means of interpolation (as described above) from the 4D-CT. These three dimensional image is referred undynamic CT and for example comprises at least one first image element representing the primary anatomical element. For instance, a plurality of voxels of the undynamic CTs (for instance a cluster of voxels) represents the primary anatomical element (for instance target). For example, only one voxel represents a particular one of the at least one primary anatomical element, for example only one primary anatomical element. The second image elements represent the secondary anatomical elements. For example, the undynamic CT is selected by an operator from the sequence CTs to be that one in which a tumor is best discernable. An example for determining a CT suitable for tumor identification and for positioning the patient is given in the following application: WO 2015/127970. According to at least one exemplary embodiment, the undynamic CT is used to determine trajectories. A trajectory which describes the path of a first image element and is referred to as "primary trajectory". A primary trajectory describes the path of the first image element as a function of time. For example, the trajectory describes the path defined by positions of the first image element for different points in time which the first image element adopts in different sequence CTs. The different points in time correspond to different states of the cyclic movement (vital movement) of the primary anatomical element (for instance target). For example, the primary trajectory describes in a representative manner the trajectory of more than one first image element as described below.

According to an exemplary embodiment, one of the first image elements in the undynamic CT is defined to correspond to the isocenter of the planning CT. For example, this first image element (which is for example one voxel or more voxels) is referred to as reference image element and used to determine a primary trajectory referred to as reference primary trajectory which describes the path of the reference image element. for this one image element. The reference primary trajectory can be used for calculation of the trajectory similarity value as explained below.

According to a further exemplary embodiment, the reference image element is defined to be that one which is the center of mass of the at least one primary anatomical element (for example center of mass of tumor). Thus, the reference primary trajectory is the trajectory of the center of mass. According to a further exemplary embodiment, the center of mass and the isocenter are identical.

According to a further exemplary embodiment, the reference primary trajectory can be acquired by determining a plurality of trajectories each one describing a trajectory of one or more of the at least one first image elements. Thus, a plurality of trajectories are determined which represent the movement of more than one first image element which represent the at least one primary anatomical element. Then the reference primary trajectory is determined by averaging the plurality of trajectories. The averaging can be performed by different mathematical methods, for instance by at least one of mean or mode or median or by weighing particular trajectories (for instance by weighing a trajectory which represents the center of the primary anatomical element (for instance calculated by means of "center of mass" calculation where each voxel is assumed to have the same weight) or the isocenter of the planned radiation treatment) or a combination of the aforementioned methods.

The secondary trajectories respectively describe the trajectory of at least one second image element. For example, a second trajectory may describe the trajectory of only one image element or the second trajectory may describe the trajectory of a plurality (e.g. cluster) of second image elements. The determination of the first and second image elements can in particular be performed by segmentation of the undynamic CT by using an anatomical atlas. For example, image elements are excluded from trajectory determination which are part of an anatomical segment (determined by means of an atlas) which is known to do not undergo vital movements.

According to an exemplary embodiment, the aforementioned at least one primary trajectory and the secondary trajectories are used for determining the trajectory similarity values. The trajectory similarity values respectively describe a similarity between the primary and secondary trajectories. The trajectory similarity value describes in particular a similarity in positional changes of the trajectories (for example correlation, for example correlation coefficient) and/or a similarity of amplitude of cyclic movement (for example similarity of absolute maximum and/or minimum amplitude of the cyclic movement described by the compared trajectories).

According to at least one exemplary embodiment, a respective trajectory similarity value describes a similarity between a respective one of the second trajectories and one of the at least one primary trajectories (which is for example the reference primary trajectory) and/or between a respective one of the at least one primary trajectory and one of the at least one primary trajectories (which is for example the reference primary trajectory).

The trajectory similarity value is for example calculated by using the sum of squared differences (or for example an absolute value function) for each coordinate in which the trajectories is described. The sum of square of differences (or for example absolute value function) can be weighed in dependence on the coordinate. For example, the coordinate system is an orthogonal coordinate system. For example, one or more of the axes of the coordinate system are chosen to be directed along a major movement direction of the vital movement, for example inferior-superior or anterior-posterior. For example, the axes of the coordinate system are the main axes of a three dimensional surface (for example surface of a rotational ellipsoid), the surface being spanned by at least one of the trajectories, for example the reference primary trajectory which describes a cycling movement. For example, the main axes of the rotational ellipsoid can represent the axes of the coordinate system. For example, one of the minuend and subtrahend of the squared difference describes a deviation of a position one of the (primary or secondary) trajectory adopts at a particular point in time (that is the position of an image element (for example a first or second image element)) from an average position the trajectory adopts for the particular point in time (the point in time being within the time covered by the sequence described by the 4D-CT). For example, the average position is determined for one of the coordinate axes and averaged over all points in time (of the sequence). For example, the other one of the minuend and subtrahend of the squared difference describes a position which is adopted by one of the primary trajectories, for example by the reference primary trajectory. Thus, the squared difference is a measure for deviation along an axis. Any other function being a measure for such a deviation and the result of which is independent from an algebraic sign, like the absolute value function, can be used.

The similarity values can also be calculated by using a calculation of correlation coefficients which are for example a measure of the similarity of the trajectories.

The similarity measure (described by the trajectory similarity values) describes for example a similarity of the trajectories which describes for example a similarity of the movement of the image elements described by the trajectories.

The trajectory similarity values can be normalized. The trajectory similarity values can be a function of the peak to peak amplitude. According to exemplary embodiment, the trajectory similarity value describes at least one of the following: the similarity of the movement (e.g. described by correlation coefficient or sum of square differences) or the similarity of the amplitude (for instance peak to peak amplitude) described by the trajectories or the frequency of the cyclic movements described by the trajectories. Details of examples of the calculation of the trajectory similarity value are given below in the description of the detailed exemplary embodiments. According to an exemplary embodiment, the trajectory similarity value describes at least the correlation of the paths of the trajectories and/or of the movements described by the trajectories. According to an exemplary embodiment, for each of the secondary trajectories, the trajectory similarity value is calculated which describes for each of the secondary trajectories the correlation between the secondary trajectory and at least one of the at least one primary trajectory, for example reference primary trajectory. According to an exemplary embodiment, the trajectory similarity value determined in dependence on the correlation coefficient is additional a function of the similarity of the amplitude and/or similarity of the frequency. The function comprises in particular a threshold function. According to an exemplary embodiment, image values of a particular image element of the dynamic DRR are determined as a function of the trajectory similarity values. For example, image values are set to black level (lowest brightness) during rendering of the DRR if all trajectory similarity values related to the image values of all image elements used for rendering the particular image element are lower than a threshold value. According to another exemplary embodiment image values of image elements of a planning CT are disregarded (for example by setting them to black level) during rendering of the dynamic DRR if the trajectory similarity value related to the image values of the image used for rendering (for example planning CT or dynamic planning CT) is lower than a threshold value or are changed in color value, for example set to lower brightness than before or changed in color, for example set to a particular color (for example red). According to another exemplary embodiment image elements of a dynamic planning CT are set to black level if the trajectory similarity value related to them is lower than a threshold value or are changed in color value, for example set to lower brightness than before or changed in color, for example set to a particular color (for example red). According to another exemplary embodiment image values of the similarity image or the transformed similarity image are set to black level if the trajectory similarity value related to them is lower than a threshold value or are changed in color value, for example set to lower brightness than before or changed in color, for example set to a particular color (for example red). For example, image values related to trajectory similarity values above a predetermined threshold remain unchanged are not influence by the trajectory similarity values, and remain for example unchanged during determination of the dynamic DRR or their color value is changed, for example are set to higher brightness than before or changed in color (for example hue or saturation), for example set to a particular color (for example green), for example color different from that color set in case of below threshold value.

Determination of the Dynamic DRR

The trajectory similarity values determined as described above are preferably used to determine the dynamic DRR. According to at least one exemplary embodiment, the dynamic DRR is designed to reflect dynamic information on the movements (for example relative movement and/or amplitude and/or frequency) described by the at least one primary trajectories (for example reference primary trajectory) and the secondary trajectories, for example the movement relative to each other, the information being reflected in at least some of the image elements of the dynamic DRR and reflect information of movement related to image elements used for rendering the dynamic DRR. According to at least one embodiment, the dynamic DRR reflects information on the dynamics of anatomic elements in relationship to the dynamics of the at least one primary anatomic element. The information on dynamics (e.g. vital movement) is included in the dynamic DRR which is helpful for identification of the at least one primary anatomic data elements (for example helpful for more reliable target identification) in for example, the dynamic DRR and/or the dynamic CT and/or the similarity image. The information on dynamics helps for an identification of secondary anatomic elements having similar (for example same) vital movements as the at least one primary anatomic element (for example target), in addition to or alternatively to an identification of the at least one primary anatomic element. For example, those secondary anatomic elements identified in the dynamic DRR having similar (for example same) vital movement as the at least one primary anatomic elements are used for positioning a patient (for example for radio therapeutic treatment) for example relative to a beam arrangement (for example treatment beam).

If for example the least one primary anatomic element is an anatomic element other than a treatment body part, like for example the heart or diaphragm or rip cage or part thereof, the dynamic DRR and/or the dynamic CT and/or the similarity image allows to identify secondary anatomic elements having similar (for example same) movement dynamics (for example undergo the same vital movements), for example move in the same way as the heart or diaphragm or rip cage or part thereof.

According to at least one exemplary embodiment, the trajectory similarity values describe information on the dynamics, for example movements (for example relative movement and/or amplitude of (cyclic) movement and/or frequency of (cyclic) movement) described by the at least one primary trajectories (for example reference primary trajectory) and the secondary trajectories, for example information on the dynamics, for example movement (for example relative movement and/or amplitude of (cyclic) movement and/or frequency of (cyclic) movement) relative to each other, for example information on the similarity of the dynamics (for example movements) described by the at least one primary trajectories relative to the secondary trajectories.

If the 4D-CT does not define the planning CT but the planning CT is acquired independently, then preferably a transformation (referred to as "planning transformation") from the undynamic CT to the planning CT is determined and used for determining the dynamic DRR. According to at least one exemplary embodiment, at least a part of the image values of the image elements of the dynamic DRR is determined in dependence on the trajectory similarity values. The dynamic DRRs can be calculated as known in the art. That is, a particular imaging geometry can be defined. This imaging geometry is for instance defined by the position of an x-ray source and an x-ray detector. For instance, the imaginary rays of the x-ray source pass through a imaginary three-dimensional anatomical body part defined by the planning CT or the dynamic planning CT. According to at least one exemplary embodiment, the transmission properties of the image elements (for example voxels) are for example described by Hounsfield units and are for example defined by the brightness of the respective voxels. According to at least one exemplary embodiment, the trajectory similarity values assigned to the respective image elements (e.g. voxels or clusters thereof) of the three-dimensional image have an influence on the virtual absorption properties of the virtual three-dimensional anatomical body part with respect to the virtual rays passing there through. According to other exemplary embodiments, the image values of the respective image elements (e.g. voxels or clusters thereof) describing the virtual three-dimensional anatomical body part and defining the absorption properties of the respective image elements (e.g. voxels or clusters thereof) are changed in dependence on the trajectory similarity values assigned to the respective voxels before the virtual rays pass through the virtual three-dimensional anatomic body part in order to determine the dynamic DRR.

According to an aspect, the planning CT is not used for determining the dynamic DRR, and/or the similarity image and/or the dynamic CT. For example, only the 4D-CT is used for determining the dynamic DRR and/or the similarity image and/or the dynamic CT, this is for example done in order to reflect the dynamics, in a static two or three images dimensional image or a sequence of those images, for example to get deeper insight in the vital movements.

According to at least one exemplary embodiment, the image values of image elements of the dynamic DRRs are determined by using (for example considering) the trajectory similarity values such that the brightness of the at least some of the image values are different compared to a DRR determined from the planning CT in a usual manner (i.e. not using the trajectory similarity values, but anything else used for the determination, for example the assumed imaging geometry is the same), such a DRR being referred to herein as "usual DRR". For example, the image values being different relate to image elements representing secondary anatomical elements. According to at least one exemplary embodiment, the image values (for instance brightness) are changed compared to the usual DRR as a function of the trajectory similarity values related to the secondary anatomical element represented by the image value. Trajectory similarity values related to primary anatomical elements are referred to herein as first trajectory similarity values. For example, the first trajectory similarity values are 1. Trajectory similarity values related to secondary anatomical elements are referred to herein as second trajectory similarity values and are for example equal to or lower than the first trajectory similarity values.

The term "related" mentioned above means for example, that they relate to the same particular anatomical element represented in at least one three-dimensional matrix which describes at least one three dimensional image. For example, a trajectory similarity value is related (for example assigned) to a particular image element (for instance voxel) of the planning CT (which particular image element has a particular position in a matrix which describes the planning CT). For example, an image value of a particular image element (e.g. voxel or clusters thereof) has been modified based on the trajectory similarity value related to the particular image element, the particular image element representing a particular anatomical element.

Herein, the "positions" in a matrix mean that they relate to a particular anatomical element represented by an image element (for example voxel or cluster thereof) in a three dimensional image. "Same positions" means that they relate to the same particular anatomical element.

Instead of setting image values of image elements (voxels) representing the virtual three-dimensional anatomical body part to black level, it is also possible to disregard those image elements (voxels) when virtually passing the rays there through during rendering of the dynamic DRR. That is, those image elements are handled as if no absorption of the virtual ray happens at the location of the image element (for instance voxel). Correspondingly, if the image value (for instance brightness) is only modified and not set to for instance to minimum brightness (black level), a corresponding procedure would be to modify correspondingly the absorption of the virtual ray when passing to the corresponding image element (for instance voxel). As explained above, there are different ways to determine the dynamic DRR based on the determined trajectory similarity values. At least some of which will be explained below.

According to an exemplary embodiment, the undynamic CT is the planning CT. That is, the planning CT and the acquired undynamic CT are identical. In this case, the step of determining the dynamic DRR uses, according to an exemplary embodiment, the planning CT and the determined trajectory similarity values for determining the dynamic DRR. According to an exemplary embodiment, during determination of the DRR (for example during rendering the DRR) from the planning CT, the trajectory similarity values are considered. According to an exemplary embodiment, the "consideration of the trajectory similarity values", is performed when virtually passing the rays from the virtual radiation source through the virtual three-dimensional anatomical body part described by the planning CT. For example, the image values describe the transmission and/or absorption properties of the virtual three-dimensional body parts, for example by means of Hounsfield values (for example Hounsfield units). According to an exemplary embodiment, the transmission and/or absorption properties described by the image values of the planning CT are modified in accordance with the trajectory similarity values related to (for example assigned to) the different positions of the three dimensional matrix representing the planning CT. For example, if a trajectory similarity value assigned to a particular position of the matrix indicates no similarity, then unattenuated transmission is defined for the position during rendering of the dynamic DRR.

Herein, a change, for example a modification of an image value covers at least one of change of brightness or change of color (for example change of hue and/or change of saturation).

According to a further exemplary embodiment, the brightness values of the planning CT describes the transmission and/or absorption properties of anatomical elements represented by image values of the planning CT. For example, the brightness values are modified in accordance with the trajectory similarity values assigned to the respective positions of the matrix describing the planning CT. Alternatively or additionally, the colors of the image elements are modified in accordance with the trajectory similarity values (for example red in case of low similarity and green in case of high similarity). According to this exemplary embodiment, the planning CT is modified based on the trajectory similarity values assigned to the respective image elements (e.g. voxels) of the planning CT. That is, a modified planning CT is determined based on the trajectory similarity values. This modified planning CT describes a modified virtual anatomical body part through which the virtual rays pass in order to determine the dynamic DRR. For example, elements of the virtual anatomical body part are fully transmissive for x-ray, if trajectory similarity values related to these elements are below a threshold value. The planning CT modified by the trajectory similarity values respectively assigned to the image elements of the planning CT is also referred to herein as "dynamic planning CT". For example, the dynamic planning CT describes the transmission and/or absorption properties of a virtual anatomical body part through which the virtual ray pass during rendering of the dynamic DRR. Sometimes in the art, a CT generated by using contrast agents is referred to as a "dynamic CT". Herein "dynamic" is used in a different manner and a "dynamic CT" or a "dynamic planning CT" can be generated by using a contrast agent or by not using a contrast agent. Correspondingly, "undynamic" is used in a different manner and a "undynamic CT" can be generated by using a contrast agent or by not using a contrast agent.

According to further exemplary embodiments, the planning CT is not determined based on the 4D-CT but determined separately. According to an exemplary embodiment, in this case, a transformation is determined from the acquired undynamic CT to the planning CT.

Based on the trajectory similarity values determined as mentioned above, a three-dimensional image is acquired. This three-dimensional image is referred to as "similarity image". The positions of the image elements (for example voxels or clusters thereof) of the similarity image in a matrix which describes the similarity image correspond to positions of image elements of a matrix which describes the undynamic CT and the image values of the image elements of the similarity image correspond to the trajectory similarity values assigned to the corresponding image elements of the undynamic CT. For example, "corresponding positions" means that the respective trajectory similarity values are at the same positions in a matrix which describes the similarity image as the image elements of another matrix which describes the undynamic CT to which they are respectively assigned.

For example, the transformation is applied to the similarity image in order to determine a transformed similarity image. The transformed similarity image is transformed so that the image elements of the transformed similarity image are at positions in a matrix which describes the transformed similarity image which correspond to positions of image elements of another matrix which describes the planning CT, the corresponding positions relate to the same anatomical element. That is, the transformation results in that trajectory similarity values are assigned to the respective image elements of the planning CT.

For example, the dynamic DRR is determined by using the planning CT and the determined trajectory similarity values wherein, during determination of the DRR from the planning CT, the trajectory similarity values represented by the image elements of the transformed similarity image are used. That is, the attenuation of the virtual ray passing through the virtual three-dimensional body represented by the planning CT is modified in dependence on the image values of the transformed similarity image being assigned to respective image elements of the playing CT (as mentioned before). According to a further example, the image elements of the planning CT are modified based on the transformed similarity image. As mentioned above, the transformed similarity image allows to assign to each image element of the planning CT a trajectory similarity value which is a corresponding image value of the transformed similarity image. The assigned trajectory similarity value is used to change the image values of the planning CT. The term "corresponding" means in this respect that the trajectory similarity values of the transformed similarity image adopt the same position in the transformed similarity image as the corresponding image elements of the planning CT do.

The planning CT modified as mentioned above is referred to herein as "dynamic planning CT". The procedure for determining the DRR is applied to the dynamic planning CT in order to determine the dynamic DRR.

According to at least one further exemplary embodiment, the planning CT is acquired independently from the undynamic CT as described above. In this case, for example, a transformation from the undynamic CT to the planning CT is determined.

Furthermore, for example, a three-dimensional image (referred to as dynamic CT) is determined by changing image values of at least a part of the second image elements of the undynamic CT. The change of the image values is performed in dependence on the trajectory similarity values assigned to respective image elements of the undynamic CT. In other words, for the respective image elements of the undynamic CT, the respectively assigned trajectory similarity values modify the respective image value of the respective image element of the undynamic CT. For example, the trajectory similarity values are determined as mentioned above for the respective image elements of the undynamic CT and then assigned to the respective image elements of the undynamic CT for which they have been determined.

For example, the determined transformation is applied to the dynamic CT in order to determine a CT referred to as "dynamic planning CT". That is the transformation (transformations herein are spatial transformations) transforms the dynamic CT into the dynamic planning CT. At least a part of the second image elements of the dynamic planning CT reflect the previously determined correlation.

For determining the dynamic DRR, for example, the dynamic planning CT is used as a basis for digitally reconstructing the two-dimensional image from the dynamic planning CT. That is, the virtual rays pass through a virtual anatomical body part, the transmission and/or absorption properties of the elements of the body part being described by the image values of the dynamic planning CT.

According to an example of at least one exemplary embodiment, the primary and secondary trajectories are determined as described in the following. Transformations referred to as sequence transformations are determined. The sequence transformation describes transformations between sequence CTs. For example, a transformation from the undynamic CT to another one of the sequence CTs (in case the undynamic CT is one of the sequence CTs). For example, the sequence transformations allow to transform between subsequent ones of the sequence CTs. For example, the sequence transformation are constituted to transform from the undynamic CT to other ones of the sequence CTs. The transformations are preferably performed by using image fusion. For example, the sequence transformations are constituted so that the positions of the image elements of a respective one of the sequence CTs can be transformed to the positions of the respective image elements in another respective one of the sequence CTs. Thus, the determined sequence transformations allow to determine a change of position of image elements in the sequence. This change of positions represents trajectories of anatomical elements described by the respective image elements.

For example, the trajectories of the at least one first image element and of at least some of the second image elements are determined by applying the determined sequence transformations to the at least one first image element and to the at least some of the second image elements.

According to at least one exemplary embodiment, the trajectory similarity values are determined based on the trajectories. According to an example of the at least one exemplary embodiment, the trajectory similarity values are determined as a function which has a positive value and is the higher the higher an absolute value of a difference between a minuend and a subtrahend is. The function is referred to as absolute difference function and is for example the function of squared differences, difference to the fourth power, sixth power . . . or a function for obtaining an absolute value of the difference. The minuend and subtrahend depend on positions of two different trajectories at a particular (same) time. One of the two trajectories being a primary trajectory, according to an embodiment the reference primary trajectory.

For example, the calculation of the trajectory similarity values can be performed for each coordinate of a coordinate system in which the trajectories are at rest. For instance, a first deviation (difference) of a first image element from a mean average value of the position of the first image element can be subtracted from a second deviation (difference) of a second image element from an average position with respect to the same coordinate and then those two deviations are subtracted and for example the absolute difference function is applied to this difference.

The aforementioned positive values can be weighed differently for each coordinate axis in order to determine a value which reflects the correlation for example for all three axes of the coordination system. This determined value is for example the trajectory similarity value. Furthermore, a threshold function can be applied to value in order to obtain the trajectory similarity value.

According to at least one further exemplary embodiment, the trajectory similarity value is determined based on calculation of a correlation coefficient. For example, the trajectory similarity value is a function of a product of the aforementioned first and second deviations. For example, this function is calculated for each axis of the coordination system. The different values for different axes of the coordination system can be weighed. Optionally a threshold function can be applied to the result of the function in order to obtain trajectory similarity values.

According to a further exemplary embodiment, the trajectory similarity value is a value referred to as amplitude similarity value. For example, the trajectory similarity value is a function, for example threshold function of the amplitude similarity value. For example, the amplitude similarity value reflects similarity of amplitudes of first and second image elements while they undergo a cyclic (for instance periodic) movement. More details are given below in the detailed exemplary embodiments. The aforementioned exemplary embodiments and examples for determining the trajectory similarity value can be combined. According to a further exemplary embodiment both the correlation coefficient and the amplitude similarity value (which describes for example similarity of a peak to peak amplitude) can be combined. For example, both the correlation coefficient and the amplitude similarity value are respectively subjected to a threshold function having respective threshold values. For example, the trajectory similarity value is determined by using a function which sets the trajectory similarity value to a value which indicates similarity if both the correlation coefficient and the amplitude similarity value are above their respective threshold values. If one of them is below, then the trajectory similarity value is set to indicate "not similar" (which for example results in that a corresponding image element in the dynamic DRR is set to black level).

According to at least one exemplary embodiment of Annex A, the computer implemented method further comprises the steps of determining at least one of the at least one first image element or the second image elements by using an anatomical atlas. The steps in particular comprise segmenting the undynamic CT by using the atlas. The segments achieved by means of the segmenting being identified to correspond to one or more (for instance clusters) of the second image elements and/or the at least one first image element. In particular, image elements can be excluded from the processing (for example by not calculating the trajectories for them) which are part of segments known to be not subjected to a vital movement or a vital movement which is not similar to that of the treatment body part. Or for those image elements the trajectory similarity values are set to indicate no similarity.

According to at least one further exemplary embodiment, the computer implemented method comprises the step of displaying the dynamic DRR over an x-ray image (for example by superposition) or besides an x-ray image. The x-ray image is for example used by an operator (for instance surgeon or physicist) to determine the position of a treatment body part to be subjected to treatment radiation. The display of the dynamic DRR can be used for (planning) the positioning of the patient for the radiotherapeutic treatment.

According to an example, image values (for example of the similarity image) representing the trajectory similarity values can have a brightness or color (for example hue and/or saturation) which depends on the trajectory similarity value.

According to a further aspect, a computer implemented method is provided which is for example used to determine the above-mentioned similarity image and/or dynamic CT and/or dynamic DRR. The determination is for example based on a 4D-CT, for example not based on a planning CT, for example uses (only) the 4D-CT. The 4D-CT describes for example a sequence of three-dimensional medical computer tomographic images of an anatomical body part (referred to as sequence CTs). The sequence CTs represent the anatomical body part at different points in time. The anatomical body part comprises at least one primary anatomical element and secondary anatomical elements. This further aspect is for example used if no radiotherapeutic treatment is intended for the patient and if there is no need for a planning CT. This further aspect is for example used if further insights in the (anatomical) dynamics of the patient is required. With exception of the use of the planning CT, the method according the further aspect comprises one or more step combinations as described above. According to a further aspect, a complete implement method is provided which uses at least or only the steps shown in FIG. 1 for determining the trajectory similarity values. According to a further aspect, a computer implemented method is provided that uses the steps S20 and S24 of FIG. 2, while in step S24 the dynamic DRR is determined by using the undynamic CT instead of the planning CT. According to further aspects, method uses the steps in FIG. 3 with exception of step as 32. Furthermore, step 34 has changed in that the dynamic CT is determined by using the undynamic CT and the determined trajectory similarity values and by changing image values of the undynamic CT independence on the trajectory similarity values. Finally, the step S36 has changed in that the dynamic DRR is determined from the dynamic CT. According to aspects, at least one of the dynamic DRR or the dynamic CT is displayed. According to a further aspect, the steps of FIG. 1 are supplemented by step of displaying the determined trajectory similarity values as three-dimensional similarity image.

The computer implemented method according to the further aspect comprises steps as mentioned below, examples for at least some of the steps are described with respect to other aspects described herein and are therefore not (again) described in detail.

For example, the 4D-CT is acquired. A planning CT is acquired. The planning CT is according to a first exemplary embodiment acquired based on the 4D-CT. For example, by interpolation between one of the sequences CTs or by defining one of the sequence CTs to be the planning CT. According to a further alternative exemplary embodiment, the planning CT is acquired independently from the 4D-CT for example by receiving CT data from a medical analytical imaging device which is constituted to generate CTs.

For example, the computer implemented method further comprises the step of acquiring a three-dimensional image, referred to as undynamic CT, from the 4D-CT. For example, one of the sequence CTs is selected as the undynamic CT. The selection is for instance performed on a visual basis. For instance, an operator selects one of the sequence CTs in which a treatment body part can be visually best segmented from other body parts. According to a further example, a segmentation of the treatment body part by using an atlas has highest confidence level for the treatment body part in case of the selected sequence CT. The aforementioned features can be combined also with the other aspects mentioned before.

In a further step, for example, a trajectory is acquired, the trajectory is referred to as primary trajectory. The acquisition is for example based on the 4D-CT. The primary trajectory describes a path of the at least one first image element as a function of time.

For example, in a further step, trajectories of the second image elements are acquired. The trajectories are referred to as secondary trajectories. The acquisition is for example based on the 4D-CT.

For example, in a step trajectory similarity values are determined. The trajectory similarity values are determined for the image values of the undynamic CT. The determination is for example based on the primary trajectory and the secondary trajectories. The trajectory similarity values respectively describe a means for similarity as described herein.

For example, in another step, the similarity image is determined by determining the trajectory similarity values to be image values of image elements of a similarity image.

The image elements of the similarity image are referred to as similarity image elements. The image elements of the undynamic CT are referred to as undynamic image elements. As described with respect to other aspects, the determination of the similarity image is performed so that the positions of the similarity image elements correspond to the positions of the undynamic image elements of the undynamic CT to which the trajectory similarity values are respectively related.

The acquisition of a planning CT is optional. For example, the similarity image can be determined without using the planning CT.

Optionally, in case the planning CT is not acquired based on the 4D-CT but independently from the 4D-CT, a transformation is further determined from the undynamic CT to the planning CT (examples therefore are described above with respect to the other aspect). For example, the determined transformation is applied to the similarity image (examples therefore are described herein with respect to the other aspects).

According to a further exemplary step, the similarity image or the transformed similarity image is displayed For Example, the similarity image is determined for each CT of the sequence CT. For example, a change of the similarity images is visualized by a movie play feature.

According to another exemplary embodiment of this aspect, the similarity image or the transformed similarity image is displayed over or besides a CT, for example sequence CT and/or planning CT. According to another exemplary embodiment, a DRR (referred to as similarity DRR) is rendered using the similarity image as the tree dimensional image in the manner described above. For example, the same imaging geometry is used for the rendering of the similarity DRR as for generation of a two-dimensional x-ray image which is for example used for placing a patient. The similarity DRR is for example display over the two-dimensional x-ray (for example superposed) or displayed besides the two-dimensional x-ray image.

According to a further aspect, a program is provided which when running on a computer or when loaded into a computer causes the computer to perform at least one of the computer implemented methods described herein.

According to a further aspect, a signal wave is provided, which carries information which represent the program according to the aforementioned aspect.

According to a further aspect, a program is provided, which comprises code means adapted to perform all the steps of at least one of the computer implemented methods described herein.

According to a further aspect of Annex A, a program storage medium is provided, on which the program according to at least one of the aforementioned aspects is stored. The program is for example stored in a non-transitory manner.

According to a further aspect of Annex A, a computer is provided, on which the program according to at least one of the aforementioned aspects is running or in which such a program is loaded. The computer is for example constituted to perform at least one of the aforementioned computer implemented methods. For example, the computer comprises the program storage medium of one of the aforementioned aspects.

According to further aspects of Annex A, a system is provided. The system comprises for example the computer according to the aforementioned aspect. For example, the system further comprises a display device (for example a computer monitor) for displaying the dynamic DRR determined in accordance with one of the aforementioned aspects. For example, the display device is alternatively or additionally constituted to display the similarity image according to one of the aforementioned aspects. For example, the computer comprises an interface (for example a digital and/or electronic interface) for receiving data, for example the 4D-CT and/or the planning CT.

According to a further exemplary embodiment of this aspect, the system comprises a couch for placing a patient, for example for treatment with treatment radiation. The system for example further comprises according to this exemplary embodiment, a treatment device constituted to emit a treatment beam for treating the patient by means of treatment radiation.

According to a further exemplary embodiment of this aspect, the system comprises an analytical device constituted for generating the 4D-CT.

For example, according to a further exemplary embodiment, the system alternatively or additionally comprises an analytical device constituted for generating the planning CT.

Description of FIGS. 6 to 14

Figure 6:
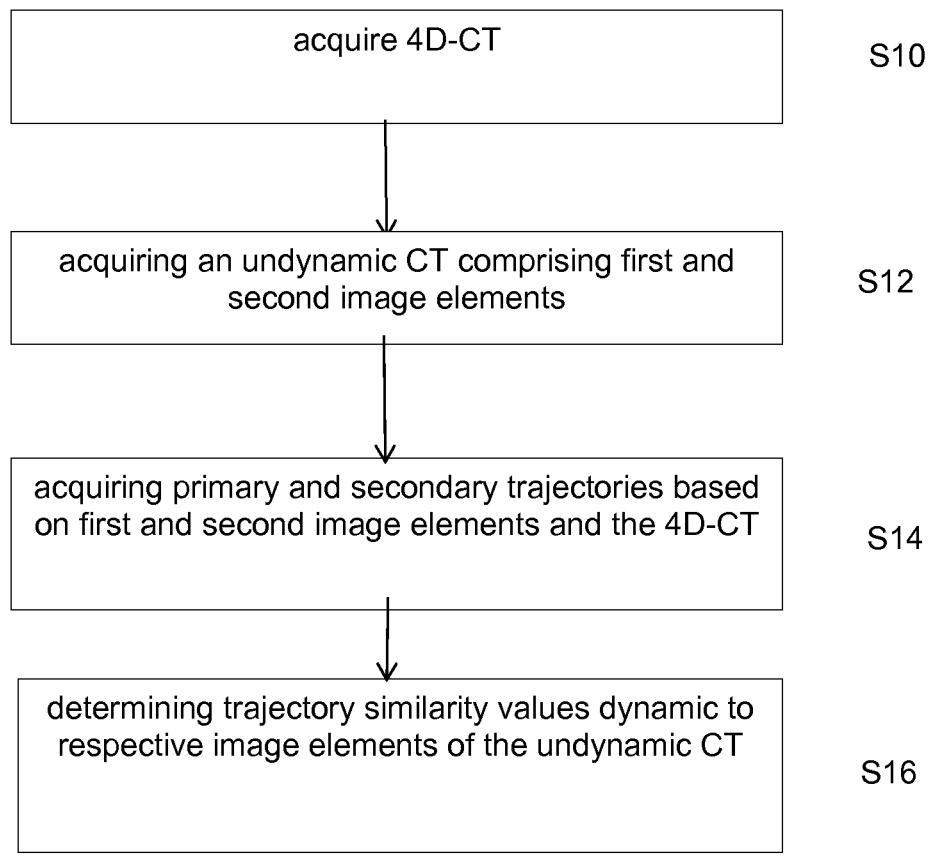
FIG. 6 shows a flowchart related to the determination of trajectory similarity values as described in Annex A.

FIG. 6 shows steps for determining the trajectory similarity values. According to step S12, the undynamic CT is acquired. According to step S14, the primary and secondary trajectories are acquired. For example, the primary and secondary trajectories are determined based on the acquired undynamic CT, for example based on the at least one first image element and the second image elements. For example, the first image element is a tumor. For example, the second image elements represent secondary anatomical elements. For example, the secondary anatomical elements are discernible in an x-ray image. For example, those secondary anatomical elements have a strong interaction with x-rays (for example by absorbing the x-rays) than fluids (for example water, air).

Figure 12:
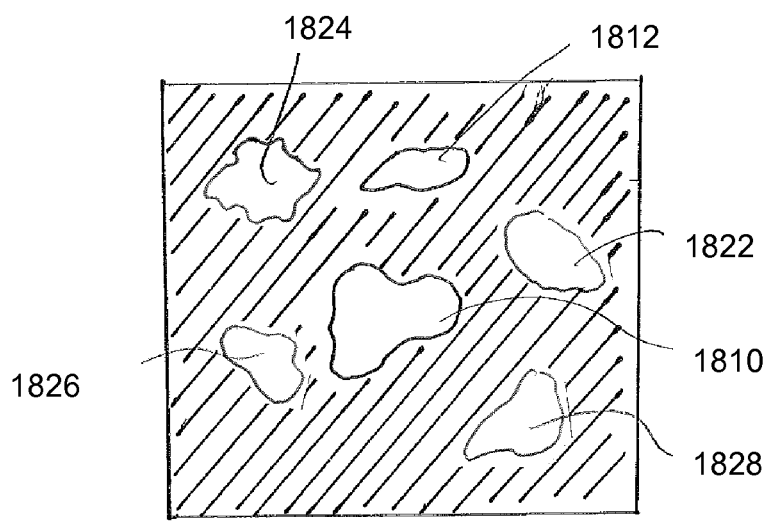
FIG. 12 shows a schematic representation of a usual DRR which was generated from a schematic planning CT in accordance with methods known in the art as described in Annex A.

Having a reference to FIG. 12, it is assumed that FIG. 12 represents a schematic usual DRR generated from the dynamic CT which is assumed to correspond to the planning CT. Then according to an example, region 1810 represents the treatment body part and is generated from a cluster of voxels of the planning CT which corresponds to the undynamic CT. That is, the region 1810 in FIG. 12 corresponds to a cluster of first image elements of the undynamic CT from which the usual DRR of FIG. 12 is generated. Accordingly, according to an example, the regions 1812, 1822, 1824, 1826, and 1828 are generated from clusters of second image elements of the undynamic CT (which is identical to the planning CT).

According to step S14 of the FIG. 6, primary and secondary trajectories are acquired based on first and second image elements of the undynamic CT and based on the other sequence CTs defined by the 4D-CT. As mentioned above, preferably image fusion methods are used to determine the trajectories. In a next step, for example, the trajectory similarity values related to the respective image elements of the undynamic CT are determined. For example, this is done for each voxel of the undynamic CT or for voxel clusters. According to an example, the trajectory similarity values for the voxels being inside the region generated from a voxel cluster of the undynamic CT which results in the regions 1822, 1824, and 1826 are lower than a threshold value and the trajectory similarity values for the voxels inside the voxel clusters of the undynamic CT from which the regions 1810 and 1812 are generated in FIG. 12 have a value above the threshold value. Again, the aforementioned example relates to the case where the undynamic CT corresponds to the planning CT.

Detailed examples for the calculation of trajectory similarity values are given below.

Figure 7:
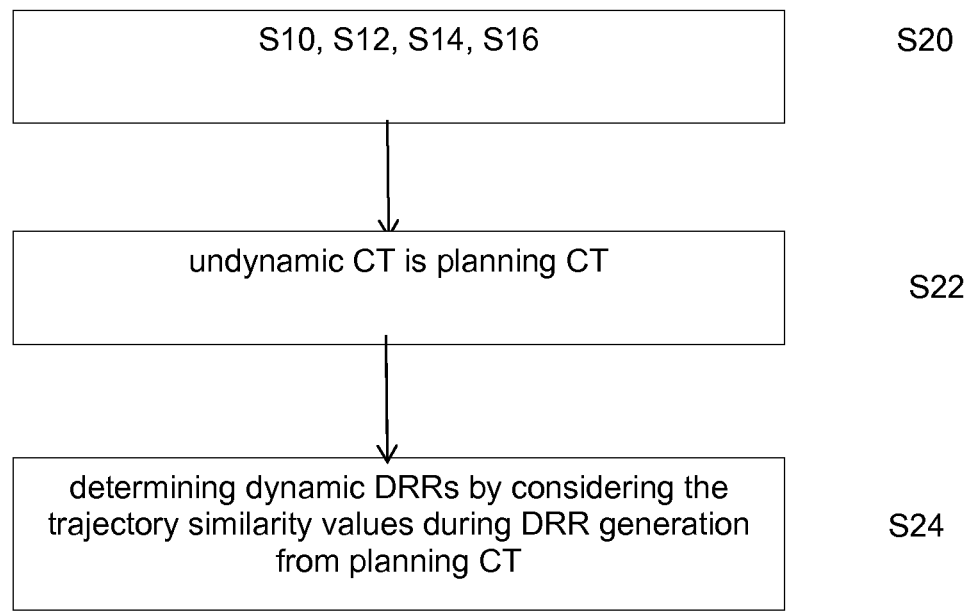
FIG. 7 shows a flowchart according to one exemplary embodiment according to at least one exemplary embodiment for determining dynamic DRRs as described in Annex A.

FIG. 7 relates to an exemplary embodiment for determining the dynamic DRRs according to the flowchart shown in FIG. 7. According to the flowchart shown in FIG. 7, the computer implemented method relates to the case where the undynamic CT is the planning CT. For example, there is a step of selecting one of the sequence CTs as the planning CT and the undynamic CT. This step can be performed by an operator.

For example, the steps of FIG. 6 are also performed according to an exemplary embodiment described in FIG. 7. The combination of steps of FIG. 6 are indicated as step S20 in FIG. 7. For example, it can be defined that the undynamic CT should be the planning CT before or after step S20 or simultaneously to step S20 (see step S22 in FIG. 7).

Figure 13:
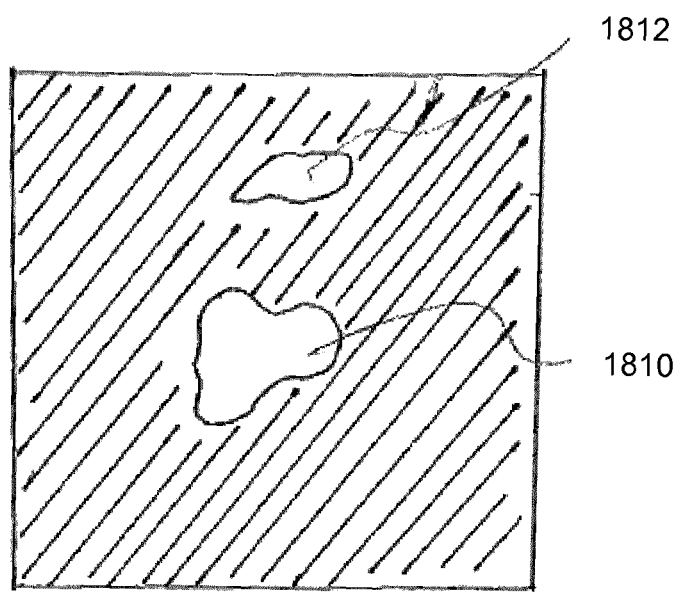
FIG. 13 shows a dynamic DRR generated from the same assumed schematic planning CT according to an example as described in Annex A.

In step S24 the dynamic DRRs are determined by considering the trajectory similarity values during DRR generation from the planning CT. As mentioned above, the consideration can be performed by modifying the absorption properties (Hounsfield values) described by the image values of the planning CT in dependence on the trajectory similarity value assigned to the corresponding image element. For instance assume, the trajectory similarity values related to anatomical elements represented by regions 1822, 1824, 1826, and 1828 are below a threshold, then for example the image values for these regions are set to black as shown in FIG. 13.

Figure 8:
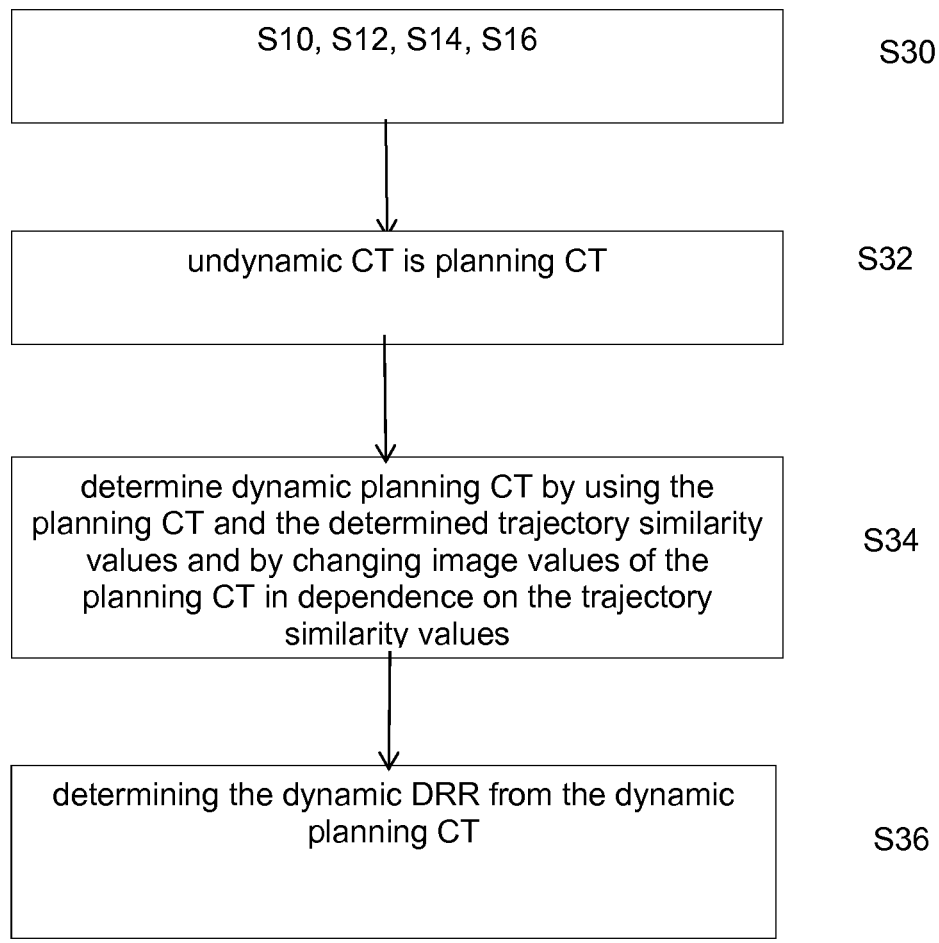
FIG. 8 shows a flowchart according to one exemplary embodiment according to at least one exemplary embodiment for determining dynamic DRRs as described in Annex A.

FIG. 8 is a further flowchart which represents at least one further exemplary embodiment.

The steps S30 and S32 correspond to steps S20 and S22 in FIG. 7 and can be interchanged or performed simultaneously.

According to step S34, the dynamic planning CT is determined by using the planning CT and the determined trajectory similarity values and by changing the image values of the planning CT in dependence on the trajectory similarity values. For example, the image values of the planning CTs represent Hounsfield values which are a measure for the interaction of the corresponding anatomical body part represented by the image value with the x-rays. By changing the image values of the planning CT in dependence on the trajectory similarity value, the subsequent determination of the dynamic DRR is influenced. This determination is performed in step S36. The dynamic DRR is performed in the usual manner of generating a DRR but not based on a usual planning CT but on the dynamic planning CT determined in step S34.

Figure 9:
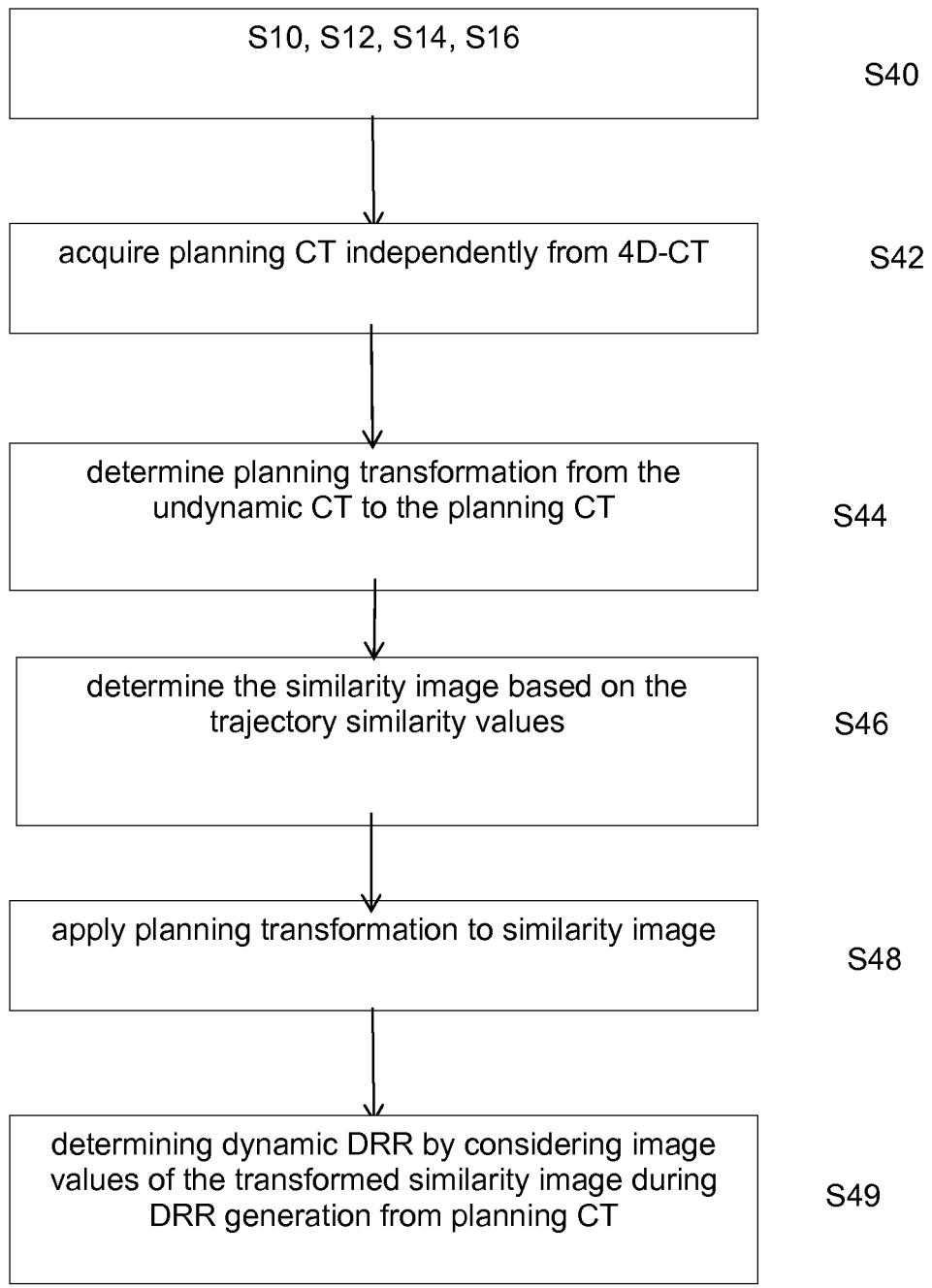
FIG. 9 shows a flowchart according to one exemplary embodiment according to at least one exemplary embodiment for determining dynamic DRRs as described in Annex A.

According to the at least one exemplary embodiment shown in FIG. 9, there is first the step S40 which corresponds to the combination of steps shown in FIG. 6. Before, after or simultaneously this step, a step S42 is performed for acquiring a planning CT independently from the 4D-CT. This step is step S42. Based on the undynamic CT determined in step S40, a planning transformation is determined from the undynamic CT to the planning CT for instance by using image fusion. This is done in step S42.

The step S46 can be performed before S42 or step S44 or simultaneously thereto, for example. The step S46 uses the trajectory similarity values determined in step S40 to determine the similarity image explained above.

According to step S48, the planning transformation determined in step S44 is applied to the similarity image.

According to step S49, the dynamic DRR is determined by considering image values of the transformed similarity image during DRR generation from the planning CT. The "consideration of image values" is performed in the same manner as described above with respect to the generation from the planning CT in step S24.

Figure 10:
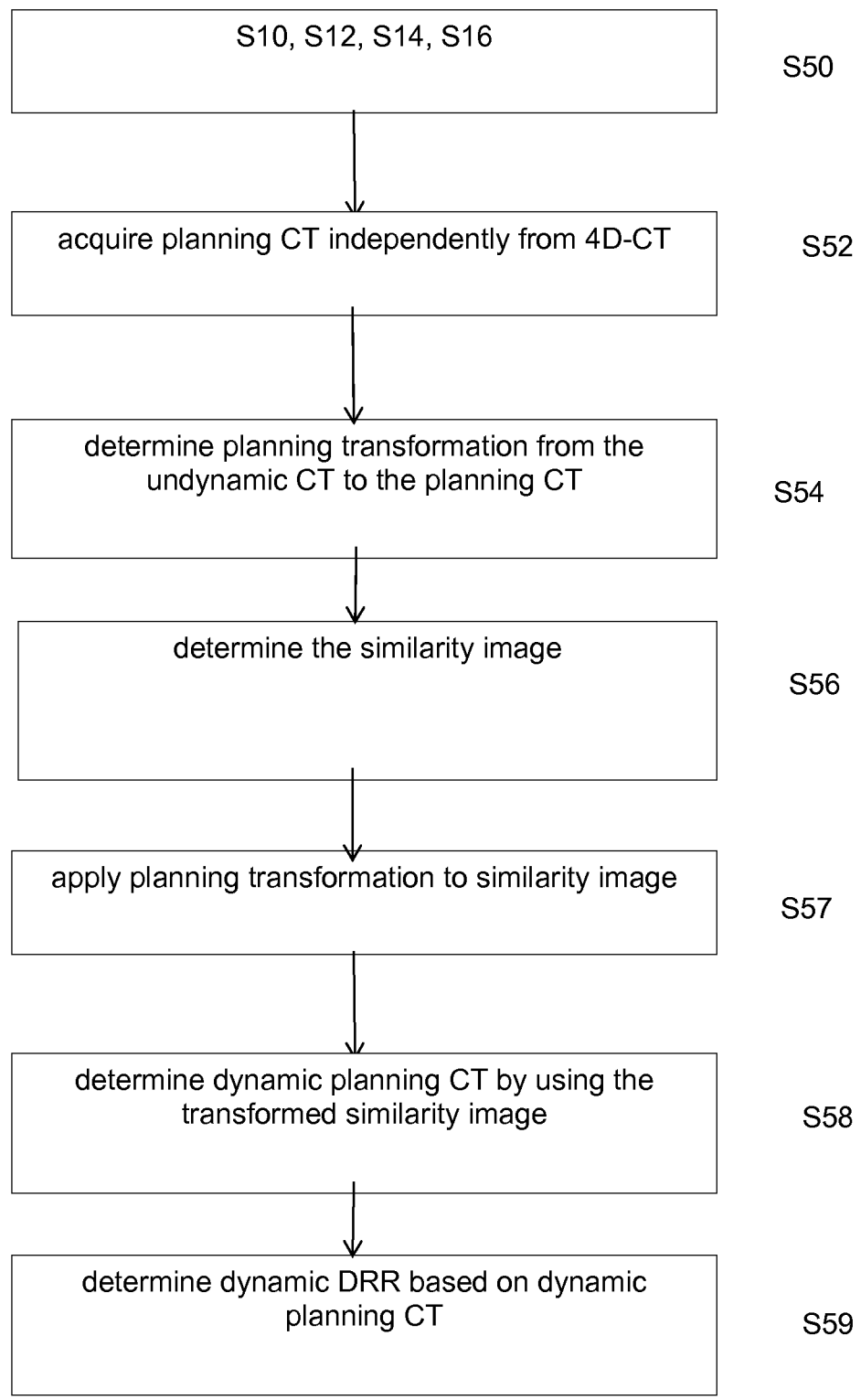
FIG. 10 shows a flowchart according to one exemplary embodiment according to at least one exemplary embodiment for determining dynamic DRRs as described in Annex A.
Figure 11:
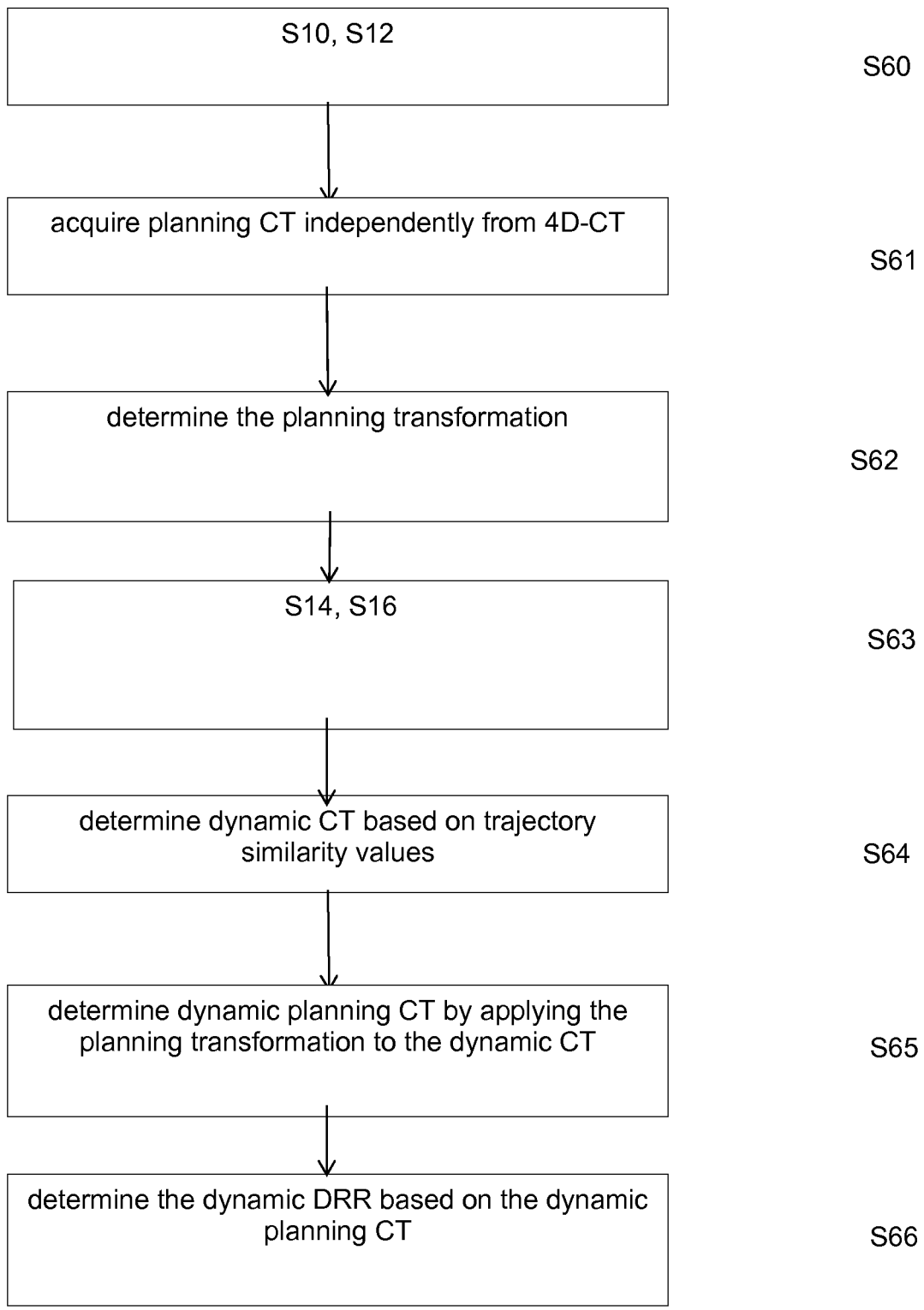
FIG. 11 shows a flowchart according to one exemplary embodiment according to at least one exemplary embodiment for determining dynamic DRRs as described in Annex A.

According to the at least one exemplary embodiment shown in FIG. 10, which is an exemplary flowchart, a step S50 is performed, which comprises the steps of the FIG. 11.

For example, a step S52 is performed, which relates to the acquisition of the planning CT independently from the 4D-CT. That is, the patient is for instance before or after the generation of the 4D-CT subjected to medical image generation by means of an analytical device for generating a CT. According to at least one exemplary embodiment, the planning CT is static and not time dependent.

According to the step S54, a planning transformation is determined from the undynamic CT to the planning CT. For example, this is performed in the manner as described before with respect to step S44.

According to step S56, the similarity image is determined by using the trajectory similarity values determined in step S50. For example, the step S56 is performed before or after step S54 or before or after step S52 or simultaneously to one of those steps.

According to step S57, the planning transformation is applied to the similarity image for determining a transformed similarity image.

For example, according to a further step S58, the dynamic planning CT is determined by using the transformed similarity image. That is, the trajectory similarity values of image elements of the similarity image are used to modify image values of corresponding image elements of the planning CT. "corresponding image elements" are image elements which are at the same position in the planning CT as corresponding image elements in the similarity image.

For example, in a step S59, the dynamic DRR is determined based on the dynamic planning CT by applying usual methods known in the art for determining a DRR from a CT.

According to at least one further exemplary embodiment, a flowchart shown in FIG. 11 describes method steps of the at least one further exemplary embodiment. According to step S60, the steps S10 and S12 are performed. According to step S61 the planning CT is acquired independently from a 4D-CT as described above with respect to step S42 or step S52. For example, the step S60 is performed before, after or simultaneously to step S61 or S62.

For example, according to step S62, the planning transformation is determined based on the undynamic CT and the planning CT.

For example, in a step S63, the steps S14 and S16 of FIG. 6 are performed for determining the trajectory similarity values. For example, the determined trajectory similarity values are used in step S64 to determine the dynamic CT. The dynamic CT is a three-dimensional image which is for example determined by changing image values of the undynamic CT. The change is performed based on the trajectory similarity values determined in step S63. For example, in step S63 the trajectory similarity values are determined for particular image elements of the undynamic CT. That is, the trajectory similarity values are assigned to the respective image elements. The assigned trajectory similarity values are then used to change the image values of image elements of the undynamic CT in step S64. For example, this is at least done for at least a part of the second image elements. For example, this is done in case the trajectory similarity values are below a predetermined threshold.

For example, according to another step S65, the dynamic planning CT is determined by applying the planning transformation to the dynamic CT.

For example, according to a step S66, the dynamic DRR is determined based on the dynamic planning CT in a manner which is usual for determining a DRR from a CT.

FIG. 12 has already been described above.

FIG. 13 represents a schematic and exemplary example of a dynamic DRR. It is assumed that the region 1810 represents the treatment body part (for instance tumor). FIG. 13 represents a region which has been generated from the planning CT. The region represents the DRR projection of a voxel cluster. The trajectory similarity values assigned to the voxel cluster are above a predetermined threshold value. That is, the region 1812 represents a body part which undergoes a similar vital movement as the treatment body part 1810. The term "similar" covers herein identical and the usual meaning of "similar". For example, image values related to trajectory similarity values above a predetermined threshold remain unchanged are not influence by the trajectory similarity values, and remain for example unchanged during determination of the dynamic DRR. In FIG. 13, the regions 1822, 1824, 1826 and 1828 are missing since the trajectory similarity values relating to those regions are below a predetermined threshold value. According to an exemplary alternative embodiment, the trajectory similarity value is a value which represents the result of application of the threshold function. That is, the trajectory similarity value is for example a binary value which is for example zero for "non-similarity" and one for "similarity". That is, in this exemplary embodiment, the trajectory similarity values for the voxel clusters which represent the regions 1822, 1824, 1826 and 1828 in the planning CT are related to trajectory similarity values which indicate non-similarity (for example having a value of 0).

Figure 14:
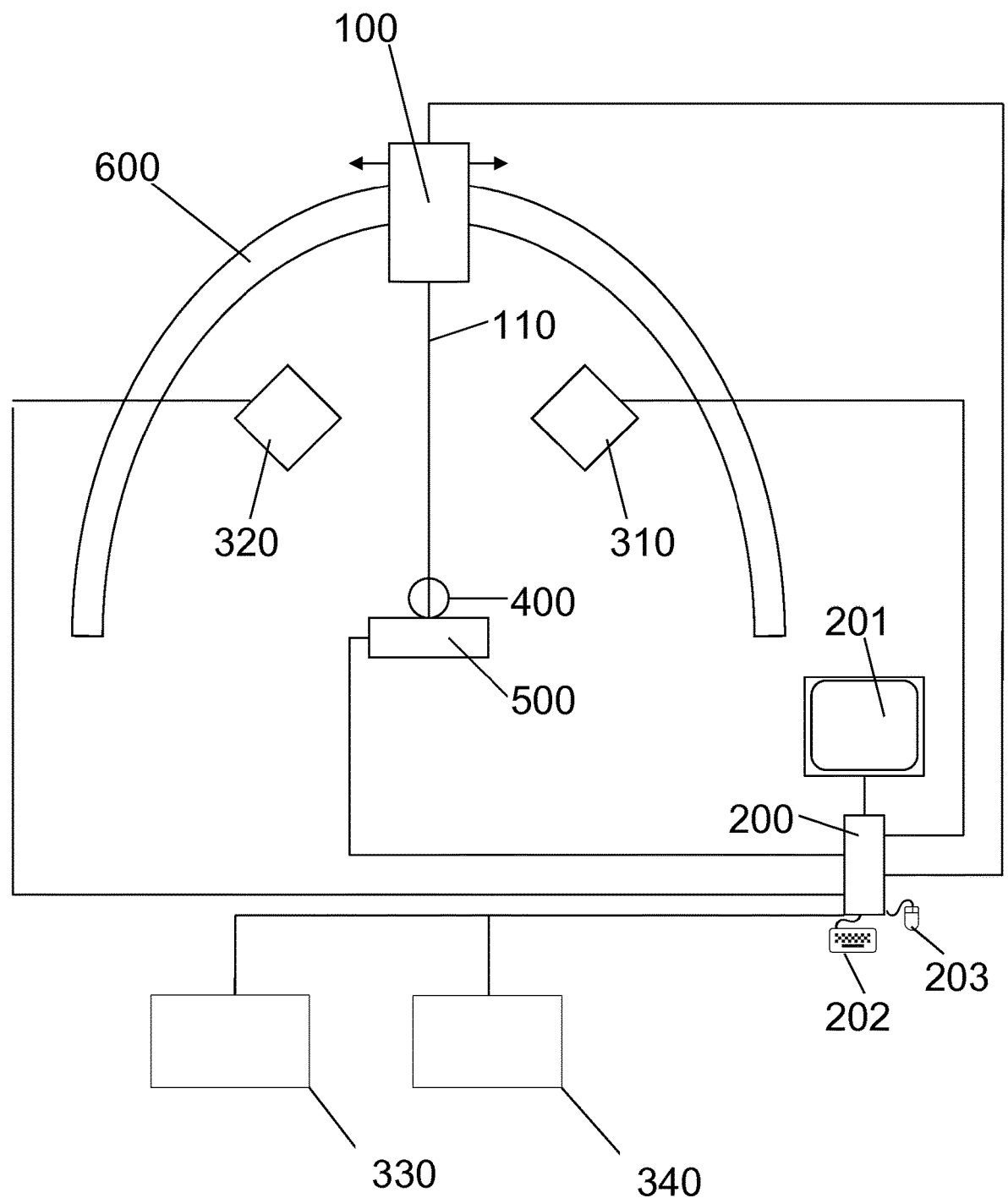
FIG. 14 shows a system according to at least one exemplary embodiment as described in Annex A.

FIG. 14 shows at least one exemplary embodiment according to an aspect of Annex A which is related to a system. The system comprises for example a computer 200. To the computer 200 is connected a monitor 201, a keyboard 202, and a mouse 203, for example. For example, the computer 200 is connected to the treatment device 100 which can, for example, be moved along an arc 600. For example, x-ray devices 310 and 320 are used to make a two-dimensional x-ray image from a patient 400 which is placed on a couch 500. Alternatively or additionally, the computer 200 can be connected to the couch 500 for changing the position of the couch 500. Alternatively or additionally, the computer 200 can be connected to an analytical device 330 for generating the 4D-CT. Additionally or alternatively, the computer 200 can be connected to the analytical device 340 for generating the planning CT.

The connections described above are for example constituted to transfer image data. The connection can be wired or wireless.

Exemplary Steps of at Least One Example

According to an example, the different points in time assigned to respective sequence CTs referred to different breathing states of a patient. For example, the respective sequence CTs are assigned to 100% inhaled, 25% exhaled, 50% exhaled, 75% exhaled, 0% inhaled, 25% inhaled, 50% inhaled, 75% inhaled.

For example, one of the sequence CTs, to which a particular point in time (for instance particular respiratory state) is assigned, is selected as the undynamic CT. The selection is for instance performed as described in WO 2015/127970. That is, that one of the sequence CTs is selected as undynamic CT, in which the target is good discernible.

For example, in order to determine the primary and secondary trajectories, image fusion (for example elastic fusion) is performed for the different points in time (respiratory states).

For example, the undynamic CT acts as a source for the calculation of the trajectories. For example, elastic fusion mapping is used to get a first image element (target point) at a certain point in time (for instance certain phase of respiration) for every first image element of the undynamic image. For example, the image elements are voxels or cluster of voxels.

For example, the trajectory is defined by means of the image elements at different points in time. For example a trajectory is mathematically defined by T, then T={source point, target point (10%), target point (20%), . . . , target point (90%)}.

For example, the points of the trajectory describe positions of three-dimensional image elements for a particular point in time, for example of voxels or cluster of voxels. For example, the trajectory is a sorted list of the points. For example, the points are sorted by time (for example phase, for example phase of respiration).

Examples for calculating a measure of similarity for the trajectories is given in the following.

First example of calculation of a similarity measure is based on a sum of squared differences.

In the following, the abbreviation "SSD" stands for sum of squared differences. The abbreviations X, Y, Z stand for the coordinates of a three-dimensional coordination system within which the trajectory is described. The latter T1 stands for example for a trajectory of a treatment body part, for example of an isocenter of the treatment body part or of center of mass of a treatment body part. That is T1x(i) is the x coordinate of the treatment body part at the time (for instance phase) "i". 1x is the average x coordinate of the treatment body part averaged over all points in time (for example all states of respiration). Correspondingly, T2x stands for the x coordinate of an image element (for example voxel) of the undynamic CT at the point in time (i) and 2x stands for the average x coordinate of this image element averaged over the different points in time (for example states of respiration). The calculation is for example as follows:

$$SSDX = \sum_{i=1}^{n} ((T_{1x}(i) - T_{1x}) - (T_{2x}(i) - T_{2x}))^2$$

$$SSDY = \sum_{i=1}^{n} ((T_{1y}(i) - T_{1y}) - (T_{2y}(i) - T_{2y}))^2$$

$$SSDZ = \sum_{i=1}^{n} ((T_{1z}(i) - T_{1z}) - (T_{2z}(i) - T_{2z}))^2$$

$$SSD_{XYZ} = \frac{w_x * SSDX + w_y * SSDY + w_z * SSDZ}{w_x + w_y + w_z}$$

The above equations represent an approach to compute a measure of similarity of trajectories based on sum of squared differences. SSDXYZ is an example for a trajectory similarity value or the result of applying a threshold function to SSDXYZ is an example for a trajectory similarity value.

According to another example, correlation and amplitude correspondence are determined separately for determining the measure of similarity. For example, as described below, the correlation and the amplitude correspondence can be mixed, after separate determination in order to determine a trajectory similarity value as a measure of similarity or can respectively be used as a measure of similarity.

According to an example, a normalized correlation coefficient is calculated as follows:

For all three dimensions x,y,z the correlation coefficient is computed separately and the average correlation coefficient is taken as final measure. One could also think about weighting the correlation coefficients e.g. if a tumor is moving with diaphragm I-S correlation coefficient y (I/S) should get more weight. The equations below describe computing the normalized correlation coefficient for x,y,z, and the combination to be taken as a trajectory similarity value. T1 and T2 have the meaning as described above, and n is the number of points of each trajectory.

$$SSDX = \sum_{i=1}^{n} ((T_{1x}(i) - T_{1x}) - (T_{2x}(i) - T_{2x}))^2$$

$$SSDY = \sum_{i=1}^{n} ((T_{1y}(i) - T_{1y}) - (T_{2y}(i) - T_{2y}))^2$$

$$SSDZ = \sum_{i=1}^{n} ((T_{1z}(i) - T_{1z}) - (T_{2z}(i) - T_{2z}))^2$$

$$SSD_{XYZ} = \frac{w_x * SSDX + w_y * SSDY + w_z * SSDZ}{w_x + w_y + w_z}$$

The above equations represent an example for an approached compute a similarity measure for describing the similarity between trajectories based on correlation coefficient. The abbreviation "CC" stands for correlation coefficient. CCXYZ is an example for a trajectory similarity value or the result of applying a threshold function to CCXYZ is an example for a trajectory similarity value.

To determine a trajectory similarity value, a correlation coefficient can be combined with a value which describes similarity of amplitude of trajectories. An exemplary approach is described below:

For correlation coefficients that exceed a certain threshold (e.g. 0.7) one could add a second threshold focusing on the amplitude. The more accordance in the absolute value of the value, the higher the value. Here an exemplary equation focusing on the main direction of the target, in this case inferior-superior (I-S), the breathing motion caused by the diaphragm.

$$A_{IS} = \frac{\text{Min}(A_1, A_2)}{\text{Max}(A_1, A_2)}$$

In the above equation A1 describes the peak to peak amplitude of a trajectory of the treatment body parts (for example isocenter or center of mass of treatment body part). For example, the amplitude is along a particular axis of the coordinate system or a long one of the axis described for instance by a rotational ellipsoidal. A2 describes the corresponding peak to peak amplitude of an image element of the undynamic CT. The terms "Min" and "Max" stand for the function of determining the minimum respectively the maximum of A1 and A2.

According to a further embodiment, the threshold value of the above described threshold function is changed in dependence on the similarity of amplitudes which is for example described by AIS. AIS is an example for an amplitude similarity value.

As described above, the planning CT can be one of the sequence CTs (for example bins) of the 4D-CT or can be generated separately. In the following, examples for this are described.

A scenario is that the Planning CT is one of the bins of the 4DCT scan. Then, for example, the dynamic image is not registered to the treatment volume, that is the planning transformation is not performed. (Remark: A 4DCT scan consists of several volumes/bins, each volume/bin corresponding to a specific respiratory state. Typical labeling: 100% Inhaled, 25% Exhaled, 25% Exhaled, 75% Exhaled, 0% Inhaled, 25% Inhaled, 25% Inhaled, 75% Inhaled).

In case the Planning CT is not part of the 4DCT scan, the planning CT is registered to one of the sequence CTs (by using the planning transformation). The registration procedure and thus the determination of the planning transformation would mean for example a first rigid registration step (concentrating e.g. on bones) yielding a transformation that brings the two in a common coordinates system, followed by a second deformable registration yielding a second transformation which represents a deformation field. The combination of the first and second transformation represents an example for a planning transformation. The question which one of the sequence CTs to be used as undynamic CT:

- If the planning CT was taken during a specific breathing phase one could register the planning CT to the sequence CT which corresponds to the same respiratory state.
- One could also register consecutively to all sequence CTs, and select the most similar sequence CT as the undynamic CT. 'Most similar' could for instance mean selecting the registration that resulted in the fewest deformation around the target area.
- Or as mentioned above, one could select that one of the sequence CTs in which the treatment body part is best discernable.
- Or a combination of the above.

According to an example, the computer implemented method is constituted to display the dynamic DRRs in dependence on selected thresholds. In particular, the computer implemented method can be constituted that a user changes the threshold while getting immediate feedback of the effect of change of threshold by displaying the dynamic DRR. In more detail, this is for example as follows:

The computer implemented method can be constituted to display a page for defining the dynamic DRR. This page provides e.g. a slider enabling the user to set a certain threshold value used by the above described threshold function. A first page can show a very strict threshold resulting in a dynamic DRR nearly containing the treatment body part (target) only. Only voxels following exactly the same trajectory (normalized) are taken into account for rendering. In another page, the threshold can be decreased and thus more voxels—voxels whose trajectory is "very similar" to the target—are used for rendering the dynamic DRR.

With respect to the Figures showing flowcharts, generally, the sequence of the steps is not obligatory but just an example. The only requirement is that data necessary for a determination step have to be acquired before the respective determination.

Different Aspects According to Annex A

According to a first aspect, a computer implemented method for determining a two dimensional DRR is disclosed referred to as dynamic DRR based on a 4D-CT, the 4D-CT describing a sequence of three dimensional medical computer tomographic images of an anatomical body part of a patient, the images being referred to as sequence CTs, the 4D-CT representing the anatomical body part at different points in time, the anatomical body part comprising at least one primary anatomical element and secondary anatomical elements, the computer implemented method comprising the following steps:

acquiring (S10) the 4D-CT;

acquiring (S22, S32, S52, S61) a planning CT, the planning CT being a three dimensional image used for planning of a treatment of the patient, the planning CT being acquired based on at least one of the sequence CTs or independently from the 4D-CT, acquiring (S12) a three dimensional image, referred to as undynamic CT, from the 4D-CT, the undynamic CT comprising at least one first image element representing the at least one primary anatomical element and second image elements representing the secondary anatomical elements;

acquiring (S14) at least one trajectory, referred to as primary trajectory, based on the 4D-CT, the at least one primary trajectory describing a path of the at least one first image element as a function of time;

acquiring (S14) trajectories of the second image elements, referred to as secondary trajectories, based on the 4D-CT;

for the image elements of the undynamic CT, determining (S16) trajectory similarity values based on the at least one primary trajectory and the secondary trajectories, the trajectory similarity values respectively describing a measure of similarity between a respective one of the secondary trajectories and the at least one primary trajectory;

determining (S24, S36, S49, S59, S66,) the dynamic DRR by using the determined trajectory similarity values, and, in case the planning CT is acquired independently from the 4D-CT, further using a transformation referred to as planning transformation from the undynamic CT to the planning CT, at least a part of image values of image elements of the dynamic DRR being determined by using the trajectory similarity values.

According to a second aspect, the computer implemented method according to aspect 1 is disclosed, wherein image values of image elements of the dynamic DRR are determined in dependence on the trajectory similarity values used for determining the image elements.

According to a third aspect, the computer implemented method according to one of the preceding aspects is disclosed,
wherein the undynamic CT is the planning CT (S22, S32); and
wherein the step of determining the dynamic DRR comprises at least one of the following steps a) or b):
a) determining (S24) the dynamic DRR by using the planning CT and the determined trajectory similarity values, wherein, during determination of the dynamic DRR from the planning CT, the trajectory similarity values are considered; or
b) determining (S34) another three dimensional image, referred to as dynamic planning CT by using the planning CT and by changing image values of the planning CT in dependence on the trajectory similarity values, and determining (S36) the dynamic DRR by digitally reconstructing the two-dimensional image from the dynamic planning CT.

According to a fourth aspect, the computer implemented method according to one of the aspects 1 to 3 is disclosed, wherein the step of acquiring (S42, S52) the planning CT independently from the 4D-CT is performed and further comprising the steps of:
determining (S44, S54) the planning transformation;
acquiring (S46, S56) a three dimensional image referred to as similarity image from the determined trajectory similarity values related to the image elements of the undynamic CT;
applying (S48, S57) the planning transformation to the similarity image;
wherein the step of determining the dynamic DRR comprises at least one of the following steps a) or b):
a) determining (S49) the dynamic DRR by using the planning CT and the determined trajectory similarity values, wherein, during determination of the dynamic DRR from the planning CT, image values of the transformed similarity image are considered; or
b) determining (S58) another three dimensional image, referred to as dynamic planning CT by changing image values of the planning CT in dependence on the corresponding trajectory similarity values of the transformed similarity image and determining (S59) the dynamic DRR by digitally reconstructing the two-dimensional image from the dynamic planning CT.

According to a fifth aspect, the computer implemented method according to one of aspects 1 to 3 is disclosed, wherein the step of acquiring (S61) the planning CT independently from the 4D-CT is performed and further comprising the steps of:
determining (S62) the planning transformation; and
wherein the step of determining the dynamic DRR comprises:
determining (S64) a three dimensional image, referred to as dynamic CT by changing image values of at least a part of at least the second image elements of the undynamic CT in dependence on the trajectory similarity values determined for the respective image elements;
determining (S65) a three dimensional image referred to as dynamic planning CT by applying the planning transformation to the dynamic CT; and
determining (S66) the dynamic DRR by digitally reconstructing the two-dimensional image from the dynamic planning CT.

According to a sixth aspect, the computer implemented method according to one of the preceding aspects is disclosed wherein the step of acquiring the primary and secondary trajectories comprises:
acquiring at least the at least one first image element from the undynamic CT;
acquiring the second image elements from the undynamic CT;
determining transformations referred to as sequence transformations which are constituted to transform the undynamic CT to one or more of the sequence CTs and/or to transform one of the sequence CTs to another one of the sequence CTs;
determining the trajectories of the at least one first image element and of at least some of the second image elements by applying the determined sequence transformation to the at least one first image element and the at least some of the second image elements.

According to a seventh aspect, the computer implemented method according to one of the preceding aspects is disclosed, comprising a step of calculating trajectory similarity values as a measure of similarity between trajectories, the step comprising one of the following:
a) determining the respective trajectory similarity values as a function of positional differences between a first position of the at least one first image element defined by the at least one primary trajectory for different points in times and an average of the first position for the different points in time and a positional difference between a second position of a respective one of the second image elements defined by the secondary trajectory for the different times and an average of the second position for the different points in time,
b) determining correlation coefficients describing a correlation between the trajectories
c) determining a normalized correlation describing a normalized correlation between the trajectories
d) determining amplitudes of the trajectories
e) a combination of one of steps a) to c) with d)

According to an eighth aspect, the computer implemented method of one of the preceding aspects is disclosed, wherein an anatomic atlas is used according to at least one of the following steps:
at least one of the second image elements are determined by means of segmentation using the anatomic atlas; or
for one or more of the second image elements no trajectories are determined in dependence on the result of the segmentation achieved by means of the anatomic atlas; or
trajectory similarity values related to one or more of the second image elements are determined in dependence on the result of the determination.

According to a ninth aspect, the computer implemented method according to one of the preceding aspects is disclosed comprising a display of a superposition of the dynamic DDR over a two-dimensional X-ray image and/or aside the two-dimensional X-ray image.

According to a tenth aspect, a computer implemented method for determining a three dimensional image referred to as similarity based on a 4D-CT is disclosed and/or for determining a two-dimensional DRR referred to as dynamic DRR and/or for determining a three-dimensional image referred to as dynamic CT, the 4D-CT describing a sequence of three dimensional medical computer tomographic images of an anatomical body part of a patient which represent the anatomical body part at different points in time, the images being referred to as sequence CTs, the anatomical body part comprising at least one primary anatomical element and secondary anatomical elements, the computer implemented method comprising the following steps:

acquiring the 4D-CT;
acquiring a three dimensional image, referred to as undynamic CT, from the 4D-CT, the undynamic CT comprising at least one first image element representing the at least one primary anatomical element and second image elements representing the secondary anatomical elements;
acquiring at least one trajectory, referred to as primary trajectory, based on 4D-CT, the at least one primary trajectory describing a path of the at least one first image element as a function of time;
acquiring trajectories of the second image elements, referred to as secondary trajectories, based on the 4D-CT;
for the image elements of the undynamic CT, determining trajectory similarity values based on the primary trajectory and the secondary trajectories, the trajectory similarity values respectively describing a measure of similarity between a respective one of the secondary trajectories and the at least one primary trajectory; and
further comprising at least one of the following steps:
a) determining the similarity image by determining the trajectory similarity values to be image values of image elements of the similarity image, referred to as similarity image elements; and
optionally displaying the similarity image; or
b) determining the dynamic DRR by using the determined trajectory similarity values, at least a part of image values of image elements of the dynamic DRR being determined by using the trajectory similarity values; and optionally displaying the dynamic DRR; or
c) determining the dynamic CT by changing image values of at least a part of at least the second image elements of the undynamic CT in dependence on the trajectory similarity values determined for respective image elements and optionally displaying the dynamic CT.

According to an eleventh aspect, the computer implemented method of the tenth aspect is disclosed, comprising the step of acquiring a planning CT, the planning CT being a three dimensional image used for planning of a treatment of the patient, the planning CT being acquired based on at least one of the sequence CTs or independently from the 4D-CT; and
the positions of the similarity image elements correspond to the positions of the image elements of the undynamic CT to which the trajectory similarity values are respectively related;
and optionally, in case the planning CT is acquired independently from the 4D-CT, further determining a transformation from the undynamic CT to the planning CT and applying the transformation to the similarity image before displaying the similarity image.

According to a twelfth aspect, a program is disclosed which, when running on a computer or when loaded into a computer, causes the computer to perform the method according to any one of the preceding aspects and/or to and/or a signal wave, in particular a digital signal wave, carrying information which represents the program, in particular, the aforementioned program in particular comprises code means adapted to perform all the steps of the method of one of the preceding aspects.

According to a thirteenth aspect, a computer-readable program storage medium on which the program according to the twelfth aspect is stored, for example in a non-transitory manner.

According to a fourteenth aspect, a computer is disclosed, the computer comprising the compute-readable program storage medium of the thirteenth aspect.

According to a fifteenth aspect, a system is disclosed, comprising:
the computer (200) of the preceding aspect; and at least one of the following:
a) a display device (201) for displaying the dynamic DRR and an interface for receiving the 4D-CT; or
b) a couch (500) for placing a patient (400) and a treatment device (100) constituted to emit a treatment beam; or
c) an analytical device (310, 320) constituted for generating two-dimensional x-ray images;
d) an analytical device (330) constituted for generating the 4D-CT; or
e) an analytical device (340) constituted for generating the planning CT.

Annex B

The embodiment described in Annex B is directed to determining a transformation (a matching transformation) which (in particular non-rigidly) matches a set of one or more images of an anatomical body structure of a human or animal patient and a set of one or more images of a general anatomical structure of a patient model as described by an anatomical atlas, by matching respective images of the sets to each other, in particular using image fusion, wherein the respective images are associated with the same parameter set (see below) and represent one or more anatomical elements which are matched to each other and correspond to each other.

The anatomical atlas (or "atlas" for short) describes the general anatomical structure of the complete body of a patient model or an object in the patient model or in particular a plurality of objects in the patient model which in particular have a defined positional relationship with respect to each other. An object can comprise one or more anatomical elements. The atlas can be a two-dimensional or three-dimensional (static) atlas or a time-dependent two-dimensional or three-dimensional atlas (a so-called 4D atlas).

The object of this embodiment is to enable the matching transformation to be determined.

A data processing method is advantageously provided for determining the matching transformation. The matching transformation matches a set of one or more images of an anatomical body structure of a patient and a set of one or more images of a general anatomical structure. The set of one or more images of the anatomical body structure of the patient is referred to as the patient image set. The anatomical body structure comprises anatomical elements as sub-structures. The set of one or more images of the general anatomical structure is referred to as the atlas image set. As described below, the atlas image set is determined (in particular generated) in accordance with patient data including one or more parameter sets and on the basis of atlas data. Determining the atlas image set is thus flexible and can be adapted to the particular situation presented by the patient data. The particular situation presented by the patient data is in particular defined by the anatomical elements represented in the patient images, which are referred to as the patient elements, and by at least one parameter set which is associated with the patient image set. A parameter set represents and in particular comprises parameters which have an influence on (generating) an image ("patient image") of an anatomical body structure (by means of an analytical device). In particular, the parameters have an influence on the representation, in particular the visual appearance, of the anatomical body structure (in particular the anatomical elements) in the (patient) image. The parameters are therefore also referred to as "representation parameters". The parameter set represents and in particular comprises parameters which describe the type of an analytical device and in particular measurement parameters of the analytical device. One example of a representation parameter is a particular image modality used for generating the patient image set. One particular example of a representation parameter is a DICOM (Digital Imaging and Communications in Medicine). The patient image set can of course also or instead comprise patient images associated with other representation parameters, in particular different image modalities such as computer tomography (CT) and magnetic resonance (MR). The image modalities are in particular further specified by means of measurement parameters used for adjusting the analytical device, such as the voltage or magnetic field strength. The measurement parameters are also an example of representation parameters. There may be many different parameters involved when generating an analytical image of an anatomical structure by means of an analytical device, all of which constitute examples of representation parameters. The representation of patient elements in patient images can for example depend on the magnetic field strengths used during MR, the repetition time, the echo time, the inversion time, the flip angle, etc.

In the field of medicine, imaging methods (imaging modalities) are used to generate image data (for example, two-dimensional or three-dimensional image data) of anatomical structures (such as soft tissues, bones, organs, etc.) of the human body. The term "medical imaging methods" is understood to refer to imaging methods, advantageously apparatus-based imaging methods (so-called medical imaging modalities, in particular radiological imaging methods), such as for instance computer tomography (CT) and cone beam computer tomography (CBCT; in particular, volumetric CBCT), x-ray tomography, magnetic resonance tomography (MRT or MRI=magnetic resonance imaging), in particular T1-weighted MRI, T2-weighted MRI, PET (with and without contrast agent), conventional x-ray, sonography and/or ultrasound examinations. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body.

In order to determine the geometry and/or position of an anatomical body structure, analytical devices such as x-ray devices, CT devices or MRT devices are used to generate analytical images (such as x-ray images or MRT images) of the anatomical body structure. Analytical devices in particular use imaging methods and are in particular devices for analysing a patient's body, for instance by using waves and/or radiation and/or energy beams, in particular electromagnetic waves and/or radiation, ultrasound waves and/or particle beams. Analytical devices are in particular devices which generate images (for example, two-dimensional or three-dimensional images) of the patient's body (in particular, the anatomical body structure of the patient's body) by analysing the body. Analytical devices are in particular used in medical diagnosis, in particular in radiology.

The above-mentioned parameter sets represent and in particular comprise one or in particular more (representation) parameters (such as the type of analytical device and magnetic field strength in MRT devices or the voltage in CT devices) which reflect (and in particular are) parameters which have an influence on the representation of the patient elements in the patient image, in particular when generating the patient image. Thus, each of the patient images is associated with a particular parameter set. Different patient images can be and in particular are associated with different parameter sets. The parameters which the parameter sets comprise in particular represent parameters which have an influence on the representation of the patient elements in the patient images when the images are generated. Examples of influences on representation include influences on the image values which represent the anatomical elements (such as for instance influences on a grey value which represents the anatomical element or influences on the position of an image value in a color space which represents the anatomical element). Other examples include influences on contrast, image value range, gamut, etc.

The method in accordance with this embodiment in particular comprises the step of acquiring atlas data which contain information describing the general anatomical structure and in particular the representation of the general anatomical structure in an analytical image. This information is referred to as "element representation information". The element representation information describes the representation of the anatomical elements (referred to as "atlas elements") of the general anatomical structure. This representation corresponds to the representation of the anatomical elements in an image which is generated by means of an analytical device from a patient having an anatomical structure which is identical to the general anatomical structure. The influence of the generating process (for example, scanning parameters such as the type of analytical device used to generate the image and/or the measurement parameters which are set, in particular adjusted, on the analytical device and have an influence on the representation) on the representation of the one or more anatomical elements is represented by the parameter set. The atlas data, in particular a determination rule (see below) in combination with the parameter set, allow the atlas image to be determined.

The method also comprises the step of acquiring the patient data which include the patient image set and one or more of the parameter sets. Preferably, only one of the one or more parameter sets is respectively associated with one of the one or more patient images of the patient image set.

The general anatomical structure can be the anatomical structure of a complete body or the anatomical structure of only a part of the body. The general anatomical structure preferably comprises a plurality of atlas elements. The atlas elements which the general anatomical structure comprises are preferably not assigned a particular representation data set. The representation data sets can for instance describe a grey value of an atlas element. Since the atlas elements of the general anatomical structure are preferably not assigned a particular grey value, these atlas elements are also referred to here as "white atlas elements".

The anatomical structure described by the patient images can be a description of the anatomical structure of the complete body or a description of the anatomical structure of only a part of the body. The term "part" as used here can encompass either the term "complete" or the term "less than complete", i.e. only partial (within the common meaning of this term). Data (referred to as "correspondence part data") are preferably acquired which describe the part of the general anatomical structure which corresponds to the anatomical structure represented by the patient images and which is to be matched. If the entire general anatomical structure described by the atlas data is to be matched, then correspondence part data are not necessary. The (different)

patient images of the patient image set preferably each describe at least approximately the same part of the anatomical structure of a patient's body. The (different) patient images of the patient image set preferably cover the description of at least one particular part of the body, i.e. at least one particular part of the body is reflected in all of the patient images of the patient image set, which is then referred to as the "common part" and comprises common anatomical elements. The matching transformation is preferably determined for at least the part of the patient images which reflect the common part of the body. The correspondence part data can comprise data (referred to as "correspondence element data") which describe the white atlas elements for which a matching transformation is to be determined. The white atlas elements for which the matching transformation is to be determined are referred to as "corresponding elements" and can be acquired for instance by receiving indication information (from a user) which indicates which white atlas elements are corresponding elements. Alternatively or additionally, the correspondence part data can be determined for example by performing a rigid transformation which rigidly matches patient images and atlas images which are respectively associated with the same parameter set, in particular without deforming the atlas elements represented in the atlas image and without deforming the patient image. Merely scaling and/or rotating the atlas images and patient images in order to achieve rigid matching is not considered to constitute deformation. In order to perform rigid matching, atlas spatial information (referred to as "coarse atlas spatial information") is preferably used which describes the general anatomical structure in less detail than the atlas spatial information used for determining the atlas images, in order to reduce the data processing load. Additionally or alternatively, the correspondence part data can describe the part (referred to as the "atlas part") of the general anatomical structure (the complete structure or only a particular part of it) which is to be used for the matching transformation and in particular can describe the part of the anatomical structure (referred to as the "patient part") represented in the at least one patient image (i.e. all of the anatomical structure or only a part of it) which is to be used for the matching transformation. At least one preliminary atlas image is then generated which represents the atlas part. Preliminary rigid matching is then performed, without deforming the atlas elements, in which the at least one preliminary atlas image and the patient part of the anatomical structure represented in the at least one patient image are matched to each other. Rigid matching in particular allows a common reference system to be established for all of the atlas images determined. The common reference system is in particular used to determine the matching transformation. This common reference system facilitates the implementation of "coupled deformation" as described below.

The data processing method of this embodiment in particular comprises the above-mentioned step of determining the correspondence part data, in particular the corresponding elements. The term "corresponding" as used here means in particular "anatomically the same", in particular "representing the same anatomical part" which can be understood to be a part of a patient's body which is present in a plurality of different patient's bodies and in particular belongs to the same representation classes (see below for the definition of representation classes) and/or consists of the same material and/or is located at least approximately at the same location relative to other anatomical elements and/or has a similar geometry (size and/or shape) in a plurality of different patients.

The atlas data preferably comprise atlas spatial information which spatially describes the general anatomical structure and in particular the white atlas elements. The spatial information can comprise only one set of static spatial information, i.e. spatial information which does not change over time and only provides one set of spatial properties for the general anatomical structure, or can comprise a plurality of sets of static spatial information which respectively describe the spatial properties of the general anatomical structure in different states, for instance at different points in time during for example a vital movement such as for example the breathing cycle. In particular, the spatial information describes the spatial properties, i.e. the relative position, of white atlas elements within the general anatomical structure with respect to each other and/or the geometry (size and/or shape) of the atlas elements and is preferably used to determine the spatial properties (i.e. the position and/or geometry) of the atlas elements represented in the atlas images.

A vital movement is a movement of parts of the body due to vital functions of the body, such as for example breathing and/or the heart beat. The term "vital movement" covers any kind of movement of the body which is performed unconsciously and in particular controlled by the brain stem.

The above-mentioned plurality of sets of spatial properties of the general anatomical structure can also describe different movement or posture states of the patient, such as the patient running, walking, standing or lying down. It can also cover different pathological states of a patient, such as a patient with an infection or tumour(s) in particular parts of the body, or particular states of a patient during surgery, such as a patient with an exposed skull resulting in a brain shift (which can in turn depend on the positioning of the head). The term "posture" as used here refers in particular to different positions of the extremities of the body, such as for example with the hands raised or lowered.

The element representation information describes a plurality of representation data sets, wherein "plurality" as used here means a discrete number of representation data sets (as for example described by a table) or a continuous multitude of representation data sets (as for example described by a function). Preferably, both the atlas spatial information and the element representation information are used to determine the atlas images. The representation data sets contain information describing representations of the plurality of atlas elements in the atlas images which are to be determined. In particular, the element representation information comprises information on the visual appearance of the atlas element (in an atlas image) and in particular does not include the above-mentioned spatial information. The representation information describes for example an image value (for instance, a grey value) for the respective atlas elements.

The same patient elements can be represented differently in different patient images, depending on the parameter sets. Correspondingly, the element representation information preferably does not comprise just one representation data set to be determined for respective white atlas elements but rather a plurality of representation data sets to be determined for respective white atlas elements, wherein each of the plurality of representation data sets (for each of the white atlas elements) is in particular respectively associated with one of the plurality of parameter sets. A white atlas element to which a representation data set is assigned is referred to here as a "grey atlas element", i.e. a plurality of different grey atlas elements can be determined on the basis of the white atlas elements and a plurality of different representation data sets. It is possible, on the basis of the element representation information, to determine the grey atlas elements (i.e. the representation and in particular visual appearance of a corresponding element) in an atlas image in accordance with the parameter set of a patient image which is to be matched to the atlas image. In other words, the grey atlas elements in an atlas image are determined on the basis of the parameter set of the patient image.

The patient data consist of the patient image set, i.e. one or more patient images associated with one or more parameter sets, and a description of the one or more associated parameter sets. The parameter sets associated with the patient data are preferably identical to one or more of the plurality of parameter sets of the atlas data for which the determination rule describes a determination of the representation data sets, in order to allow for a straightforward application of the determination rule. If such identity does not obtain, then the parameter set of the atlas data which is most similar to the parameter set of the patient data is preferably selected, in order to be able to apply the determination rule.

As mentioned above, the one or more atlas images are determined on the basis of the atlas data and the patient data. The one or more atlas images respectively represent at least a part of the general anatomical structure (i.e. the complete general anatomical structure or only a part of it). The respectively determined one or more atlas images represent a part of the general anatomical structure in accordance with the part of the spatial information which relates to said part of the general anatomical structure. In other words, the spatial information on the general anatomical structure, in particular the part of the spatial information which relates to atlas elements represented in the set of atlas images, is used to determine the set of atlas images. In order to determine the representation of the general anatomical structure in the set of atlas images, the representation data sets which are part of the description of the atlas data are specifically used. The determination rule described by the atlas data is applied in order to determine the representation data sets which are specifically to be used to determine the representation of the atlas elements. The determination rule refers to the parameter sets associated with the one or more patient images, i.e. the determination rule allows the representation data sets to be determined in accordance with the associated one or more parameter sets. The representation data sets preferably depend not only on the associated parameter sets but also on the corresponding elements. In short, the representation data sets are thus determined on the basis of the corresponding elements and the associated one or more parameter sets by using the determination rule described by the atlas data. The element representation information preferably describes a plurality of representation data sets (two, three or more sets) for respective white atlas elements (in particular, for each white atlas element), and the determination rule describes how one of the plurality of representation data sets is selected for a respective white atlas element in accordance with the parameter set associated with the patient image to which the atlas image is to be matched. Each selection results in a determined grey atlas element. The determination rule is for example implemented using a reference table. Alternatively, a function is used, which is in particular dependent on a number (plurality) of parameters (referred to as "scanning parameters"). A grey value relationship is for example calculated on the basis of scanning parameters, such as for example the repetition time, magnetic field strength, etc., and tissue-dependent scanning parameters such as for example the T1 relaxation time, T2 relaxation time and proton density, by using a formula. The function can thus be used to calculate the representation data set (for example, a grey value relationship) in accordance with scanning parameters. The function is in particular designed to describe a continuous multitude of possible solutions for a representation data set (i.e. spanning the range of possible solutions), and the representation data set is calculated in accordance with the determination rule by selecting from this multitude of possible representation data sets. The determination rule in particular describes the scanning parameters which are to be selected and how they are to be used and the function for calculating the representation data set.

The method (in particular, a data processing method) in accordance with this embodiment also includes the step of determining a matching transformation for matching the patient image set and the atlas image set to each other. This matching transformation is referred to as an "AP transformation" (short for "atlas-patient transformation") if the atlas image is matched to the patient image. The matching transformation is determined by matching a respective image of the atlas image set and a respective image of the patient image set to each other. Matching can be performed by image fusion, which in particular uses similarity measures (see below) in order to find a matching transformation which optimally matches the respective images. The matching transformation can match one or more images of the atlas image set and one or more images of the patient image set. The respective image of the atlas image set and the respective image of the patient image set which are matched by the matching transformation are in particular associated with the same parameter set. Thus, the matching transformation is preferably determined by matching images which are associated with the same parameter set. The AP transformation in particular describes a deformation of atlas elements which is similar for all images of the atlas image set, wherein the images of the atlas image set are in particular associated with different parameter sets. This aspect is discussed in more detail below. The deformation is in particular similar if it is caused at least primarily by the deviation of the patient's anatomical structure from the general anatomical structure described by the atlas data and if the spatial properties of the patient images are similar. Any spatial distortion caused when generating the patient images is therefore preferably removed before the patient images and atlas images are matched.

In this application, the terms "image morphing" and/or "elastic fusion" are also used as an alternative to the term "image fusion", but with the same meaning.

Elastic fusion transformations (for example, image fusion transformations) are in particular designed to enable a seamless transition from one data set (for example, a first data set such as for example a first image) to another data set (for example, a second data set such as for example a second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. One or more (numerical) optimisation algorithms are preferably applied in order to find the transformation which results in an optimum degree of similarity. The degree of similarity is preferably measured by way of a measure of similarity (also referred to in this document as a "similarity measure"). The parameters of the optimisation algorithm(s) are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions in the one of the first and second images which is to be transformed, and the tips of the vectors lie at the corresponding voxel positions in the transformed image. A plurality of these vectors are preferably provided, for instance more than twenty or a hundred or a thousand or ten thousand, etc. There are preferably (other) constraints on the transformation (deformation), in particular in order to avoid pathological deformations (such as for instance all the voxels being shifted to the same position by the transformation). These constraints in particular include the constraint that the transformation is regular, which in particular means that a Jacobian determinant calculated from a matrix of the deformation field (in particular, the vector field) is larger than zero. The constraints also in particular include the constraint that the transformed (deformed) image is not self-intersecting and in particular that the transformed (deformed) image does not comprise faults and/or ruptures. The constraints also in particular include the constraint that if a regular grid is transformed at the same time as the image and in a corresponding manner, the grid is not allowed to interfold at any of its locations. The optimisation problem is in particular solved iteratively, in particular by means of an optimisation algorithm which is in particular a first-order optimisation algorithm, in particular a gradient descent algorithm. Other examples of optimisation algorithms include optimisation algorithms which do not use derivations, such as the downhill simplex algorithm, and algorithms which use higher-order derivatives, such as Newton-like algorithms. The optimisation algorithm preferably performs a local optimisation. If there are a plurality of local optima, then global algorithms such as simulated annealing or genetic algorithms can be used. In the case of linear optimisation problems, the simplex method can for instance be used.

In the steps of the optimisation algorithms, the voxels are in particular shifted by a magnitude in a direction, such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between neighbouring voxels. Due in particular to a high number of (iteration) steps, large deformations can be implemented.

The determined elastic fusion transformation (for example, a matching transformation) can in particular be used to determine a degree of similarity (also referred to as a "measure of similarity" or "similarity measure") between the first and second data sets (images). Optimum matching can for instance be defined (predetermined) as matching which results in at least a predetermined measure of similarity. To this end, the deviation between the elastic fusion transformation and an identity transformation is determined. The degree of deviation can for example be calculated by determining the difference between the determinant of the elastic fusion transformation and the identity transformation. The higher the deviation, the lower the degree of similarity. The degree of deviation can thus be used to determine a measure of similarity.

A measure of similarity can in particular be determined on the basis of a determined correlation between the first and second data sets.

The matching transformation referred to as an AP transformation preferably describes a matching transformation which matches one or more atlas images to one or more patient images, i.e. the AP transformation is preferably applied to atlas images in order to determine matched atlas images.

In an AP transformation, the spatial information (position and/or geometry) of the patient elements represented in the patient image preferably remains fixed, while the spatial information (position and/or geometry) of the atlas elements in the atlas images is changed so as to match the spatial information of the patient elements in the patient images when the AP transformation is applied. The image which results from applying the AP transformation to the atlas image is referred to as the matched atlas image. The AP transformation is preferably designed to maintain the segmented structure of the atlas, i.e. to maintain the corresponding elements such that deformed corresponding elements are shown in the matched atlas image. Preferably, the representation of the deformed corresponding elements in the matched atlas image respectively corresponds to the representation data sets determined for the respective (unmatched) corresponding elements, i.e. the matching transformation preferably only acts on the spatial information and not on representation information described by the representation data sets, in accordance with this embodiment. In accordance with another embodiment, the representation information determined by the representation data set is adapted in view of the representation of patient elements or patient images. In accordance with yet another embodiment, at least some of the representation of at least some of the grey atlas elements is determined on the basis of the representation of patient elements, particularly if it is not possible to determine representation data sets. The patient elements are preferably identified by applying the AP transformation, which allows the patient image to be segmented into patient elements. The representation of the patient element is then determined and used in turn to determine the representation of the matched grey atlas elements of the matched atlas image.

In accordance with an alternative embodiment, the matching transformation is referred to as a PA transformation and preferably describes a matching transformation which matches one or more patient images to one or more atlas images, i.e. the spatial information (position and/or geometry) of the atlas elements represented in the atlas images remains fixed, while the spatial information (position and/or geometry) of the patient elements in the patient images is changed to match the spatial information of the atlas images in the atlas images when the PA transformation is applied. This transformation can in particular be used to improve atlas data which are to be improved (improved atlas data are referred to as "model data") by adding information from patient images to the model data. The PA transformation can be used as described in another application, filed by the same applicant, entitled "Determining an Anatomical Atlas" (WO 2014/063745 A1). The PA transformation corresponds to the PM transformation discussed in said application and is used to improve the atlas data by means of patient data.

The step of determining the atlas image set preferably comprises the step of determining the representation data sets for the corresponding elements. The element representation information preferably describes a plurality of representation data sets for at least one (in particular, two or more) of the white atlas elements, preferably most of the white atlas elements and in particular all of the white atlas elements, i.e. the element representation information allows one of the respective plurality of representation data sets to be determined for a white atlas element in accordance with one of a respective plurality of different parameter sets by using the determination rule.

If a particular parameter set is described by the patient data for a particular patient image, then representation data sets for each of the corresponding elements are preferably determined in accordance with said particular parameter set. In particular, one of the representation data sets is selected from the plurality of representation data sets described by the element representation information for each of the corresponding elements by using the determination rule which in particular describes the representation data set which is to be selected for each of the corresponding elements in accordance with the particular parameter set described by the patient data for said particular patient image. If the patient data describe more than one parameter set and more than one patient image, then this process is preferably performed for each of the patient images. Preferably, more than one representation data set is selected from the plurality of representation data sets described by the element representation information in accordance with the determination rule and the plurality of parameter sets described by the patient data for more than one patient image, in order to allow more than one atlas image to be determined, i.e. for each of the corresponding elements. For each of the corresponding elements, the number of selected representation data sets preferably corresponds to the number of patient image sets if there is a different representation of the atlas element for each of the parameter sets described by the patient data. The determination rule preferably refers to the same parameter set for all of the corresponding elements of an atlas image, i.e. the parameter set of the patient image to which the atlas image is to be matched (or vice versa). Thus, an atlas image is preferably associated with only one parameter set.

The determination rule in particular comprises an assignment rule for respectively assigning one representation data set to one corresponding element for each different parameter set. The assigned representation data set describes the representation of the corresponding element in the atlas image associated with one of the different parameter sets. The assignment rule preferably depends on the parameter set which is associated with the patient image which includes the patient element to which the corresponding element is to be matched.

In accordance with one embodiment of Annex B, the determination rule comprises assignment rules for (all of) the respective white atlas elements, so that there is an assignment rule for each of the white atlas elements to be matched, i.e. for each of the corresponding elements. In accordance with preferred embodiments of Annex B, the assignment rule is simplified by not providing an assignment rule for each of the atlas elements but rather for classes of atlas elements, referred to as representation classes (or also "tissue classes"), and preferably assigning (each of) the respective atlas elements to one of the representation classes. This reduces the processing load of the data processing method. For each of the white atlas elements belonging to the same respective representation class, the same representation data set is preferably determined for each of the respective parameter sets. In other words, different grey atlas elements belonging to the same representation class are represented in an atlas image in accordance with the same representation data set, irrespective of the individual parameter set associated with the atlas image which includes the different grey atlas elements. Further details with respect to representation classes are given below.

The representation (representation properties) of the corresponding elements in the one or more atlas images is/are determined on the basis of the determined representation data sets. Each of the corresponding elements represented in the one or more atlas images is in particular represented in accordance with the assigned representation data sets. All the corresponding elements of a respective atlas image are preferably associated with the same parameter set.

The representation data sets can represent rules for defining absolute values of representation, such as an absolute image value (for example, an absolute grey value or an exact position in a colour space) which is in particular used for the whole space occupied by a grey atlas element. The representation data sets can also describe relative rules for representation (in particular, for the representation of image values), such as for instance that one particular atlas element should be represented with a lower grey value than another particular atlas element or that a colour value is shifted in a particular direction from one atlas element to another. The parameter sets can also represent incomplete information (at least for some of the corresponding elements) which does not allow a representation data set to be determined directly for all of the corresponding elements (for example by simply using a reference table). The parameter set can for example be incomplete in that it is not known whether a contrast agent was injected into the patient before the patient image was generated or not. The representation of a corresponding element which can be influenced in terms of its representation by a contrast agent will then be uncertain. Flexibility in determining the representation of one or more of the corresponding elements is then desirable. This is preferably achieved by performing a first matching process (using image fusion) and comparing the matched atlas images with the patient images. The first matching process relies in particular on spatial properties only, in particular with respect to the corresponding elements for which a representation data set has not yet been determined. This first matching process in particular allows the patient image to be segmented into patient elements. On the basis of the comparison, the representation of the corresponding elements is changed so as to be closer to the representation of the corresponding patient elements in the patient images. In the next step, the matching transformation is correspondingly adapted such that applying the matching transformation to the atlas images (i.e. a second matching process) results in matched atlas images in which the representation of corresponding elements is more similar to the representation of the corresponding patient elements in the patient images than it was after the first matching process but before the second matching process. Thus, the determination rule preferably uses information on the representation of the patient elements in the patient images in order to determine the representation of the matching elements. This information is referred to as patient image representation data, which in particular describe the image values which represent the patient elements.

The term "similar" as used here generally covers the two meanings of "similar but not identical" and "similar and identical", i.e. the term "similar" in particular also covers the term "identical". The above-mentioned similarity measure can be used to quantify the term "similar", and a predetermined threshold for the similarity measure can be applied in order to differentiate between what is similar and what is not similar.

As mentioned above, the patient images can be associated with different parameter sets, wherein anatomical elements of the patient represented by one or more of the patient elements in the patient images associated with different parameters are in particular identical. If, for example, a CT image and an MR image of a patient element (for example, the lung) are provided, then a matching transformation which deforms an atlas element to match a patient element associated with a parameter set and a matching transformation which transforms the atlas element to match the patient element represented in another patient image associated with another parameter set will perform a similar spatial deformation if there is no geometric distortion incurred by the analytical devices or if the incurred distortion is similar in each case. The matching transformation is preferably designed to match one of the atlas images to one of the patient images associated with one of the parameter sets and another of the atlas images with another of the patient images associated with another of the parameter sets. Determining the part of the matching transformation which matches one of the atlas images and one of the patient images, both of which are associated with the same parameter set, to each other preferably involves taking into account information on another part of the matching transformation which matches another of the atlas images and another of the patient images, which are associated with another of the associated parameter sets, to each other. Thus, information resulting from different matching processes (relating to different parameter sets) is used reciprocally in order to improve the quality of matching. The reciprocally used information is in particular spatial information. Preferably, a spatial correlation between patient images associated with different parameter sets is determined before this reciprocal information is used. Atlas images and patient images are for example rigidly matched to each other, in particular in order to establish a common spatial reference system for all the patient images, in particular so that deformation vectors relating to different matching processes can be determined. As mentioned above, the matching transformation preferably performs different matching processes, i.e. matches atlas images and patient images associated with different parameter sets, wherein the images comprises common patient elements (of the same patient).

The matching transformation (in particular, the AP transformation) is generally determined in such a way that (first) spatial information on matching one of the atlas images (a first atlas image) and one of the patient images (a first patient image) to each other (in particular, information on matching one of the atlas images to one of the patient images) is used to determine how another of the atlas images (a second atlas image) and another of the patient images (a second patient image) are matched to each other. The former matching process is preferably described by a first part of the matching transformation, while the latter matching process is preferably described by a second part of the matching transformation. The first atlas image and first patient image which are subjected to the former (first) matching process are associated with a first parameter set, while the second atlas image and second patient image which are subjected to the latter (second) matching process are associated with a second (different) parameter set. Thus, the first spatial information is used as a basis for determining the second part of the matching transformation (in particular, the second part of the AP transformation) which matches another of the atlas images and another of the patient images to each other, i.e. one part of the matching transformation which relates to one of the parameter sets uses information (in particular, spatial information) from another part of the matching transformation which performs matching with respect to another parameter set.

As mentioned above, the spatial deformation represents an example of the information used in this way. The information can in particular be used reciprocally, i.e. reciprocal information is used. In order to apply the reciprocal information, the matching transformation is varied on the basis of the reciprocal information, and the quality of the matching transformation for different variations is determined. Preferably, the variation which results in the highest-quality matching transformation is selected. In order to determine the quality of the matching transformation, the quality of a matching process between a patient image and an atlas image is in particular determined. The matching quality can be determined on the basis of the degree of similarity (for example, quantified by the similarity measure) between the images after matching has been performed. If the matching transformation is determined by applying the same spatial changes (change in position and/or geometry) to one of the first atlas image and first patient image (in particular the first atlas image in the case of AP transformations) and one of the second atlas image and second patient image (in particular the second atlas image in the case of AP transformations), then the deformation can be varied by varying the transformation, and the kind of transformation which is determined as the matching transformation is the one which on average (for example, by averaging a similarity measure determined for a first AP sub-transformation APT1 and a similarity measure determined for a second AP sub-transformation) results in the greatest similarity between the respective atlas images and the respective patient images.

In accordance with one embodiment, the matching transformation comprises parts which are distinct matching sub-transformations. The matching sub-transformations are preferably coupled, since spatial information—in particular, properties of the matching sub-transformations (such as the deformations determined by the matching sub-transformation)—have an influence on each other. The respective matching sub-transformations respectively match the atlas images associated with a respective associated parameter set and a respective patient image associated with the same respective associated parameter set, i.e. each matching sub-transformation is directed to a matching process relating to one of the parameter sets. The matching sub-transformations are in particular AP sub-transformations which respectively match one atlas image to one patient image. The matching sub-transformations are in particular coupled in that they each influence the determination of the other. One of the matching sub-transformations is in particular determined on the basis of determining another of the matching sub-transformations. This coupling is in particular based on a spatial correlation between atlas images and patient images associated with different parameter sets. As mentioned above, the correlation can in particular be established by means of rigid transformations applied with respect to the different parameter sets. The spatial correlation between the atlas images in particular is preferably known, since they represent the same (part of) the general anatomical structure, i.e. the same spatial information. The representation of the structure (in particular its visual appearance) in the atlas images can differ in accordance with the associated parameter sets.

As mentioned above, representation classes are preferably used to classify the atlas elements. Each atlas element is preferably assigned to one of the representation classes. The representation classes define the representation of the atlas elements for different parameter sets. The atlas elements are preferably assigned to the representation classes surjectively. The determination rule preferably uses the assignment between atlas elements and representation classes to describe an assignment between atlas elements and representation data sets. This advantageously simplifies the assigning process, since a number of in particular different atlas elements (such as for example one, two or more atlas elements, in particular different atlas elements) can preferably be assigned to the same representation class. Preferably, each of the representation data sets describes the representation of one particular atlas element which is associated with one parameter set. If particular atlas elements belong to the same representation class, then the same representation data set is determined for all of these particular atlas elements by the determination rule, providing they are associated with the same parameter set. If one or more representation data sets is/are respectively associated with one or more parameter sets for a particular representation class, then the one or more representation data sets represent a subset of a plurality of representation data sets. The subset is defined within the particular representation class and is selected by the determination rule for an atlas element belonging to said particular representation class. Thus, a representation class represents a subset of the representation data sets. The determination rule assigns a particular representation data set of the subset to an atlas element belonging to the representation class in accordance with the parameter set. In other words, the respective representation classes represent respective subsets of the plurality of representation data sets, and for each representation class, there is a characteristic bijective assignment between the representation data sets of the subset and the parameter sets, i.e. for each representation class, the determination rule assigns one representation data set (of the subset) to an atlas element belonging to the representation class, wherein the assignment is made in accordance with the parameter set associated with the patient image comprising the patient element to which the atlas element is to be matched.

As mentioned above, the representation data sets describe the representation (also referred to as the "representation property"), in particular the visual appearance, of anatomical elements in an atlas image. In particular, the representation data set can for example describe (as an example of a representation property) image values, in particular a single image value for a particular anatomical element or a single average value for the region (in particular, area) occupied by the anatomical element. The image value can for example be a grey value, an intensity value, a colour value, a value in a colour space, etc. The representation data set can also describe (as an example of a representation property) a lower limit and/or upper limit of the image values, for instance a range of grey values or a range in the gamut of the colour space for a particular anatomical element (in particular, for each of the representation classes). The representation data set in particular describes (as an example of a representation property) a relationship between image values of different anatomical elements, for instance that a grey value is higher in one anatomical element than in another anatomical element. Any such description refers of course to a particular parameter set. With respect to another parameter set, the relationship may be different. The relationship can of course also be in the colour space and consist for instance of the fact that the intensity is higher for one anatomical element than for another or that there is a shift in the colour space in a particular direction if the image value of one anatomical element is compared with the image value of another anatomical element. Aside from the aforementioned average of image values for the anatomical elements (associated with particular parameter sets), a standard deviation from the average image values can be described by the representation data sets. Structures of modulations of the image values can also be described (as an example of a representation property) for the anatomical elements by the representation data sets. Spatial modulations of image value variations within the anatomical element can for example be described (for instance by means of DCT coefficients). Characteristics of transitions between representations of different anatomical elements can also be described (as an example of a representation property). The transition from a bone structure to a soft tissue structure is for example different in an x-ray image as compared to an MRT image. In particular, the representation property does not comprise spatial information, hence the representation data set in particular does not describe spatial information. The representation property is also referred to as "representation information".

The above-mentioned representation classes are in particular substance classes (also referred to as "tissue classes"), since anatomical elements which are of a similar substance can be represented by the same subset of representation data sets, wherein each member of the subset is respectively assigned to one of the parameter sets. An anatomical element consisting mainly of a particular substance (for instance, fat or bone) will for example have the same representation (in particular, visual appearance), irrespective of where the anatomical element is located in the patient's body. Thus, in accordance with one embodiment, information on the substance of an anatomical element is used to assign the anatomical element to one of the representation classes.

As mentioned above, the atlas data comprise atlas spatial information which describes spatial information (i.e. position and/or geometry) for the general anatomical structure. In accordance with one embodiment, the spatial information is static, i.e. the position and/or geometry of the general anatomical structure is fixed for all elements. In accordance with a preferred embodiment, the spatial information is flexible, i.e. the position and/or geometry of one or more of the atlas elements is flexible. The term "flexible" as used here means in particular that a variation in the position and/or geometry is allowed in order to improve the quality of the matching process. As mentioned above, the matching quality can be measured by determining the degree of similarity (by means of a similarity measure) between the element (for example, an atlas element) which is subjected to the matching transformation and the element (for example, a patient element) to which the transformed element is to be matched.

There are in particular anatomical elements which can significantly vary in terms of their position from patient to patient. The flexibility information can accordingly include a statistical probability for different positions and/or geometries of the anatomical element. The position of the kidney can for example vary from patient to patient. For the purposes of this document, an organ is not generally an anatomical element but can comprise different anatomical elements, since an organ can consist of regions occupied by different types of substances. Conversely, an anatomical element may be larger than an organ. The brain stem, for example, is only part of the white matter but is not clearly separated from other parts of the white matter. In accordance with one embodiment, organs which cannot be clearly differentiated from other organs, such as the brain stem, are identified as a sub-structure within an anatomical element. Preferably, an anatomical element consists at least predominantly of one or more substances which manifest themselves through the same representation property in analytical images associated with different parameter sets, i.e. the one or more substances belong to the same representation class.

The above-mentioned flexibility information which can be part of the atlas spatial information is in particular used as a constraint when determining the matching transformation. The anatomical variability of the position of anatomical elements as mentioned above represents one reason for the use of flexibility information. Another reason is changes in the position of anatomical elements due to intentional changes in position brought about by the patient or a user (such as for example medical staff). The arms and legs of a patient can for example adopt different positions with respect to the patient's torso. The variability of these possible positions, in particular due to the variability of the extremities of the patient's body, can also form a basis for the flexibility information. Another reason for using flexibility information can be the different positions of organs (and therefore anatomical elements) due to the different sizes of the lung(s) during a breathing cycle or due to the heart beat or other, unintentional movements.

Anatomical variability can also be due to a pathological change in the patient's body. The development of a tumour can for example shift parts of the brain.

The flexibility information can in particular also comprise a constraint with respect to positions and positional changes such as rotations. A rotation of one vertebra with respect to another by more than 180° is for example anatomically impossible and can accordingly be excluded by means of the flexibility information.

The expression "acquiring data" encompasses in particular (within the framework of a data processing method) the scenario in which the data are determined by the data processing method or program. Determining data in particular encompasses measuring physical quantities and transforming the measured values into data, in particular digital data, and/or computing the data by means of a computer and in particular within the method of the invention. The meaning of "acquiring data" also in particular encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. In particular, the acquiring step does not involve an invasive step which would represent a substantial physical interference with the body requiring professional medical expertise to be carried out and entailing a substantial health risk even when carried out with the required professional care and expertise. Acquiring—in particular, determining—data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

Within the framework of Annex B, computer program elements can be embodied by hardware and/or software (this includes firmware, resident software, micro-code, etc.). Within the framework of Annex B, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular, a random access memory or RAM) for storing data used for and/or produced by executing the computer program elements. Within the framework of Annex B, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The method in accordance with Annex B is preferably at least partly executed by a computer, i.e. all the steps or merely some of the steps (i.e. less than the total number of steps) of the method in accordance with Annex B can be executed by a computer.

The object stated at the beginning is achieved by the subject-matter of any of the "aspects" of Annex B denoted below. Advantages, advantageous features, advantageous embodiments and advantageous aspects of Annex B are disclosed in the following and also contained in the subject-matter of the "aspects" of Annex B.

Different advantageous features can be combined in accordance with Annex B wherever technically sensible and feasible. A feature of one embodiment which is functionally identical or similar to a feature of another embodiment can in particular replace said latter feature. A feature of one embodiment which supplements a function of another embodiment can in particular be added to said other embodiment.

Pathological Changes

As mentioned above, the method described in Annex B can also be applied if the patient images describe an anatomical structure which exhibits pathological changes. This can be handled using the above-described flexibility information. In accordance with another embodiment described in the following, parameters referred to as "patho parameters" are used to determine and in particular select information on the general anatomical structure which fits the anatomical structure of the patient which exhibits pathological changes. More specifically, the patho parameter specifies and in particular classifies the pathological changes to the anatomical structure, i.e. the general anatomical structure as compared to a healthy patient and the anatomical structure of the patient as compared to a healthy patient. The patho parameter in particular specifies the anatomical structure in accordance with a medical classification system such as the TNM Classification of Malignant Tumours. The data processing method is preferably embodied by the following method:

A data processing method for determining a matching transformation for matching an image of an anatomical body structure of a patient, referred to as a patient image, and an image of a general anatomical structure, referred to as an atlas image, wherein both the anatomical body structure of the patient and the general anatomical structure exhibit pathological changes and the patient image is associated with one of a plurality of different parameters which are referred to as patho parameters and specify the pathological changes in accordance with a classification, the method comprising the following steps performed by a computer:

acquiring atlas data which contain information on a description of a plurality of images of the general anatomical structure for a plurality of patho parameters and in particular spatial meta information on the pathological changes; and acquiring patient data, comprising the sub-steps of
acquiring the patient image, and
acquiring the patho parameter associated with the patient image set;

determining, on the basis of the atlas data and the patient data, the atlas image which represents at least a part of the general anatomical structure which exhibits pathological changes in accordance with the patho parameter; and determining the matching transformation which matches the atlas image and the patient image and in particular matches the spatial meta information to the patient image.

The above-described method represents an alternative and independent method of an alternative and independent embodiment. The above-described method is preferably combined with the method described in aspect 1 of Annex B or any of aspects 2 to 13 of Annex B. As described above, atlas data are acquired which contain information on a description of a plurality of images of the general anatomical structure for a plurality of patho parameters, i.e. each image of the plurality of images specifies a particular general anatomical structure which exhibits a particular pathological change. The information on the description is in particular the image (atlas image) of the general anatomical structure which is associated with the particular patho parameter and/or can be spatial information on the general anatomic structure as described above which is associated with the particular patho parameter and/or can be element representation information as described above which is associated with the particular patho parameter. In accordance with another step of this alternative method, the patient data are acquired. The patient data comprise at least one patient image which is associated with a particular patho parameter. This allows the information on the description of one of the plurality of images of the general anatomical structure, which exhibits the pathological changes specified by the particular patho parameter, to be determined. If the information on the description is an atlas image, then the atlas image is determined by selecting the atlas image which is associated with the particular patho parameter. In a following step, the matching transformation which matches the atlas image and the patient image to each other and in particular matches the atlas image to the patient image (both of which are associated with the same patho parameter) is determined.

As mentioned above, the alternative method can be combined with the method described above. In particular, the atlas data describe the spatial information on the general anatomical structure for a plurality of different patho parameters. The spatial information of atlas elements can in particular vary in accordance with the patho parameters, for example due to deformation caused by tumours. The element representation information also varies in accordance with the patho parameters. In particular, a spatial distribution of representation information within the different anatomical elements (atlas elements) varies in accordance with the patho parameters. The spatial distribution of the representation information in particular represents an average spatial distribution of pathological changes associated with the respective patho parameter. In addition to the element representation information or as an alternative to the element representation information, meta data referred to as patho meta data can be acquired. The patho meta data describe meta information on pathological changes to the general anatomical structure associated with a particular patho parameter. This meta information can in particular be a statistical probability distribution for the presence of pathological changes within the respective atlas elements (in particular, a spatial statistical distribution of such a probability which depends on positions or sub-regions within the atlas element) and/or can be information on an average geometry of distinct pathological changes (distinct tumours) and/or can be information on an average number of distinct pathological changes and variations of said number. In particular, the matching transformation can transform (and in particular deform) the spatial statistical probability distribution associated with the atlas image onto the patient image by using the matching transformation, i.e. the spatial statistical probability distribution of pathological changes represents spatial meta information on the pathological changes which is matched to the patient image. The spatial statistical distribution is an example of spatial meta information.

If, for example, the atlas data only contain spatial information on the general anatomical structure and the spatial meta information, then the spatial properties of the white atlas elements to be matched to the patient image are determined on the basis of the patho parameter, and the spatial meta information for the white atlas elements is determined on the basis of the patho parameter. The spatial statistical probability distribution can for instance be described by a two-dimensional or three-dimensional contour line model. This model is deformed in accordance with the deformation of the spatial properties of the atlas elements when the atlas element (the white atlas element combined with the spatial meta information) is matched to the patient image.

Additional features of Annex B are disclosed in the following description of embodiments. Different features of different embodiments can be combined.

Description of FIGS. 15A to 18

FIGS. 15A to 15D show the steps of the data processing method in one embodiment of Annex B.

Figure 16:
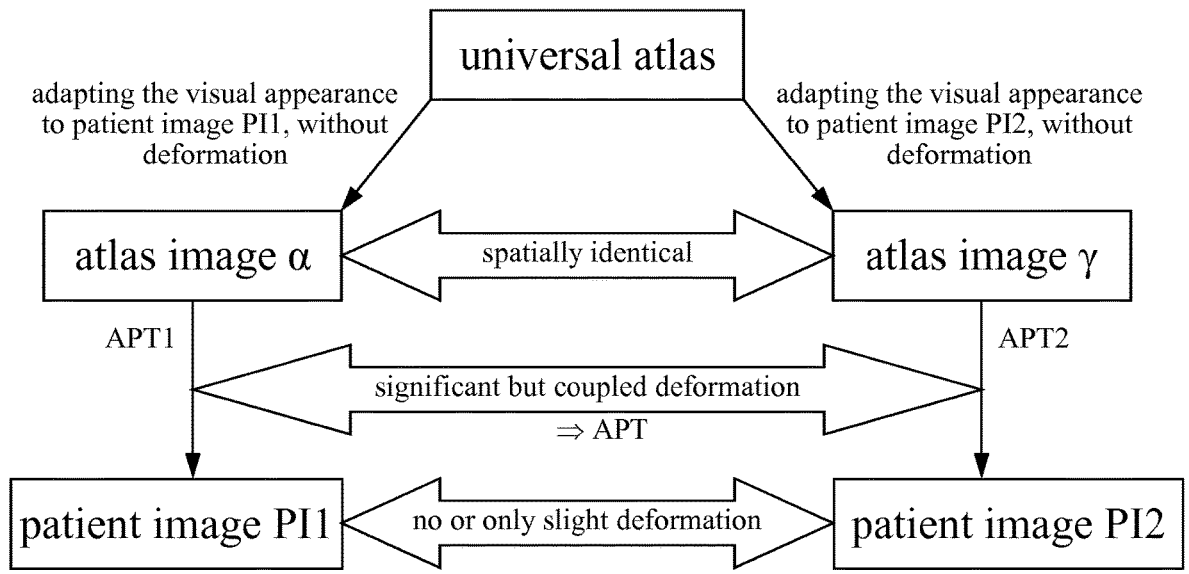
FIG. 16 shows a flow diagram which illustrates and explains correlated matching as described in Annex B.

FIG. 16 shows a flow diagram which illustrates and explains correlated matching.

Figure 17:
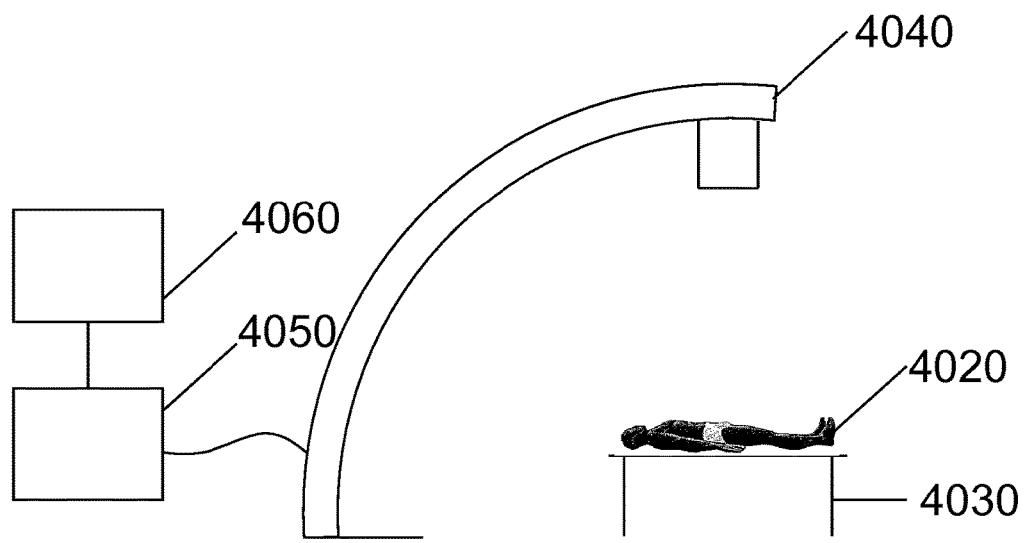
FIG. 17 shows a medical image processing system as described in Annex B.

FIG. 17 shows a medical image processing system in accordance with an embodiment of Annex B.

Figure 18:
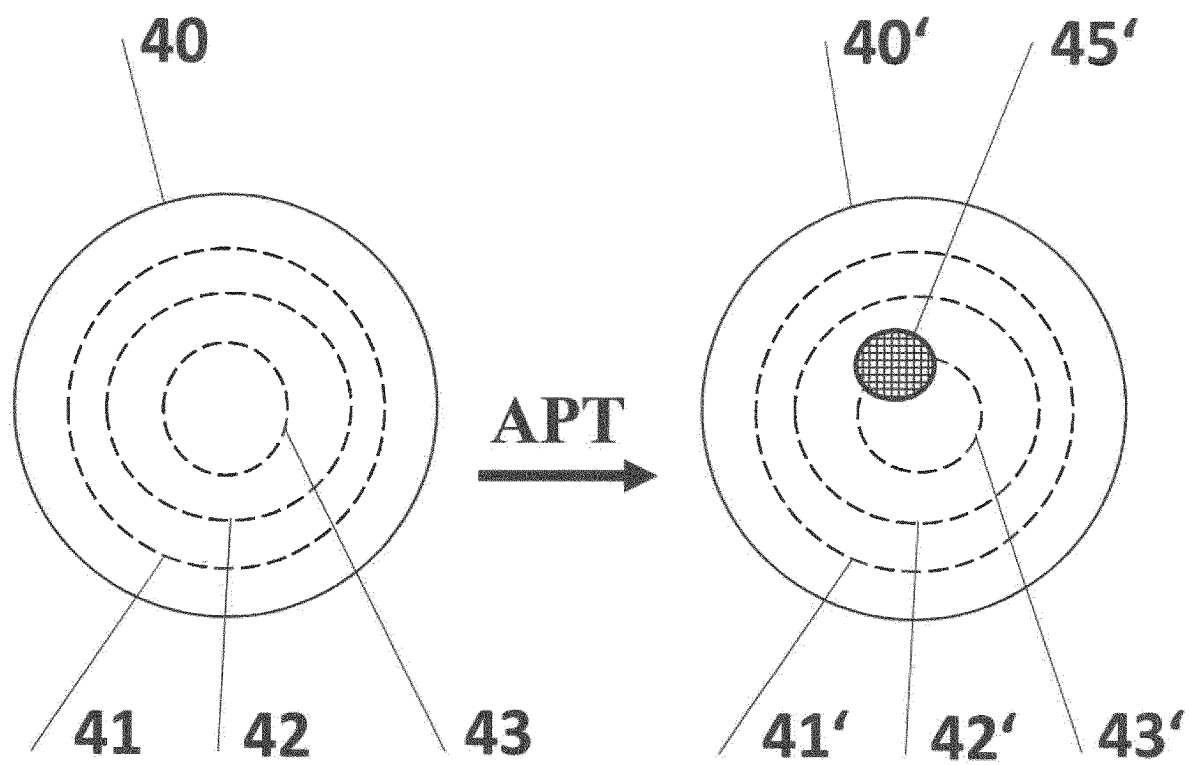
FIG. 18 illustrates how spatial meta information are matched as described in Annex B.

FIG. 18 illustrates how spatial meta information are matched.

FIGS. 15A to 15D show the steps of an embodiment of the data processing method of Annex B. The individual steps and/or sub-steps of this embodiment are described on the left-hand side in FIGS. 15A to 15D. Explanatory drawings pertaining to the individual steps are respectively shown on the right-hand side in FIGS. 15A to 15D, i.e. each of the explanatory drawings refers to the method step directly to the left of it.

In a first step S110, atlas spatial information is acquired. The atlas spatial information describes the geometry of the atlas elements and their relative position. The accompanying explanatory drawing illustrates the geometry and relative position in two-dimensional space of seven atlas elements 401 to 407. The atlas is preferably three-dimensional.

Further below in FIG. 15A, Step S120 begins with the sub-step S121. In the course of Step S120, representation information is acquired. Acquiring the representation information preferably involves acquiring an assignment between atlas elements and representation classes (Sub-step S121). The use of representation classes allows the data processing load to be reduced and in particular reflects the physical property of an anatomical body that different anatomical elements can consist of the same substance (tissue). As shown in Table 401 to the right of Sub-step S121, each of the atlas elements 401 to 407 is assigned to one of the representation classes 400A, 400B, 400C and 400D. The atlas element 401 is for example assigned to the representation class 400A, the atlas element 405 is assigned to the representation class 400D, and the atlas element 407 is assigned to the representation class 400B. Since the atlas element 402 is also assigned to the representation class 400B, assignment is preferably surjective, i.e. different atlas elements can be assigned to the same representation class. This reduces the processing load.

Figure 15A:
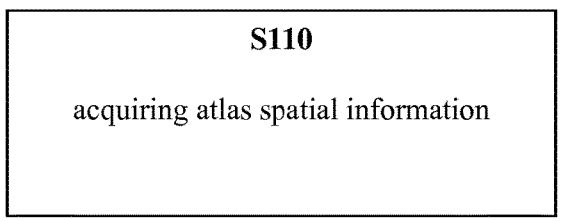
Figure 15A:
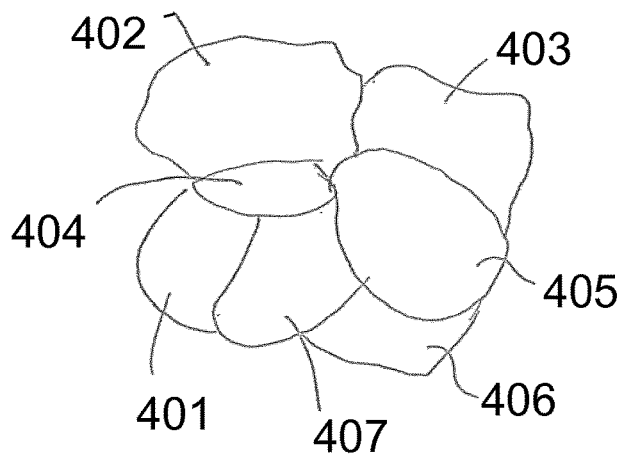
Figure 15A:
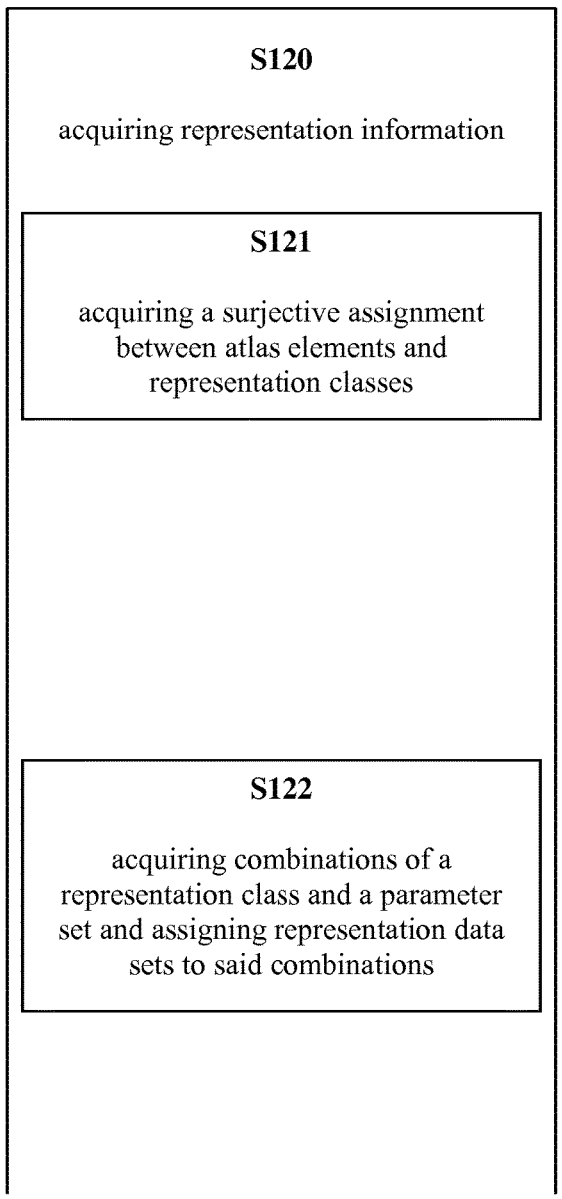
Figure 15D:
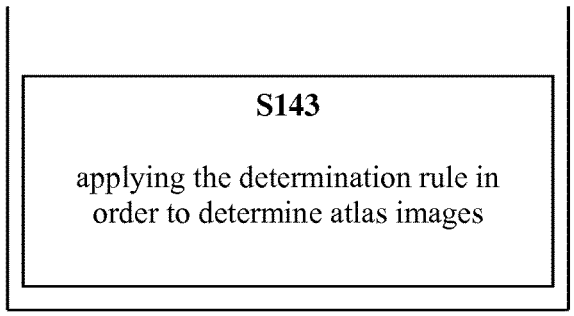
Figure 15D:
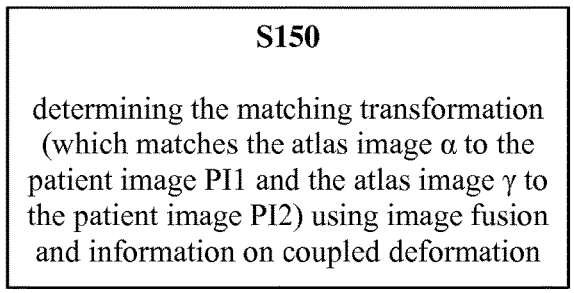
Figure 15D:
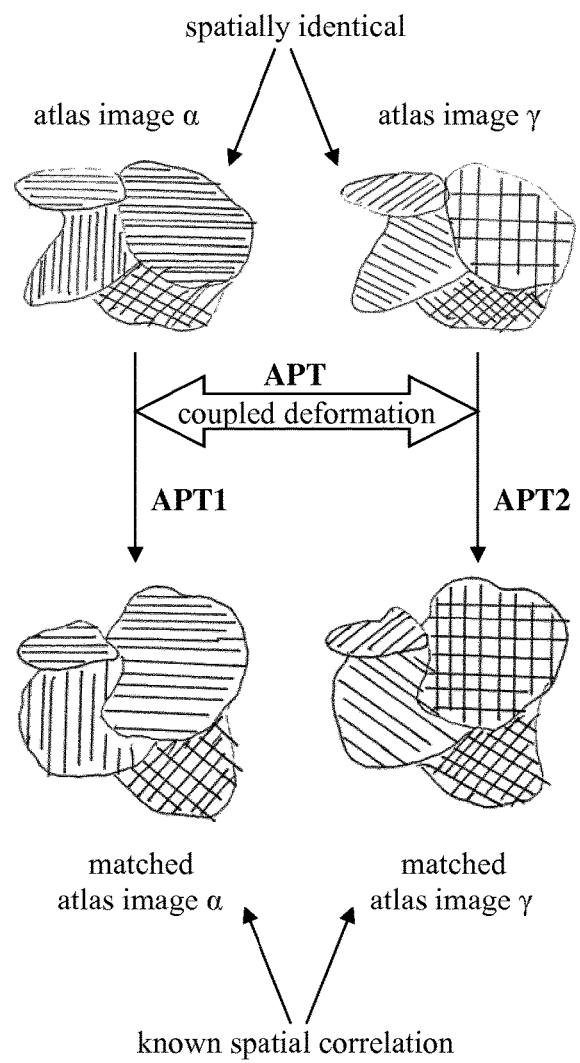

Sub-step S122 is shown at the bottom left of FIG. 15A. In this sub-step, representation data sets are assigned to combinations of a representation class and a parameter set. The representation data set a is for example assigned to a combination of the representation class 400A and the parameter set α. Preferably, all or at least most of the possible combinations of representation classes and parameter sets are assigned one of the representation data sets. An example of such an assignment is shown in Table 402. Thus, for example, the atlas element 405 is assigned to the representation class 400D, as shown in Table 401, and the representation class 400D is represented in accordance with the representation data set 400c if the parameter set is a and/or is represented in accordance with the representation data set 400d if the parameter set is β and/or is represented in accordance with the representation data set 400i if the parameter set is γ. This reflects the fact that anatomical elements can be represented differently, depending on the parameter set (for example, the image modality).

Sub-step S123 is shown at the top left of FIG. 15B. In Sub-step S123, the description of the representation data set is acquired, i.e. representation information which in particular describes the visual appearance of an anatomical element (except for spatial information such as geometry and/or size) is described. In the given example, the representation data set 400c features horizontal, parallel lines as an example of a visual appearance. The lines shown in the right-hand column of Table 403 are intended to represent for example the different grey values in an anatomical image generated by an analytical device. The letters in the left-hand column of Table 403 can for instance represent particular grey values.

In addition to the aforementioned sub-steps S121, S122 and S123, an additional sub-step S124 within Step S120 is also shown, in which a determination rule is acquired. It should be noted at this juncture that the sequence of method steps shown in FIGS. 15A and 15B is not obligatory.

Sub-step S124 relates to the step of acquiring the determination rule. In accordance with one embodiment, the determination rule describes how a representation class is selected for an atlas element using a table which assigns atlas elements to respective representation classes. When applying the rule, the corresponding elements have preferably already been identified, such that the representation classes assigned to the corresponding elements are determined in a first sub-step of the determination rule (using Table 401). In accordance with a second part of the determination rule, the representation class selected for the corresponding element and the parameter set associated with the patient image (to which the atlas image is to be matched) are used to determine the representation data set (using Table 402). The representation data sets for the corresponding elements are thus determined in the second sub-step of the determination rule.

A third part of the determination rule stipulates that the representation information corresponding to the representation data set can be acquired for instance by using a table in order to allow particular representation information to be assigned to the respective corresponding elements when the determination rule is to be applied (see Sub-step S143).

In short, the determination rule in particular regulates the way in which the representation information for the atlas elements is to be determined when the corresponding elements and the parameter sets are known.

The step of acquiring patient data is shown at the top left of FIG. 15C. This step S130 comprises two sub-steps S131 and S132. The first sub-step S131 relates to acquiring a patient image set. In the example given at the top right of FIG. 15C, the patient image set comprises a patient image PI1 and a patient image PI2. A parameter set is respectively assigned to each of the patient images, i.e. the parameter set α is assigned to patient image PI1, and the parameter set γ is assigned to patient image PI2.

The patient data preferably also comprise information on the spatial correlation between the patient images in the patient image set. The spatial correlation is in particular known. It is for example known that the spatial information is identical, i.e. the geometry and size of the anatomical elements shown in the patient image and their relative position is identical, or that the deviations from such identity are negligible. In accordance with an alternative embodiment, the patient images are not identical, but a spatial transformation is known which allows the spatial information of one patient image to be transformed into the spatial information of another patient image. One of the analytical devices may for example generate a known spatial distortion which can be described by a spatial transformation. Even if the spatial distortion is not known, spatial distortions usually have a low spatial frequency, such that it is preferably assumed that high spatial frequency information included in the patient images is identical.

In addition to the patient image sets acquired in Sub-step S131, parameter sets are preferably also acquired in Sub-step S132. In the example given to the right of Sub-step S132, the parameter set α is acquired for the patient image PI1, and the parameter set γ is acquired for the patient image PI2.

The aforementioned data acquisition steps S110, S120 and S130 can be performed in parallel or sequentially. The atlas image set is then determined in Step S140.

Step S140 preferably comprises the sub-step S141 in which the correspondence element data are acquired. The correspondence element data describe the atlas element which corresponds to the structure shown in the patient images of the patient image set, i.e. the atlas elements which have corresponding patient elements in the patient images and are to be the subject of a matching transformation. In the example given, the correspondence element data describe the atlas elements 404, 405, 406 and 407 as being corresponding elements.

In another part of S140, namely Sub-steps S142 and S143, the determination rule is applied in order to determine the atlas images. To this end, the representation data sets are determined for each of the corresponding elements 404, 405, 406 and 407 and for each of the atlas images α and γ by referring to Tables 401 and 402, i.e. Table 401 indicates the representation class 400C for the atlas image α and the corresponding element 404, and Table 402 indicates the representation data set 400c for the representation class 400C and the parameter set α. As can be seen from the table at the bottom right of FIG. 15C, the corresponding elements 404 and 405 have the same representation data set in the atlas image α but different representation data sets in the atlas image γ, i.e. the atlas elements 404 and 405 can only be differentiated in the atlas image γ. As can also be seen from the patient images PI1 and PI2, only patient image PI2 shows different grey values between the top left and top right of the image.

Since the atlas images α and γ are generated from the same atlas, the spatial information (geometry and size) of the atlas image α is identical to the spatial information of the atlas image γ.

In a subsequent step S150, the matching transformation is determined. In the example shown in FIG. 15D, the matching transformation is an AP transformation which matches the atlas image α to the patient image PI1 and the atlas image γ to the patient image PI2. The spatial correlation between the patient image PI1 and the patient image PI2 is preferably known. In the example given, the spatial information of patient images PI1 and PI2 is identical, i.e. the atlas images α and γ undergo the same deformation. This is an example of coupled deformation. As mentioned above, the corresponding elements 404 and 405 have the same representation data set for α but different representation data sets for γ. This allows the corresponding elements 404 and 405 to be segmented even for the matched atlas image α, since the deformation is coupled and the spatial information of the matched corresponding element 405 in the matched atlas image α is therefore the same as the spatial information of the matched corresponding element 405 in the matched atlas image γ, i.e. the spatial information of bone structures in a CT image can for example be used in order to identify the corresponding structures in an MR image, while conversely, the spatial information on anatomical elements consisting of soft tissue as provided by MR images can be used to determine the corresponding matched atlas elements in a matched atlas image representing a CT image.

The aforementioned AP transformations (APT1 and APT2) can be determined simultaneously or iteratively. If iteratively determined, a first trial APT1 is for example determined which results in a best match between the atlas image α and the patient image PI1. Information on deformation is extracted from the first trial APT1. The deformation from the first trial APT1 is then applied when matching the atlas image γ to the patient image PI2 by means of a first trial APT2. The first trial APT2 is then varied by varying the deformation, in particular within a predetermined range. If a varied deformation results in a better match, then this varied deformation is used to determine a second trial APT1. The second trial APT1 uses the varied deformation to match the atlas image α to the patient image PI1. Again, the second trial APT1 can be varied by varying the deformation, in particular within a predetermined range, in order to determine another modified deformation which can then in turn be applied in order to determine a second trial APT2. This process can be repeated until varying the deformation no longer improves the averaged matching quality for APT1 and APT2. Instead of the sequential determination approach described above, a simultaneous determination approach is also possible and represents another preferred embodiment.

In accordance with one embodiment, the deformations described by APT1 and APT2 are described by using deformation vectors and establishing a common reference system for APT1 and APT2 (for example, by way of a preliminary rigid transformation as mentioned above). In accordance with one embodiment, the deformation vectors determined for APT1 and APT2 are added in a first iterative step of determining the matching transformation, i.e. a first deformation vector for describing the deformation of a part of the atlas image α by APT1 and a second deformation vector for describing the deformation of a part of the atlas image γ by APT2 are for example provided. These deformation vectors for the atlas image α and the atlas image γ preferably originate at the same spatial point or region in a common reference system. Usually, fusion algorithms result in a deformation vector of 0 if no clear information on deformation can be found. If the deformation can only be reliably determined from one of the transformations APT1 and APT2, then adding the deformation vectors means that the determination is primarily based on the part of the matching transformation which provides the most information. The deformation described by the matching transformation is therefore preferably weighted in accordance with the amount of image information (described for instance by image energy or contrast) available in at least one of the patient image and atlas image, preferably the patient image. The matching transformation is preferably determined for all or at least most of the parts of the images in the way described above, by determining a plurality of deformation vectors for each transformation.

FIG. 16 schematically shows and describes an embodiment of Annex B.

The universal atlas describes the general anatomical structure and is used to determine an atlas image α and an atlas image γ. The atlas images α and γ are spatially identical, but their representation information is respectively adapted in accordance with the parameter set of the patient image to which each atlas image is to be matched, i.e. the visual appearance of the atlas image α is adapted so as to approach the visual appearance of the patient image PI1 by using the parameter set associated with the patient image PI1, and the representation information of the atlas image γ is determined on the basis of the parameter set associated with the patient image PI2 in order to approach the visual appearance of the patient image PI2. The matching transformation APT is then determined which can comprise sub-transformations APT1 and APT2 which are coupled with respect to the spatial information, in particular with respect to deformation. If, in particular, the patient images PI1 and PI2 exhibit the same spatial information or there is only a slight deviation between the patient image PI1 and the patient image PI2, then the patient images PI1 and PI2 can be assumed to be spatially identical. As a consequence, there is a constraint on the determination of APT. In the example given, the constraint would be that the deformation described by APT1 is the same as the deformation described by APT2.

FIG. 17 shows a medical image processing system in which a patient 4020 lies on a couch 4030 and an analytical device 4040 is provided in order to generate an analytical image of the patient 4020. The analytical device 4040 is connected to a computer 4050 which comprises a monitor 4060. The computer 4050 is used to run a program which performs the data processing method as described in this document, in order in particular to display atlas images and/or patient images and/or matched atlas images on the monitor 4060.

FIG. 18 illustrates how spatial meta information are matched. A white atlas element 40 is shown on the left in FIG. 18, which is combined with spatial meta information on the pathological changes. The spatial meta information is represented by contour lines 41, 42 and 43 which represent lines of constant probability for a pathological change along the line if the atlas element is associated with a particular patho parameter (for instance, a particular TNM classification). For instance, the probability of a tumour inside the contour line 41 is more than 10%, the probability of a tumour inside the contour line 42 is more than 50% and the probability of a tumour inside the contour line 43 is more than 90%. The determined matching transformation is then applied to the atlas element 40 and matches the atlas element 40 to the patient element 40' which has already been segmented, for instance using the corresponding method described in this document. The matching transformation is also applied to the spatial meta information. In the example given, the matching transformation is also applied to the contour lines, resulting in the matched contour lines 41', 42' and 43', i.e. the image on the right in FIG. 18 reflects a spatial statistical probability distribution of pathological changes. This image can be overlaid with the actual image of the patient, which then for example highlights an identified pathological change in the cross-hatched area 45'. Radiotherapy can for example be planned on the basis of the combined images. Radiotherapy can for example be planned not only on the basis of the cross-hatched area 45' but also on the basis of the contour lines 41', 42' and/or 43'. It is for example possible to plan for the application of the radiotherapy treatment to be expanded to the area within the contour line 42' in order to suppress possible pathological changes which cannot yet be identified by means of analytical images. Conversely, if the total patient element 40' is usually treated, the application of the radiotherapy treatment can be restricted to the area within the contour line 41'.

Different Aspects According to Annex B

According to a first aspect, a data processing method is disclosed, the method being for determining a matching transformation for matching a set of one or more images of an anatomical body structure of a patient, referred to as a patient image set, and a set of one or more images of a general anatomical structure, referred to as an atlas image set, wherein the general anatomical structure comprises a plurality of anatomical elements referred to as atlas elements, and each patient image is associated with one of a plurality of different parameter sets, wherein the parameter sets comprise one or more parameters which obtain when the patient images are generated, and the parameters influence representations of anatomical elements in the patient images, the method comprising the following steps performed by a computer:

acquiring atlas data (S110, S120), comprising the steps of
acquiring atlas spatial information (S110) which contains spatial information on the general anatomical structure, and
acquiring element representation information (S120) which describes a plurality (in particular, a multitude) of representation data sets (Table 3) which contain information on representations of the plurality of atlas elements in the atlas images to be determined, wherein the element representation information describes a determination rule (S124) for determining respective representation data sets for respective atlas elements in accordance with different respective parameter sets;
acquiring patient data (S130), comprising the sub-steps of
acquiring the patient image set (S131), and
acquiring one or more of the plurality of parameter sets (S132) which are respectively associated with the one or more images of the patient image set;
determining (S140), on the basis of the atlas data and the patient data, the set of atlas images which respectively represent at least a part of the general anatomical structure by using (S141b) the spatial information on the general anatomical structure and particular representation data sets which are determined (S142) by applying the determination rule (S143) in accordance with the one or more associated parameter sets and particular atlas elements acquired (S141a) and referred to as corresponding elements, which are to be matched to corresponding anatomical elements represented in the patient image;

determining (S150) the matching transformation (APT; APT1, APT2) which matches the atlas image set and the patient image set, by matching images associated with the same parameter set to each other.

According to a second aspect, the data processing method according to the first aspect is provided, wherein determining the atlas image set involves:

determining (S142) the representation data sets (Table 4) for the corresponding elements, wherein for each atlas image to be determined, one of the representation data sets is determined for each of the corresponding elements in accordance with the determination rule, wherein the determination rule comprises an assignment rule (S121, Table 1, S122, Table 2) for assigning a respective representation data set to a respective corresponding element in accordance with the parameter set associated with the patient image to which the atlas image which includes the corresponding element is to be matched; and determining the atlas image set (S143) comprising one or more images which are respectively associated with one of the parameter sets, by respectively using (S142) the determined representation data sets (Table 4) to determine the representations of the corresponding elements.

According to a third aspect, the data processing method according to any one of the preceding aspects is provided, wherein in order to determine the representation of one or more of the corresponding elements in the one or more atlas images, image values of patient elements are used in combination with determining the matching transformation.

According to a fourth aspect, the data processing method according to any one of the preceding aspects is provided, wherein the step (S150) of determining the matching transformation, which matches one of the atlas images and one of the patient images associated with one of the parameter sets to each other, is configured such that the matching transformation is determined on the basis of information on the matching transformation between another of the atlas images and another of the patient images associated with another of the associated parameter sets (FIG. 16).

According to a fifth aspect, the data processing method according to any one of the preceding aspects is provided, wherein the matching transformation is designed to deform a part of the geometry of the general anatomical structure in order to match the atlas images to the patient images, and wherein determining the matching transformation involves taking into account information on the influence on matching quality of a deformation of at least one of the atlas images associated with at least one of the parameter sets in order to determine the deformation of at least another of the atlas images which is associated with at least another of the parameter sets and includes corresponding elements which are identical to the corresponding elements included in said at least one of the atlas images.

According to a sixth aspect, the data processing method according to the preceding aspect is provided, wherein determining the matching transformation involves taking into account the fact that the spatial information described by the atlas images is identical and also taking into account information on the spatial correlation between the spatial information described by the patient images in order to determine deformations described by the matching transformation which is applied in order to match the atlas images and patient images to each other.

According to a seventh aspect, the data processing method according to any one of the preceding aspects is provided, wherein the matching transformation (APT) comprises a set of coupled transformations referred to as matching sub-transformations (APT1, APT2), wherein the respective matching sub-transformations (APT1, APT2) respectively match the atlas images associated with one of the associated parameter sets and the patient image which is associated with the same respective associated parameter set to each other, and the matching sub-transformations are coupled in that they each influence the determination of the other.

According to an eighth aspect, the data processing method according to any one of the preceding aspects is provided, wherein the determination rule describes an assignment between the plurality of atlas elements and the plurality of representation data sets by describing a surjective assignment between the atlas elements and representation classes, wherein the respective representation classes respectively represent subsets of the plurality of representation data sets, and wherein for each of the respective representation classes, there is a unique set of characteristic bijective assignments between individual representation data sets of the subsets and individual parameter sets.

According to a ninth aspect, the data processing method according to any one of the preceding aspects is provided, wherein the representation data sets describe at least one of the following types of information on representation: image values for the anatomical elements; ranges of image values for the anatomical elements; the relationship between image values of different anatomical elements; the relationship between image values for one or more of the anatomical elements represented in images associated with different parameter sets; maximum image values for the anatomical elements; minimum image values for the anatomical elements; average image values for the anatomical elements; standard deviations of the average image values and structures of modulations of the image values for the anatomical elements; characteristics of transitions between representations of different anatomical elements.

According to a tenth aspect, the data processing method according to any one of the preceding aspects is provided, wherein the atlas data also comprise spatial flexibility information which describes a flexibility of the position of atlas elements within the general anatomical structure, and wherein the matching transformation is determined on the basis of the spatial flexibility information.

According to an eleventh aspect, the data processing method according to any one of the preceding aspects is provided, further comprising the step of acquiring correspondence part data which describe the corresponding elements, wherein the acquisition step involves acquiring coarse atlas spatial information which describes the spatial information on the general anatomical structure in less detail than the atlas spatial information used to determine the atlas image set, wherein the acquisition step also involves applying a rigid matching transformation for matching the at least one patient image to a part of the general anatomical structure described by the coarse atlas spatial information, in order to determine the part of the general anatomical structure which allows a predetermined optimum of the matching result to be achieved, in particular a predetermined optimum of a measure of similarity, when determining the matching transformation, and wherein the corresponding elements are determined on the basis of the atlas elements included in the determined part.

According to a twelfth aspect, the data processing method according to any one of the preceding aspects is provided, wherein the atlas spatial information comprises a description of a plurality of different states of the general anatomical structure which are respectively described by different sets of spatial information, wherein the plurality of different states correspond in particular to a time-dependent set of spatial information which in particular comprises a description of a time-dependent vital movement of at least part of the general anatomical structure, wherein acquiring the correspondence part data involves determining the state and in particular time, which allows a predetermined optimum of the matching result to be achieved, in particular a predetermined optimum of a measure of similarity, when determining the matching transformation.

According to a thirteenth aspect, the data processing method according to any one of the preceding aspects is provided, comprising the step of applying the matching transformation to the atlas image set in order to determine matched atlas images or applying the matching transformation to the patient image set in order to determine matched patient images.

According to a fourteenth aspect, a data processing method for determining a matching transformation is provided, the method being for matching an image of an anatomical body structure of a patient, referred to as a patient image, and an image of a general anatomical structure, referred to as an atlas image, both the anatomical body structure of the patient and the general anatomical structure comprising pathological changes, wherein the patient image being associated with one of a plurality of different parameters referred to as patho parameters, wherein the patho parameters specify the pathological changes in accordance with a classification, the method comprising the following steps performed by a computer:

acquiring atlas data which contains information on a description of a plurality of images of the general anatomical structure for a plurality of patho parameters and in particular spatial meta information on the pathological changes, and acquiring patient data, comprising the sub-steps of acquiring the patient image, and acquiring the patho parameter associated with the patient image;

determining, on the basis of the atlas data and the patient data, the atlas image which represents at least a part of the general anatomical structure which comprises pathological changes in accordance with the patho parameter and which part corresponds to at least a part of the anatomical structure represented on the patient image; and determining the matching transformation which matches the atlas image and the patient image, and in particular which matches the spatial meta information to the patient image.

According to a fifteenth aspect, the data processing method of the preceding aspect is provided, wherein the method is for determining a matching transformation for matching a set of one or more images of the anatomical body structure of the patient associated with the same patho parameter, referred to as a patient image set, and a set of one or more images of the general anatomical structure, referred to as an atlas image set, wherein the general anatomical structure comprises a plurality of anatomical elements referred to as atlas elements, and each patient image is associated with one of a plurality of different parameter sets, wherein the parameter sets comprise one or more parameters which obtain when the patient images are generated, and the parameters influence representations of anatomical elements in the patient images, wherein the information on the description of an atlas image is a plurality of spatial information on a plurality of general anatomic structures respectively associated with one of the plurality of patho parameters, the step of acquiring atlas data comprises:

acquiring atlas spatial information which contains a plurality of spatial information on the general anatomical structure for a plurality of patho parameters, and acquiring element representation information which describes a plurality (in particular, a multitude) of representation data sets which contain information on representations of the plurality of atlas elements in the atlas images to be determined for a plurality of patho parameters, wherein the element representation information describes a determination rule for determining respective representation data sets for respective atlas elements in accordance with different respective parameter sets and in accordance with the patho parameter associated with the set of patient images;

the step of acquiring patient data comprising the sub-steps of acquiring one or more of the plurality of parameter sets which are respectively associated with the one or more images of the patient image set and which are respectively associated with the same patho parameter;

determining, on the basis of the atlas data and the patient data, the set of atlas images which respectively represent at least a part of the general anatomical structure associated with the patho parameter by using the spatial information on the general anatomical structure associated with the patho parameter and particular representation data sets associated with the patho parameter which are determined by applying the determination rule in accordance with the patho parameter and one or more associated parameter sets and particular atlas elements acquired and referred to as corresponding elements, which are to be matched to corresponding anatomical elements represented in the patient image;

determining the matching transformation which matches the atlas image set and the patient image set, by matching images associated with the same parameter set and the same patho parameter to each other;

the method in particular comprising the steps as described in any one of the second to the thirteenth aspect of Annex B.

According to a sixteenth aspect, a program is provided which, when running on a computer or when loaded onto a computer, causes the computer to perform the method steps of the method according to any one of the preceding aspects and/or a program storage medium on which the program is stored and/or a computer on which the program is running or into the memory of which the program is loaded and/or a signal wave, in particular a digital signal wave, carrying information which represents the program.

According to a seventeenth aspect, a medical image processing system is provided, comprising:

analytical devices for generating patient images of a patient; and a computer according to the preceding claim which is designed to determine the matching transformation and apply the matching transformation in order to match the generated patient images and determined atlas images.

The invention claimed is:

1. A computer implemented method for generating a compartmentalized dynamic anatomic atlas, the method comprising:

acquiring static atlas data which is compartmentalized into at least a first compartment that includes only spatial element data and a second compartment that includes only element representation data,
   wherein the spatial element data describes spatial properties of a spatial atlas element and does not contain any information about a representational property of the spatial atlas element, wherein the spatial properties include static spatial information describing a geometry and a position of the spatial atlas element, and
   wherein the element representation data describes representational properties assignable to the spatial atlas element and does not contain any information about the spatial properties of the spatial atlas element, wherein the representational properties include representation information describing a pixel or voxel value for the spatial atlas element; and
acquiring dynamic atlas data which includes at least information on a dynamic property which information is respectively linked to the spatial properties of the spatial atlas element independently from the representational properties of the spatial atlas element, the dynamic property describing a time-dependent movement or deformation of the spatial atlas element; and
generating the compartmentalized dynamic anatomic atlas by: determining the information on the dynamic property to be linked to the corresponding spatial atlas element based on the information on the dynamic property linked to a patient element, the patient element being an anatomical body part represented in a patient image, and linking the information on the dynamic property to the corresponding spatial atlas element,
   wherein the dynamic atlas data is linked with the static atlas data.

2. The computer implemented method for generating the compartmentalized dynamic anatomic atlas of claim 1, wherein the dynamic property of the generated dynamic atlas data is at least one of:
   a change of the position of the spatial atlas element and
   a change of the geometry of the spatial atlas element.

3. The computer implemented method for generating the compartmentalized dynamic anatomic atlas of claim 1, wherein the information on the dynamic property contains at least one trajectory defining a time-dependent position of the spatial atlas element or of a point with a known spatial relationship to the spatial atlas element.

4. The computer implemented method for generating the compartmentalized dynamic anatomic atlas of claim 1, wherein the spatial element data describes spatial properties of multiple spatial atlas elements, and wherein the information on the dynamic property describes correlations between dynamic properties of different ones of the multiple spatial atlas elements.

5. The computer implemented method for generating the compartmentalized dynamic anatomic atlas of claim 1, wherein the information on the dynamic property describes at least one normalized dynamic property of at least one spatial atlas element.

6. The computer implemented method for generating the compartmentalized dynamic anatomic atlas of claim 1, wherein the information on the dynamic property linked to the spatial atlas element is classified according to patient types.

7. The computer implemented method for generating the compartmentalized dynamic anatomic atlas of claim 1, wherein the information on the dynamic property includes information on a distribution of at least one dynamic property, and wherein the information on the distribution of the at least one dynamic property includes information on a distribution of a trajectory.

8. The computer implemented method for generating the compartmentalized dynamic anatomic atlas of claim 1 further comprising subdividing the spatial atlas element into spatial atlas sub-elements respectively linked with different dynamic properties while being assigned the same representational property.

9. A computer implemented method for generating a compartmentalized dynamic anatomic atlas, the method comprising:
   acquiring static patient data describing a static patient image of a patient element, the patient element being an anatomical body part represented in the static patient image;
   acquiring, based on static atlas data, a static atlas image of spatial atlas elements,
      wherein the static atlas data is compartmentalized into:
         a first compartment that includes spatial element data describing spatial properties of the spatial atlas elements, and a second compartment that includes element representation data describing representational properties of the spatial atlas elements,
         wherein the spatial properties include static spatial information describing geometries and positions for the spatial atlas elements, and
         wherein the representational properties include representation information describing pixel or voxel values for the spatial atlas elements;
   acquiring dynamic patient data comprising information on a dynamic property, the information being respectively linked to the patient element;
   matching the static patient image with the static atlas image;
   determining a corresponding spatial atlas element corresponding to the patient element based on the matching; and
   generating the compartmentalized dynamic anatomic atlas by determining the information on the dynamic property to be linked to the corresponding spatial atlas element based on the information on the dynamic property linked to the patient element and linking the information on the dynamic property to the corresponding spatial atlas element,
      wherein the dynamic atlas data is linked with the spatial element data.

10. The computer implemented method of claim 9, the method comprising at least one of the following steps:
   based on the information on the dynamic properties linked to different patient elements, correlations between the dynamic properties of the different patient elements are calculated for determining the correlations between the dynamic properties of different ones of the spatial atlas elements; and
   based on at least the information on the dynamic property linked to the patient element, at least one normalized dynamic property for the patient element is calculated for determining the at least one normalized dynamic property.

11. The computer implemented method of one of claim 9, wherein, based on patient sub-elements exhibiting different dynamic properties within the corresponding patient element, spatial atlas sub-elements corresponding to the patient sub-elements are determined.

12. A computer implemented method for enabling an analysis of an anatomic dynamic of a patient, comprising:

acquiring static atlas data and dynamic atlas data of a compartmentalized dynamic anatomic atlas,
  wherein the static atlas data is compartmentalized into:
    a first compartment that includes spatial element data describing spatial properties of the spatial atlas elements, and a second compartment that includes element representation data describing representational properties of the spatial atlas elements,
  wherein the spatial properties include static spatial information describing geometries and positions for the spatial atlas elements, and
  wherein the representational properties include representation information describing pixel or voxel values for the spatial atlas elements;
acquiring static patient data describing a static patient image of a patient element, the patient element being an anatomical body part represented in the static patient image;
acquiring a static atlas image based on the static atlas data;
matching the static patient image with the static atlas image;
determining a corresponding spatial atlas element corresponding to the patient element based on the matching;
acquiring dynamic patient data comprising information on a dynamic property, the information being respectively linked to the patient element, wherein
  the compartmentalized dynamic anatomic atlas is generated by determining the information on the dynamic property to be linked to the corresponding spatial atlas element based on the information on the dynamic property linked to the patient element and linking the information on the dynamic property to the corresponding spatial atlas element,
  the static spatial information and the representation information compartmentalized from the static atlas data are stored separately, and
  the dynamic atlas data is linked with the spatial element data; and
comparing the information on the dynamic property linked to the corresponding spatial atlas element and the information on the dynamic property linked to the patient element for enabling the analysis.

13. The computer implemented method of claim 12, further comprising:
  acquiring the static atlas data and the dynamic atlas data of the compartmentalized dynamic anatomic atlas;
  comparing at least one classified dynamic property of the corresponding spatial atlas element with the dynamic property of the patient element, by comparing predetermined trajectories with a trajectory comprised in the information on the dynamic property of the patient element, wherein, the predetermined trajectories are classified according to patient types and described by information on the dynamic property linked to the corresponding spatial atlas element; and
  determining, based on the comparison, the type of the patient.

14. The computer implemented method of claim 13, further comprising:
  acquiring the static atlas data and the dynamic atlas data of the compartmentalized dynamic anatomic atlas;
  determining whether the determined dynamic property of the corresponding patient element is within a predefined range or not based on the comparison and based on the information on a distribution of the at least one dynamic property.

15. A non-transitory computer readable storage medium comprising instructions which, when running on at least one computer, causes the at least one computer to perform the steps of:
  acquiring static patient data describing a static patient image of a patient element, the patient element being an anatomical body part represented in the static patient image;
  acquiring, based on static atlas data, a static atlas image of spatial atlas elements,
    wherein the static atlas data is compartmentalized into:
      a first compartment that includes spatial, element data describing spatial properties of the spatial atlas elements, and a second compartment that includes element representation data describing representational properties of the spatial atlas elements,
    wherein the spatial properties include static spatial information describing geometries and positions for the spatial atlas elements, and
    wherein the representational properties include representation information describing pixel or voxel values for the spatial atlas elements;
  acquiring dynamic patient data comprising information on a dynamic property, the information being respectively linked to the patient element;
  matching the static patient image with the static atlas image;
  determining a corresponding spatial atlas element corresponding to the patient element based on the matching;
  generating a dynamic anatomic atlas by determining the information on the dynamic property to be linked to the corresponding spatial atlas element based on the information on the dynamic property linked to the patient element and linking the information on the dynamic property to the corresponding spatial atlas element,
  where the dynamic atlas data is linked with the spatial element data.

* * * * *

UNITED STATES PATENT AND TRADEMARK OFFICE
CERTIFICATE OF CORRECTION

PATENT NO. : 12,112,845 B2
APPLICATION NO. : 17/281644
DATED : October 8, 2024
INVENTOR(S) : Kajetan Berlinger and Andreas Blumhofer It is certified that error appears in the above-identified patent and that said Letters Patent is hereby corrected as shown below:

In the Specification

In Column 9, Line 46, delete "$\overrightarrow{p_{x,y}}(t_n)$" and insert -- $\overrightarrow{p_{x,y,z}}(t_n)$ --, therefor.

In Column 38, Line 14, delete "Sa" and insert -- 5a --, therefor.

In the Claims

In Column 98, Claim 9, Line 31, delete "patient" and insert -- atlas --, therefor.

In Column 98, Claim 9, Line 46, delete "spatial element" and insert -- static atlas --, therefor.

In Column 99, Claim 12, Line 24, after "acquiring" insert -- the --.

In Column 99, Claim 12, Line 24, delete "patient" and insert -- atlas --, therefor.

In Column 99, Claim 12, Line 33, after "element," delete "the static spatial information and the representation information compartmentalized from the static atlas data are stored separately, and".

In Column 99, Claim 12, Line 37, delete "spatial element" and insert -- static atlas --, therefor.

In Column 100, Claim 14, Line 9, after "atlas;" insert -- and --.

In Column 100, Claim 15, Line 37, delete "patient" and insert -- atlas --, therefor.

In Column 100, Claim 15, Line 43, after "matching;" insert -- and --.

Signed and Sealed this
Twenty-sixth Day of November, 2024

Katherine Kelly Vidal
*Director of the United States Patent and Trademark Office*

In Column 100, Claim 15, Line 50, delete "where" and insert -- wherein --, therefor.

In Column 100, Claim 15, Line 50, delete "spatial element" and insert -- static atlas --, therefor.